United States Patent
Zard et al.

(10) Patent No.: US 7,820,831 B2
(45) Date of Patent: Oct. 26, 2010

(54) COMPOUNDS COMPRISING A THIOCARBONYL-SULFANYL GROUP WHICH CAN BE USED FOR THE RADICAL SYNTHESIS OF α-PERFLUOROALKYLAMINE COMPOUNDS

(75) Inventors: Samir Zard, Gif sur Yvette (FR); Fabien Gagosz, Montrouge (FR); Lucie Tournier, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 12/186,729

(22) Filed: Aug. 6, 2008

(65) Prior Publication Data

US 2008/0306281 A1    Dec. 11, 2008

Related U.S. Application Data

(62) Division of application No. 10/527,702, filed as application No. PCT/FR03/02697 on Sep. 11, 2003, now Pat. No. 7,423,161.

(30) Foreign Application Priority Data

Nov. 9, 2002 (FR) .................................. 02 11261

(51) Int. Cl.
- C07D 209/48 (2006.01)
- C07D 9/48 (2006.01)
- C07C 233/18 (2006.01)
- C07C 269/08 (2006.01)
- C07C 7/10 (2006.01)
- C07F 7/10 (2006.01)

(52) U.S. Cl. .................... 548/477; 556/419; 560/160; 564/224

(58) Field of Classification Search .................... None
See application file for complete search history.

(56) References Cited

OTHER PUBLICATIONS

Denieul et al., {Trifluoroacetonyl radicals: a versatile approach to trifluoromethyl ketones, Chemical Communications (Cambridge) (1996), (22), 2511-2512}.*
Bertrand et al., {A Xanthate Transfer Radical Process for the Introduction of the Trifluoromethyl Group, Organic Letters (2001), 3(7), 1069-1071}.*

* cited by examiner

*Primary Examiner*—Daniel M Sullivan
*Assistant Examiner*—Chukwuma O Nwaonicha
(74) *Attorney, Agent, or Firm*—Buchanan Ingersoll & Rooney PC

(57) ABSTRACT

The invention relates to compounds having the general formula (I), the method of preparation thereof and the use thereof in organic radical synthesis. The invention also relates to compounds having the formula (II), the method of preparation thereof and a method for preparing compounds having the formula (VIII).

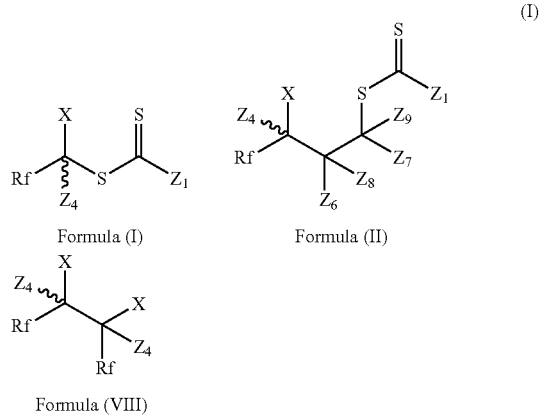

Formula (I)    Formula (II)

Formula (VIII)

25 Claims, No Drawings

COMPOUNDS COMPRISING A THIOCARBONYL-SULFANYL GROUP WHICH CAN BE USED FOR THE RADICAL SYNTHESIS OF α-PERFLUOROALKYLAMINE COMPOUNDS

CROSS-REFERENCE TO EARLIER APPLICATIONS

This application is a divisional of U.S. patent application Ser. No. 10/527,702 filed Mar. 11, 2005, which is a national stage of International Application No. PCT/FR03/02697, filed Nov. 9, 2003, which claims priority under 35 U.S.C. §119 of FR-02/11261, filed Nov. 9, 2002, all hereby expressly incorporated by reference.

The present invention relates to a new family of compounds which are useful in particular for the radical synthesis of α-perfluoroalkylamines.

The introduction of fluorine atoms into a specific molecule generally modifies the chemical properties thereof significantly. In the case of a biologically active compound, the introduction of fluorine atoms can in particular lead to a modification of the pharmacological profile of the molecule.

Therefore, numerous attempts are currently being made to develop practical methods for producing various classes of fluorine-containing compounds, in particular α-perfluoroalkylamines and more particularly α-trifluoromethylamines.

Trifluoromethylamine compounds having an advantageous biological activity thus include, for example, the following compounds

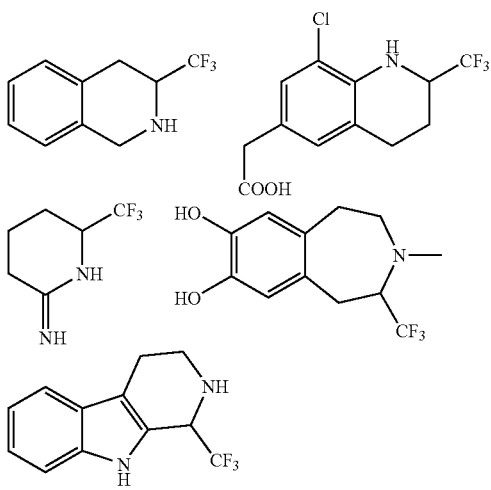

The majority of the synthesis methods currently developed for producing α-trifluoromethylamines consist in carrying out a reductive amination of the corresponding trifluoromethyl ketone compounds. However, these approaches generally suppose the use of a given number of steps to produce the initial trifluoromethyl ketone compounds and have been found to produce relatively unsatisfactory overall yields owing to the linear nature of the process; on the other hand, this approach is often incompatible with a number of functional groups which are sensitive to the action of the amine or that of the reducers used, or also to the reagents required for the synthesis of the initial trifluoromethyl ketones.

Another significant method for producing α-trifluoromethylamine compounds consists in reacting various nucleophiles, for example, of the enolated type, with iminium salts. In this regard, reference can be made in particular to the following publications: (a) Blond, G.; Billard, T.; Langlois, B. *J. Org. Chem.* 2001, 66, 4826-4830. (b) Takaya; J. H.; Kagoshima, H.; Akiyama, T. *Org. Lett.* 2000, 2, 1577-1579. (c) Dolbier, W R.; Xu, Y. *J. Org. Chem.* 2000, 65, 2134-2137. (d) Dolbier, W. R.; Xu, Y. *J. Tetrahedron Lett.* 1998, 39, 9151-9154. (d) Fuchigami, T.; Nakagawa, Y.; Nonaka, T. *J. Org. Chem.* 1987, 52, 5489-5491). However, the formation of an iminium salt at the foot of a group which is as electroattractive as a trifluoromethyl generally requires relatively strict conditions.

Surprisingly, inventors have discovered a new method which allows α-trifluoromethylamine compounds to be produced, and more generally α-per-/α-poly-fluoroalkyl/fluoroaryl amine compounds, in a direct, flexible and effective manner with satisfactory yields, starting from α-per-/α-poly-fluoroalkyl/fluoroaryl amine derivatives which comprise a thiocarbonylsulphanyl function in the α-position, and which are capable of reacting with olefins.

Compounds Having the Formula I

According to a first feature, the subject-matter of the invention is thus compounds having the general formula (I):

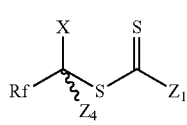

Formula (I)

in which:
X represents a group which donates through a mesomeric effect;
$Z_1$ represents a group selected from:
(i) the alkyl, acyl, aryl, aralkyl, alkene or alkyne groups, the cyclic hydrocarbons or the heterocycles,
(ii) an —$OR^a$ or —$SR^a$ group in which $R^a$ is a group selected from:
an alkyl, halogenoalkyl, alkenyl, alkynyl, acyl, aryl, arylalkyl, arylalkenyl, arylalkynyl group, or a cyclic hydrocarbon or a heterocycle, or a polymer chain;
a —$CR^bR^cPO(OR^d)(OR^e)$ group in which
$R^b$ and $R^c$ each represent, independently of each other, a hydrogen atom, a halogen atom, an alkyl group, perfluoroalkyl, a cyclic hydrocarbon or a heterocycle, or an —$NO_2$, —NCO, CN group, or a group selected from groups of the type —$R^f$, —$SO_3R^f$, —$OR^f$, —$SR^f$, —$NR^fR^g$,
—$COOR^f$, —$O_2CR^f$, —$CONR^fR^g$, —$NCOR^fR^g$, in which $R^f$ and $R^g$ each independently refer to an alkyl, alkenyl, alkynyl, cycloalkenyl, cycloalkynyl, aryl group which is optionally condensed to a heterocycle, alkaryl, arylalkyl, heteroaryl,
or $R^b$ and $R^c$ form, together with the carbon atom to which they are attached, a C=O or C=S group or a cyclic hydrocarbon or a heterocycle group; and
$R^d$ and $R^e$ each represent, independently of each other, a radical which complies with one of the definitions given above for the group $R^f$;
or $R^d$ and $R^e$ together form a hydrocarbon chain which comprises from 2 to 4 carbon atoms, and which is optionally interrupted by a group selected from —O—, —S— and —$NR^h$—; in which $R^h$ complies with one of the definitions given above for the group $R^f$;

(iii) a group —NR$^i$R$^j$, in which:

R$^i$ and R$^j$ represent, independently of each other, a radical selected from an alkyl, halogenoalkyl, alkenyl, alkynyl, acyl, ester, aryl, arylalkyl, arylalkenyl, arylalkynyl group, or a cyclic hydrocarbon or a heterocycle; or R$^i$ and R$^j$ together form a hydrocarbon chain which comprises from 2 to 4 carbon atoms and which is optionally interrupted by a —O—, —S—, or —NR$^H$—, or R$^H$ group which complies with one of the definitions given above for the R$^f$ group, the hydrocarbon chain advantageously forming a 5-membered ring with the nitrogen atom to which R$^i$ and R$^j$ are attached, Z$_4$ represents a hydrogen atom, an alkyl or cycloalkyl group, and Rf represents (i) a halogen atom, preferably fluorine;

(ii) fluoroalkyl, preferably perfluoroalkyl;

(iii) a poly- or per-halogenated aryl radical, comprising at least one, advantageously two, fluorine atom(s), or (iv) a radical selected from R$_A$—CF$_2$—, R$_A$—CF$_2$—CF$_2$—, R$_A$—CF$_2$—CF(CF$_3$)—, CF$_3$—C(R$_A$)F— and (CF$_3$)R$_A$—, with R$^A$ selected from an alkyl, acyl, aryl, aralkyl, alkene or alkyne group, the cyclic hydrocarbons or the heterocycles;

and the salts of compounds of this type.

Advantageously the group X is, or comprises, a metalloid atom which carries a lone pair, such as halogens, chalcogens and metalloids of the nitrogen group.

The "chalcogens" refer to the metalloid atoms selected from oxygen, sulphur, selenium and tellurium.

The metalloids of the nitrogen group include in particular nitrogen, phosphorus and arsenic.

This metalloid atom X carries the bond to the remainder of the molecule, that is to say, to the carbon which carries R$^f$.

X can thus be selected in particular from —NZ$_2$Z$_3$, —OZ$_5$ or Hal, where —Z$_2$ and Z$_3$ represent, independently of each other, a hydrogen atom, a group selected from the alkyls, cycloalkyls, aryls and the electroattractive groups, it being understood that at least one of the radicals Z$_2$ and Z$_3$ advantageously has an electroattractive effect with respect to the electron density of the nitrogen atom to which they are bonded, Z$_5$ represents a hydrogen atom, an alkyl, cycloalkyl, aryl group, or a group which is electroattractive with respect to the oxygen atom to which it is bonded.

X preferably represents —NZ$_2$Z$_3$.

When the metalloid atom is divalent (in the case of chalcogens) or polyvalent (in the case of nitrogen), the availability of the lone pair can be modulated by the substituents. It is thus preferable for a substituent of the metalloids to be electroattractive. For example, when X represents an atom of nitrogen or oxygen, the electroattractive group allows the conjugation of the lone pair of nitrogen or oxygen to be reduced with the thiocarbonylsulphanyl function in the α-position.

For more information on this subject, reference can be made in particular to the work of Professor Jerry March entitled "Advanced Organic Chemistry" (3rd edition), published by John Wiley and Sons.

In the context of the present description, an "electroattractive group" refers to a group which is generally at least as electroattractive as the phenyl group, and which, in the Hammett constant scale σ$_p$, corresponds to the value 0.05; it should be noted that the hydrogen value is by definition zero and that of trifluoromethyl is 0.53. According to the present invention, the electroattractive nature of the substituent(s) of the metalloid is ensured by the presence of one, and in the case of polyvalent metalloids, preferably only one, carbonyl group which is directly bonded to the metalloid.

Examples of an electroattractive group include in particular the acyl groups (σ$_p$~0.47) in the widest possible sense, including aroyl, carboxyl (σ$_p$~0.44), alkyloxycarbonyl (σ$_p$~0.44), aryloxycarbonyl, aralkyloxycarbonyl, carbamoyl, alkylcarbamoyl, arylcarbamoyl, the cyano- (σ$_p$~0.70), sulphonyl, alkylsulphonyl (σ$_p$~0.73), arylsulphonyl groups, preferably acyl, carboxyl, alkyloxycarbonyl, aryloxycarbonyl, aralkyloxycarbonyl, carbamoyl, cyano-, sulphonyl.

It should be noted that the sigma values p(ara), ((σ$_p$)) indicated above are those reported in the work of Professor Jerry March entitled "Advanced Organic Chemistry" (3rd edition), published by John Wiley and Sons.

The groups Z$_2$ and Z$_3$ can also be bonded to form, with the nitrogen atom to which they are bonded, a hydrocarbon, saturated, unsaturated or aromatic heterocycle, which preferably comprises from 5 to 6 chain links, and which is optionally interrupted by one or two atoms of nitrogen.

Preferred examples of heterocycles include in particular azoles, in particular diazoles, such as imidazole or pyrazole, and triazoles. When the heterocycle is saturated or partially saturated, it may comprise substituents of the type oxo (O═) or thioxo (S═). Pyrrolidone can be mentioned as a particular example.

In the whole of the present description, the term "alkyl" or "Alk" group is understood to cover a saturated hydrocarbon radical which is linear or branched and which can optionally include one or more saturated aliphatic ring(s). In the context of the invention, the alkyl groups may have up to 25 carbon atoms and they preferably contain from 1 to 12 carbon atoms, and advantageously from 1 to 6 carbon atoms.

The alkyl radicals which can be envisaged include, in particular the methyl, ethyl, propyl, butyl, pentyl, isopropyl, tert-butyl, (cyclo)pentyl, (cyclo)hexyl, octyl, decyl or dodecyl radical.

In the context of the present description, an alkyl group may also particularly refer to a cycloalkyl group, that is to say, a saturated cyclic hydrocarbon radical which preferably has from 3 to 10 carbon atoms.

In the context of the present description, a "polymer chain" may originate from a radical or ionic polymerisation or a polycondensation.

In the context of the present description, an "alkoxy" group itself refers to a radical —OAlk, in which Alk refers to an alkyl group as defined above.

In the context of the present description, the "halogenoalkyl" group is understood to be an alkyl radical as defined above and substituted by at least one halogen atom, the term "halogen atom" referring in this instance, as in the whole description, to an atom of fluorine, chlorine, bromine or iodine, preferably an atom of fluorine or chlorine, and advantageously an atom of fluorine. The "halogenoalkyl" groups of the invention can thus be, for example, "perfluoroalkyl" groups, that is to say, in the context of the invention, groups which comply with the formula C$_n$F$_{2n+1}$, in which n represents a whole number in the order of from 1 to 20.

Furthermore, an "alkenyl" group, in the sense in which it is used in the present description, refers to an unsaturated linear or branched hydrocarbon radical having at least one double bond C═C. The alkenyl groups of the invention may have from 2 to 25 carbon atoms and preferably comprise from 2 to 12 carbon atoms, and advantageously from 2 to 6 carbon atoms.

Examples of alkenyl groups include in particular ethenyl, propenyl, n-butenyl, i-butenyl and allyl.

In the same manner, "alkynyl" group is understood to be an unsaturated linear or branched hydrocarbon radical having at least one triple bond C≡C. The alkynyl groups of the invention generally have from 2 to 25 carbon atoms, and they preferably comprise from 2 to 15 carbon atoms, and advantageously from 2 to 6 carbon atoms.

In the context of the present description, an "aryl" or "Ar" group itself refers to an aromatic mono- or polycyclical group generally having from 5 to 20 carbon atoms, and preferably from 6 to 10 carbon atoms. It can thus be, for example, a phenyl or 1- or 2-naphthyl group. According to a specific variant, an "aryl" group in the context of the invention may include one or more heteroatoms, such as sulphur, oxygen, or nitrogen. In this particular case, the "aryl" group refers to a heteroaromatic mono- or polycyclical group. The "aryalkyl", "aralkenyl" and "aralkynyl" groups in the context of the present description are alkyl, alkenyl and alkynyl chains substituted by an aryl group as defined above, respectively.

In the context of the present description, an "acyl" group itself refers to a group having the formula —C(=O)—B, in which B refers to a hydrogen atom or a linear or branched hydrocarbon chain which is saturated or unsaturated and which comprises from 1 to 25 carbon atoms, and which can in particular be an alkyl, alkenyl, alkynyl group, the alkenyl group being able in particular to be an aryl group, as defined above.

"Aroyl" refers to an aryl-CO— group, in which the aryl group is as described in the present document. Examples of types of aroyl groups include benzoyl, 1- and 2-naphthoyl.

Preferred acyl groups are the alkyl-CO— groups in which the alkyl group more preferably refers to an alkyl in $C_1$-$C_6$. Examples of acyl groups include in particular the formyl, acetyl, propanoyl and pivaloyl groups.

When the acyl groups must also act as a protective group which can be readily released, the acyls are advantageously ester groups of carbonic acid (—CO—O—B), such as the terbutyloxycarbonyl and benzyloxycarbonyl groups.

In the context of the present description, "ester" group is understood to be a —C(=O)—OB group, in which B refers to a linear or branched hydrocarbon chain which is saturated or unsaturated and which comprises from 1 to 25 carbon atoms, and which can in particular be an alkyl, alkenyl or alkynyl group as defined above. The ester groups include in particular the alkyloxycarbonyl, aryloxycarbonyl and aralkyloxycarbonyl groups.

"Alkyloxycarbonyl" or "alkoxycarbonyl" preferably refer to an alkyl-O—OC— group, in which the alkyl group is as defined in the present description. Examples of types of alkoxycarbonyl groups include methoxycarbonyl, ethoxycarbonyl or t-butoxycarbonyl (Boc).

"Aryloxycarbonyl" preferably refers to an aryl-O—CO— group, in which the aryl group is as defined in the present description. Examples thereof are in particular phenoxycarbonyl and naphthoxycarbonyl.

"Aralkyloxycarbonyl" preferably refers to an aralkyl-O—CO— group, in which the aralkyl group is as defined in the present description. Examples of an aralkoxycarbonyl group include in particular benzyloxycarbonyl.

In the context of the present description, a radical of the "cyclic hydrocarbon" type refers to a saturated, unsaturated or aromatic cyclical group, in particular of the cycloalkyl, cycloalkenyl or cycloalkynyl type, optionally substituted, and comprising from 3 to 20 carbon atoms. A radical of the "heterocycle" type itself refers to a carbon cycle of this type interrupted by at least one heteroatom selected, for example, from N, O, S, P and Si, the carbon cycle being able to be saturated or unsaturated.

"Carbamoyl" preferably refers to an $NH_2$—CO— group.

"Carboxyl" preferably refers to a group HO(O)C— (carboxylic acid).

"Alkylcarbamoyl" preferably refers to an alkyl-NH—CO group, in which the alkyl group is as defined in the present description.

"Sulphonyl" preferably refers to a —$SO_3H$ group.

"Alkylsulphonyl" preferably refers to a group alkyl-$SO_2$— in which the alkyl group is as defined in the present description.

"Arylsulphonyl" preferably refers to a group aryl-$SO_2$—, in which the aryl group is as defined in the present description.

The various radicals may optionally be interrupted by one or more heteroatoms selected in particular from O, S, N, P and Si, or by —(C=O)—, —(C=S)—, —$SO_2$—, —SO— groups, or secondary or tertiary amines, and they can be substituted by any type of group which is not capable of interfering with a radical addition reaction or leading to parasite reactions between the compounds present, and in particular by one or more identical or different groups selected from the groups alkoxycarbonyl or aryloxycarbonyl (—COOR), carboxy (—COOH), acyloxy (—$O_2$CR), carbamoyl (—$CONR_2$), cyano (—CN), alkylcarbonyl, alkylarylcarbonyl, arylcarbonyl, arylalkylcarbonyl, phthalimido, maleimido, succinimido, amidino, guanidino, hydroxy (—OH), amino (—$NR_2$) or (—$NH_2$), halogen, perfluoroalkyl ($C_nF_{2n+1}$), allyl, epoxy, alkoxy (—OR), thioalkoxy or thioaryloxy (—SR), sulphones, phosphonates, a silyl group, a halogen atom, groups having hydrophilic or ionic properties, such as the alkaline salts of carboxylic acids, the alkaline salts of sulphonic acids or phosphonic acids, polyoxide chains of alkylene, such as polyoxyethylene POE and polyoxypropylene POP, cationic substituents (quaternary ammonium salts), R representing an alkyl or aryl group, or a polymer chain, the substituents optionally being able to be interrupted by heteroatoms. A person skilled in art will be able to select the nature of the various groups and substituents present in the compounds used in order to prevent any undesirable secondary reaction.

According to one variant of the invention, $Z_1$ represents an alkyl or aryl group.

According to a particularly preferred embodiment, $Z_1$ represents a group —$OR^a$, in which $R^a$ is as defined above. In this case, $R^a$ is preferably a group selected from the alkyls, aralkyls or cycloalkyls. Still more preferably, $R^a$ represents an alkyl group.

According to an advantageous variant of the invention, $Z_4$ represents a hydrogen atom.

Advantageously, Rf represents a group comprising a difluoromethylene chain link which carries the bond which ensures the link with the remainder of the molecule, in particular a $R_4$—$CF_2$— group.

Rf is preferably fluoroalkyl, more preferably perfluoroalkyl, preferably a trifluoromethyl radical.

According to a specific embodiment, Rf is a poly- or perhalogenated aryl radical comprising at least one fluorine atom, preferably two fluorine atoms.

According to a preferred method of the invention, the compounds having the formula (I) are compounds having the formula (Ia) in which X represents a group —$NZ_2Z_3$

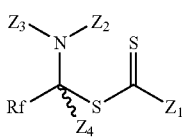

Formula (Ia)

According to a preferred variant of the invention, at least one of the groups $Z_2$ and $Z_3$ represents an acyl, alkoxycarbonyl or aralkyloxycarbonyl group, preferably acyl, for example, an acetyl, alkoxycarbonyl. Also advantageous as electroattractive groups $Z_2$, $Z_3$ are groups such as t-butoxycarbonyl (Boc), benzyloxycarbonyl, often used to protect amines since they can be readily removed.

In this context, it is particularly preferable for the other group $Z_2$ or $Z_3$ to represent a hydrogen atom or a hydrocarbon remainder advantageously having at the most 10 carbon atoms, preferably at the most 4. The hydrocarbon remainder is preferably an alkyl or aryl group.

According to another advantageous feature of the invention, the compounds are compounds having the formula (I), in which X represents —$OZ_5$, complying with the formula (Ib):

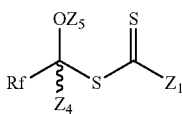

(Ib)

$Z_5$ preferably represents a hydrogen atom, an acyl or aroyl group, and more preferably an acetyl or benzoyl group.

According to another preferred method, the compounds are compounds having the formula (I) in which X represents Hal, complying with the formula (Ic):

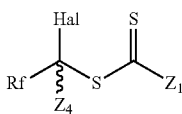

(Ic)

In the context of the present invention, "Hal" refers to a halogen atom. Hal preferably represents an atom of chlorine or bromine, and more preferably an atom of chlorine.

In particular when $Z_1$ represents an alkyl, aryl, —SR", or —OR" group, with $R^a$ selected from the alkyl, arylalkyl, cycloalkyl groups, $Z_4$ advantageously represents a hydrogen atom, Rf advantageously represents a perfluoroalkyl chain, preferably a trifluoromethyl, when X=$NZ_2Z_3$:

$Z_2$ advantageously represents an electroattractive group, such as the acyl, alkoxycarbonyl or aralkyloxycarbonyl groups, preferably acyl or alkoxycarbonyl, including in particular t-butoxycarbonyl or benzyloxycarbonyl, $Z_3$ advantageously represents either an electroattractive group which is identical to or different from $Z_2$, such as the acyl, alkoxycarbonyl or aralkyloxycarbonyl groups, preferably acyl or alkoxycarbonyl, including in particular t-butoxycarbonyl and benzyloxycarbonyl, or a hydrogen atom, an alkyl, cycloalkyl or aryl group, when X=$OZ_5$, $Z_5$ advantageously represents an acyl group, in particular aroyl, and more preferably an acetyl or benzoyl group, when X=Hal, X preferably represents a chlorine atom.

Examples of compounds according to the invention include more particularly the following compounds: S-[1-(N-acetylamino)-2,2,2-trifluoroethyl]-O-ethyl dithiocarbonate, S-1-benzoylamino-2,2,2-trifluoro-ethyl dithiocarbonic acid O-ethyl diester, S-(1-hydroxy-2,2,2-trifluoro-ethyl) dithiocarbonic acid O-ethyl ester, S-(1-acetyl-2,2,2-trifluoro-ethyl) dithiocarbonic acid O-ethyl ester, 1-ethoxythiocarbonylsulphanyl-2,2,2-trifluoro-ethyl benzoic acid ester, S-1-chloro-2,2,2-trifluoro-ethyl dithiocarbonic acid O-ethyl ester.

Method for Preparing Compounds Having the Formula I

The compounds which can be used according to the invention can be prepared by means of the application or adaptation of known methods, which are understood to be those methods which have been used up to the present time or described in literature, for example, those described by R. C. Laroche in "Comprehensive Organic Transformations", VCH Publishers, 1989.

According to a second feature, the subject-matter of the invention is a method for preparing compounds having the formula (Ia).

This method comprises the following successive steps:

a) a nucleophilic substitution of the alkoxyl function of hemiacetal $R^f$—C(OAlk)(OH)$Z_4$ (A) by means of the addition of a $Z_2Z_3$NH derivative in order to produce a compound having the formula Rf—C($NZ_2Z_3$)(OH) $Z_4$, in which Alk refers to an alkyl group, and where $R^f$, $Z_2$, $Z_3$ have the above meaning;

b) a halogenation of the hydroxyl function of the compound produced when step (a) is complete, c) a substitution of the halogen group introduced in step (b) by a derivative of thiocarbonylsulphanyl ($Z_1$—C(=S)—S—) in the form of an alkali metal salt, MS—(CS)—$Z_1$, in which $Z_1$ has the above meaning and M refers to an alkali metal.

The method for preparing a compound having the formula (Ia) according to the invention can be illustrated by the general synthesis diagram below:

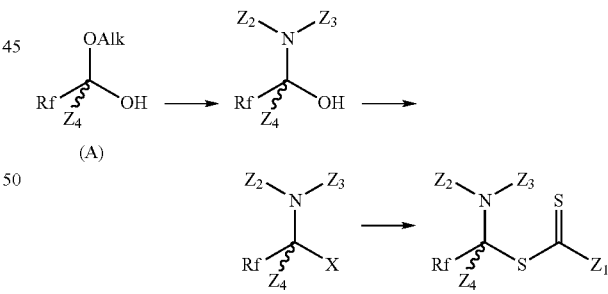

in which $Z_1$, $Z_2$, $Z_3$, $Z_4$, Rf and M have the above-mentioned definitions, Alk referring to an alkyl group and X to a halogen.

Without wishing to be limited to any one theory, these reactions are made possible by the presence of the Rf group, which advantageously has an electroattractive effect which advantageously allows the hydrate animal and hemiacetal forms (A) to be stabilised.

Whatever their precise structure, the hemiacetals Rf—C (OAlk)(OH)$Z_4$ (A) and hydrates Rf—C(OH)$_2Z_4$ which can be used as starting compounds in step (a) are readily accessible. Although some of these compounds are commercially available, they can also be prepared according to various methods of production described in the following publications: (a) Gross, U.; Rüdinger, S. in *Organo-Fluorine Compounds*; Baasner. B.; Hagemann, H.; Tatlow, J. C., Eds; Houben-Weyl: *Methods of Organic Chemistry*; Thieme: Stuttgart, 1999; Vol E10a. (b) Banks, R. E.; Smart, B. E.; Tatlow, J. C. *Organofluorine Chemistry Principles and Commercial Applications*; Plenum Press: New York, 1994. (c) Hudlicky, M.; Pavlath, A. E. *Chemistry of Organic Fluorine Compounds II. A Critical Review; ACS Monograph* 187; *American Chemical Society* Washington D.C., 1995.

According to a specific embodiment, the amine derivative $Z_2Z_3NH$ used in step (a) is an amide, and is preferably acetamide.

By way of non-limiting illustration of the solvents which are suitable for step (a) according to the invention, it is possible to mention in particular dioxane, tetrahydrofuran or dimethyl ether of ethylene glycol (DME).

The halogenation carried out in step (b) of the method preferably comprises a chlorination. Chlorination agents which allow a hydroxyl function to be substituted by a chlorine atom in step (b) and which have been found to be particularly advantageous according to the invention include thionyl chloride, phosphorus oxychloride, phosphorus trichloride, phosphorus pentachloride and phosgene.

The invention also relates to a method for preparing compounds having the formula (Ib). Compounds having the formula (Ib) can be prepared using any method known to the person skilled in the art.

Compounds having the formula (Ib), in which $Z_5$ is different from H, can in particular be prepared using a method comprising:
  a) the use of a compound (1b) in which $Z_5$=H and a compound $Z_5$—$YZ_5$ is as defined above and Y refers to a leaving group; and optionally
  b) the recovery of the product obtained.

"Leaving group" is understood to be a $Z_5$—Y bond which readily becomes unstable, in particular under the action of a nucleophile. Leaving groups are well known to the person skilled in the art. For examples of leaving groups, reference can be made in particular to the work of T. H. Greene and P. G. Wuts, "Protective Groups", in *Organic Chemistry*, John Wiley and Sons, 1991.

Y preferably represents a group —O(C=O)Alk, —O(C=O)Ar. —O(SO$_2$)Alk, —O(SO$_2$)Ar, or a halogen atom, such as chlorine or bromine.

Preferred $Z_5Y$ reagents include in particular monocarboxylic acid anhydrides, acyl halides or aroyl halides.

"Monocarboxylic acid anhydride" refers to a group (alkyl-(C=O))$_2$O or (aryl(C=O))$_2$O in which alkyl and aryl are as defined in the present description. Preferred examples thereof are in particular acetic anhydride, butyric anhydride and benzoic anhydride.

"Acyl halide" or "aroyl halide" refers to a alkyl-C(=O)-Hal or aryl-C(=O)-Hal group. Examples of acyl halides, including aroyls, are in particular acetyl chloride and benzyl chloride.

Step a) of this method preferably comprises the use of an acid or a base.

Examples of an acid which is suitable for use in step a) include in particular mineral acids, such as nitric acid, phosphoric acid, sulphuric acid, hydrochloric acid and sulphonic acids, such as methanesulphonic acid, ethanesulphonic acid, benzenesulphonic acid and p-toluenesulphonic acid. The acid is preferably used in catalytic proportions. It is generally intended to activate the departure of the leaving group.

Basic examples include in particular pyridines, including picolines and quinoline, amines, advantageously tertiary amines, such as DABCO (diazabicyclooctane), triethylamine and diisopropylethylamine.

According to another feature, the invention also relates to the preparation of a compound having the formula (Ib) in which $Z_5$ represents a hydrogen atom, comprising:
  a) the use of a compound having the formula (A):

(A)

with an acid and a compound MS—(C=S)—$Z_1$ in which $Z_1$ is as defined above and M refers to an alkali metal and Alk refers to an alkyl group; and, if necessary,
  b) the recovery of the product obtained.

The acids which can be used in this method are those as defined above.

The invention also relates to a method for preparing compounds having the formula (Ic) comprising:
  a) the use of a compound having the formula (Ib) in which $Z_5$=H in the presence of a halogenation agent, and optionally
  b) the recovery of the product obtained.

It is possible to use conventional reagents as a halogenation agent.

Examples of a chlorination agent include in particular phosgene, phosphoric reagents, such as phosphorus pentachloride (PCl$_5$), phosphorus trichloride (PCl$_3$), phosphorus oxychloride (POCl$_3$), and sulphurous reagents, such as thionyl chloride (SOCl$_2$), Examples of a bromination agent include in particular the brominated derivatives of phosphorus.

The solvents which may be suitable for carrying out the methods for preparing the compounds (Ia), (Ib) and (Ic) according to the invention can be selected from ketones, alcohols, non-protic polar solvents, halogenated hydrocarbons and aromatics.

Examples of solvents of the ketone type include in particular acetone and methyl ethyl ketone.

Examples of solvents of the alcohol type include in particular methanol, ethanol and isopropanol.

Examples of non-protic polar solvents include in particular acetonitrile, N,N-dimethylformamide (DMF) and dimethyl sulphoxide (DMSO).

Examples of a halogenated hydrocarbon include in particular dichloromethane and 1,2-dichloroethane.

Examples of an aromatic solvent include in particular benzene, toluene and chlorobenzenes.

With regard to solvents which are suitable for carrying out step (c) of the method for preparing compounds having the formula (Ia), it is possible more particularly to mention acetone, acetonitrile, ethanol, isopropanol, methanol, methyl ethyl ketone, N,N-dimethylformamide (DMF), and dimethyl sulphoxide (DMSO).

Examples of a solvent which is particularly suitable for the method for preparing compounds having the formula (Ib) include in particular acetone and dichloromethane.

The derivatives which comprise a thiocarbonylsulphanyl function ($Z_1$—C(=S)—S—) and which can be used in step (c) include in particular xanthate compounds ($Z_1$=OR$^a$), dithiocarbamates ($Z_1$=NR$^b$R$^c$), trithiocarbonates ($Z_1$=$SR^a$). With regard to the groups $R^a$, $R^b$, and $R^c$, they comply with the definitions set out above.

$R^a$, $R^b$ and $R^c$ preferably represent an alkyl group, preferably an alkyl in $C_1$-$C_6$.

Preferred examples include xanthate derivatives, for example, potassium O-ethylxanthate.

Compounds having the formula (Ia), (Ib) and (Ic) can be separated and purified using conventional separation and purification techniques, for example, by means of filtration, concentration, extraction, crystallisation, recrystallisation, column chromatography or a combination of methods of this type.

Compounds having the formula (I), preferably compounds having the formula (Ia), have been found to be particularly advantageous in the context of radical organic synthesis reactions.

Under thermal, chemical or photochemical activation, preferably chemical or photochemical activation, compounds having the formula (I) result in $R^f$C.($Z_4$) (X) radicals.

They are preferably compounds having the formula (Ia) which result in Rf—C.($Z_4$)(NZ$_2$Z$_3$) radicals.

These radicals can then react with unsaturated compounds, such as olefins.

Activation is understood to be a process which allows the production of a radical Rf—C.($Z_4$)(X), preferably Rf—CO($Z_4$)(NZ$_2$Z$_3$) starting from a compound having the formula (I). This activation can be brought about in particular by the photons of an actinic source, in particular luminous source (photochemical activation), by the thermal decomposition of an initiator of free radicals, for example, a peroxide or a diazo compound (chemical activation), or by the autoxidation of a compound which is sensitive to oxygen, such as triethylborane.

Preferred examples of an initiator include peroxides, which are preferably symmetrical, and azo compounds. The peroxides include alkyl, and in particular tertioalkyl, peroxides, and acyl, in particular alkanoyl, peroxides which are preferably symmetrical.

The acyl peroxides which can be used are preferably peroxides whose acyls have a low molecular weight, that is to say, their number of carbon atoms is at the most equal to 10, preferably 6 when they are aliphatic, but it is preferable to use acyl peroxides of an aromatic nature, such as benzoyl peroxide.

Examples of an initiator of the peroxide type include in particular benzoyl peroxide, cumene hydroperoxide, hydrogen peroxide, acetyl peroxide and lauroyl peroxide.

Examples of initiators of the azo type (azobisnitrile) include in particular 2,2'-azobis-isobutyronitrile, 2,2'-azobis-(2-methyl-propanenitrile), 2,2'-azobis-(2,4-dimethylpentanenitrile), 2,2'-azobis-(2,4-dimethyl-4-methoxyvaleronitrile), 2',2'-azobis-(2,4-dimethylvalero-nitrile) and 2,2'-azobis-(2-amidinopropane) hydrochloride.

In this regard, reference can be made in particular to the work "Polymer Handbook", 4th edition, ed. D. Bloch.

Use of Compounds Having the Formula (I)

The use of compounds having the formula (I) in radical organic synthesis making use of this type of method constitutes another feature of the invention.

More precisely, compounds having the formula (I), including in particular compounds having the formula (Ia), are particularly useful in radical organic synthesis, as a source of Rf—C.($Z_4$)(X) radicals, including in particular (Rf—C.($Z_4$)(NZ$_2$Z$_3$)) radicals, which can be activated photochemically or chemically.

In this context, compounds having the formula (I), respectively (Ia), can be used to introduce an $R^f$($Z_4$)(X)C—, $R^f$($Z_4$)(NZ$_2$Z$_3$)C— group, respectively, in particular perfluoroalkylamine, in particular the radical 2,2,2-trifluoroethylamine, to an olefin.

Compounds having the formula (I) are used in particular to introduce one of the groups, (1a), (1b) or (1c) to an olefin:

(1a)

(1b)

(1c)

and in particular one of the groups (1'a), (1'b) or (1'c)

(1'a)

(1'b)

(1'c)

Method for Preparing Compounds Having the Formula (II)

According to another feature, the subject-matter of the invention is thus a method for preparing compounds having the formula (II):

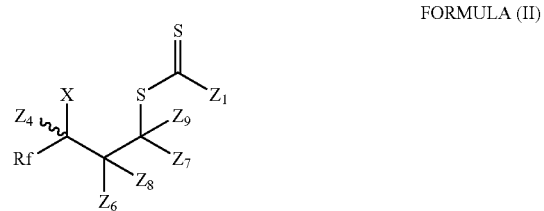

FORMULA (II)

in which

X, $Z_1$ and $Z_4$ have the above-mentioned definitions,

Rf represents
- (i) a halogen atom, preferably fluorine;
- (ii) halogenoalkyl, preferably fluoroalkyl, more preferably a perfluoroalkyl group ($C_nF_{2n+1}$);
- (iii) a poly- or per-halogenated aryl radical, or
- (iv) a radical selected from $R_4$—$CF_2$—, $R_4$—$CF_2$—$CF_2$—, $R_4$—$CF_2$—$CF(CF_3)$—, $CF_3$—$C(R_4)F$— and ($CF_3$)$R_4$—, with $R^4$ selected from an alkyl, acyl, aryl, aralkyl, alkene or alkyne group, cyclic hydrocarbons or heterocycles, $Z_6$, $Z_7$, $Z_8$ and $Z_9$ independently represent a hydrogen atom, a halogen atom, an alkyl, halogenoalkyl, alkenyl, alkynyl, acyl, aryl, arylalkyl, arylalkenyl, arylalkynyl group, or a cyclic hydrocarbon or a heterocycle, a polymer chain, a group —$(CH_2)_m$—$OR^k$, —$(CH_2)_m$—$CH(OR^k)(OR^l)$, $CH(OR^k)(OR^l)$—, —$(CH_2)_m$—$SR^k$, —$(CH_2)_m$—$SO_3R^k$, —$(CH_2)_m$—$NO_2$, —$(CH_2)_m$—$CN$, —$(CH_2)_m$—$R^k$, —[$(CH_2)_m$—$P(O)(OR^k)(OR^l)$], $(CH_2)_m$—$SiR^kR^lR^m$, —$(CH_2)_m$—$COOR^k$, —$(CH_2)_m$—$NCOR^k$, $(CH_2)_m$—$NR^kR^l$, in which:

$R^k$, $R^l$ and $R^m$ each independently refer to an alkyl, acyl, aryl, alkenyl, alkynyl, aralkyl, alkaryl, alkylsulphonyl, arylsulphonyl group, a cyclic hydrocarbon or a heterocycle, or $R^k$ and $R^l$ together form, with the atom to which they are attached, a cyclic hydrocarbon or a heterocycle;

m referring to a whole number which is greater than or equal to 1, preferably in the order of from 1 to 100, and advantageously from 1 to 20, and even more advantageously from 1 to 4, or $Z_6$, $Z_7$, $Z_8$ and $Z_9$ form, two by two, one or more cyclic hydrocarbon(s) or heterocycle(s), the groups $Z_6$, $Z_7$, $Z_8$ and $Z_9$ which do not form a ring being selected from the radicals mentioned above, the groups alkyl, halogenoalkyl, alkoxy, halogenoalkyl, alkenyl, alkynyl, acyl, ester, carbon cycle, aryl, arylalkyl, alkaryl, aralkenyl, aralkynyl, alkylsulphonyl, arylsulphonyl being as defined above, the method comprising the reaction of a compound having the formula (I) with at least one olefin having the formula (III):

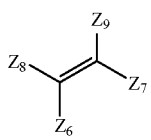

Formula (III)

in which $Z_6$, $Z_7$, $Z_8$ and $Z_9$ are as defined above, in the presence of a source of free radicals, in an organic solvent which is inert relative to radicals, and the recovery of the compound having the general formula (II).

X preferably represents —$NZ_2Z_3$, —$OZ_5$ or Hal, more preferably $NZ_2Z_3$, $Z_2$, $Z_3$, $Z_5$, and Hal having the above-mentioned definitions for the compounds having the formula (I).

The invention also relates to compounds having the formula (II) which are capable of being produced according to this method.

The compounds having the formula (II) are preferably compounds in which $X$=$NZ_2Z_3$, having the formula (IIa):

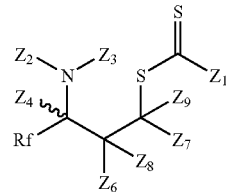

(IIa)

More precisely, the preparation of the compounds having the formula (II) consists in an addition of a radical of a compound having the formula (I) to an olefin having the formula (III).

The olefin having the formula (III) is preferably a monosubstituted olefin in which one of the groups $Z_6$, $Z_7$, $Z_8$ and $Z_9$ represents a substituent different from H, the others being H.

In a particularly advantageous manner, it has been shown that the group —S—C(=S)—$Z_1$ is generally selectively added to the carbon which carries a substituent which is different from H of the monosubstituted olefin.

"Selectively" is understood to be a level of selectivity preferably greater than 80%, more preferably greater than 90%, and even more advantageously greater than 95%.

Generally, the olefin used is introduced at the rate of from 1 to 3 equivalents relative to the compound having the formula (I).

Examples of cyclic hydrocarbons or heterocycles formed by two of the groups $Z_6$, $Z_7$, $Z_8$ or $Z_9$ include in particular the cycloalkyls, such as cyclopropane, or heterocycles, such as 1,3-dioxolane, 1,3-dioxolan-4-one.

—$(CH_2)_m$—$OR^k$ preferably represents a group —$(CH_2)_m$—$OCOAlk$, —$(CH_2)_m$—$O$—$CO$—$Ar$, —$(CH_2)_m$—$CO$-$Alk$ or —$(CH_2)_m$—$CO$—$Ar$.

Preferred examples include in particular the groups —$O$—$CO$—$CH_3$, —$CH_2$—$O$—$(CO)$—$CH_3$, —$(CH_2)_2$—$O$—$CO$—$CH_3$, —$(CH_2)_2$—$CO$—$CH_3$.

—$(CH_2)_m$—$CH(OR^k)(OR^l)$ preferably refers to a group —$(CH_2)_m$—$CH(OAlk_1)(OAlk_2)$ in which $Alk_1$ and $Alk_2$ are alkyl groups which are identical or different, as defined above. Examples include in particular —$CH_2$—$CH(OEt)_2$ and —$CH(OEt)_2$.

$(CH_2)_m$—$P(O)(OR^k)(OR^l)$ preferably refers to a group —$(CH_2)_m$—$P(O)(OAlk_1)(OAlk_2)$ in which $Alk_1$ and $Alk_2$ refer to an alkyl group as defined above. Examples include in particular —$CH_2$—$P(O)(OEt)_2$ and —$CH_2$—$P(O)(OMe)_2$.

—$(CH_2)_m$—$SiR^kR^lR^m$ preferably refers to a group —$(CH_2)_m$—$Si(Alk_1)(Alk_2)(Alk_3)$ in which $Alk_1$, $Alk_2$, $Alk_3$ refer to alkyl groups which are identical or different, as defined above. Examples include in particular —$CH_2$—$SiMe_3$.

—$(CH_2)_m$—$NR^kR^l$ preferably refers to a group in which $R^k$ and $R^l$ preferably independently represent a hydrogen atom, an alkyl, aryl, aralkyl, heteroaralkyl, alkylsulphonyl group, or form, with the atom of nitrogen to which they are attached, a heterocycle as defined above, preferably comprising from 4 to 8 carbon atoms.

When the heterocycle is saturated or partially saturated, it may comprise substituents of the type oxo (O=) or thioxo (S=).

Examples of a preferred $NR^kR^l$ group include in particular the N-arylalkylsulphonamide groups, such as N(4-bromophenyl)methane sulphonamide.

Examples of a heterocyclical —NR^k R^1 group include in particular the heterocycles pyrrolidin-2-one, isoindolyl-1,3-dione, phthalimide, aziridinyl, pyrrolidinyl, pyrazolidinyl, imidazolidinyl, piperidyl and piperazinyl.

According to one specific embodiment, the olefin having the formula (III) is a compound in which the groups $Z_6$, $Z_7$, $Z_8$ and $Z_9$ are selected from the following groups:
hydrogen,
—OAc,
—CH$_2$—OAc,
—(CH$_2$)$_2$—OAc,
—CH$_2$—SiMe$_3$,
—CH$_2$—CN,
—CH(OEt)$_2$, —CH$_2$—CH(OEt)$_2$,
—CH$_2$—P(O)(OEt)$_2$, —CH$_2$—P(O)(OMe)$_2$,
—(CH$_2$)$_2$—COMe,
pyrrolidin-2-one,
2-methyl-isoindole-1,3-dione,
(4-bromo-phenyl)-dimethylamine, or $Z_6$, $Z_7$, $Z_8$ and $Z_9$ together form, two by two, a 1,3-dioxol-2-one cycle, in which the symbol "Ac" represents an acetyl group, "Et" represents an ethyl group, and "Me" represents a methyl.

By way of non-limiting example, the olefin having the formula (III) which is used can be selected from the following compounds: vinyl acetate, hex-5-en-2-one, allyl acetate, vinyltrimethylsilane, but-3-enenitrile, 3,3-diethoxypropene, diethyl allylphosphonate.

The source of free radicals refers, in the context of the present description, to a source which is capable of activating compounds having the formula (I), and therefore bringing about the radical reaction. The compounds may be subjected to activation of a photo-chemical nature, in particular by means of exposure to light, or chemical nature, for example, by means of decomposition of a peroxide.

The activation preferably results from the decomposition of a chemical initiator, such as a peroxide or a diazo compound (thermal decomposition), or decomposition, by means of autoxidation with oxygen, of an organometallic compound, such as triethylborane, diethylzinc, trialkylaluminium.

Examples of peroxides which are particularly suitable as a source of free radicals in the method of the invention, thus include in particular diisobutyryl peroxide, cumyl peroxyneodecanoate, ter-amyl peroxyneodecanoate, di(2-ethylhexyl) peroxydicarbonate, tert-butyl peroxyneodecanoate, dibutyl peroxydicarbonate, dicetyl peroxydicarbonate, dimyristyl peroxydicarbonate, tert-butyl peroxyneoheptanoate, tert-amyl peroxypivalate, didecanoyl peroxide, tert-amyl peroxy-2-ethylhexanoate, tert-butyl peroxyisobutyrate, 1,4-di(tert-butylperoxycarbo)cyclohexane, tert-butyl peroxyacetate, tert-butyl peroxybenzoate, di-tert-amyl peroxide, tert-butyl cumyl peroxide, bis-tertiobutyl peroxide, dicumyl peroxide, dilauroyl peroxide or di(4-tert-butylcyclohexyl) peroxydicarbonate.

Regardless of its precise nature, the source of free radicals used according to the method of the invention is used in conditions which allow the production of free radicals, which is generally brought about by means of thermal activation, that is to say, by raising the temperature of the reaction medium which is generally at a temperature in the order of ambient temperature (approximately 20° C.) to 200° C., preferably from 40° C. to 180° C., advantageously from 80° C. to 160° C. The production of free radicals can also be carried out at a low temperature, generally at a temperature lower than ambient temperature, preferably from 100° C. to −78° C., by using free radical sources which are sensitive to the process of autoxidation with oxygen. Generally, the selection of the source of free radicals depends on the temperature at which it is desirable to carry out the reaction.

The quantity of the source of free radicals to be introduced into the medium is dependent on a number of parameters, including in particular the efficiency thereof, the method of introduction, the purity of the reagents, the concentration of the reaction medium, the efficiency of the olefin as a radical trap. The person skilled in the art would be capable of adjusting the quantity of the source of free radicals to be introduced into the medium in accordance with these various parameters. Generally, the source of free radicals used is introduced in a quantity such that the quantity of free radicals which it is capable of releasing is between 50% and 200% in moles, and preferably between 2% and 30% in moles, relative to the total molar quantity of thiocarbonylsulphanyl functions carried by the compounds having the formula (I) present in the medium.

The solvent used in the method for preparing compounds having the formula (II) is selected from the solvents conventionally used in radical synthesis, such as 1,2-dichloroethane, dichloromethane, benzene, toluene, trifluoromethylbenzene (trifluorotoluene), chlorobenzene, hexane, cyclohexane, heptane, octane, ethyl acetate, tert-butyl alcohol.

The reaction is generally carried out under atmospheric pressure, at the ebullition temperature of the selected solvent.

Compounds Having the Formula (II)

Compounds having the formula (II) produced by the method defined above are novel and also constitute subject-matter of the present invention.

Compounds having the formula (II) include in particular:
ester of S-[1-(2-acetylamino-3,3,3-trifluoro-propyl)-4-oxo-pentyl]dithiocarbonic acid O-ethyl ester,
ester of S-[5-(1-acetylamino-2,2,2-trifluoro-ethyl)-2-oxo-[1,3]dioxolan-4-yl]dithiocarbonic acid O-ethyl ester,
ester of 3-acetylamino-1-ethoxythiocarbonylsulphanyl-4,4,4-trifluoro-butyl acetic acid,
ester of S-(3-acetylamino-4,4,4-trifluoro-1-trimethyl-silanylmethyl-butyl) dithiocarbonic acid O-ethyl ester,
ester of S-(3-acetylamino-1-cyanomethyl-4,4,4-trifluoro-butyl) dithiocarbonic acid O-ethyl ester,
ester of S-(3-acetylamino-1-diethoxymethyl-4,4,4-trifluoro-butyl) dithiocarbonic acid O-ethyl ester,
ester of S-[3-acetylamino-1-(1,3-dioxo-1,3-dihydro-isoindol-2-ylmethyl)-4,4,4-trifluoro-butyl]dithiocarbonic acid O-ethyl ester,
ester of (4-acetylamino-2-ethoxythiocarbonylsulphanyl-5,5,5-trifluoro-pentyl) diethyl phosphonic acid,
ester of 4-acetylamino-2-ethoxythiocarbonylsulphanyl-5,5,5-trifluoro-pentyl acetic acid,
ester of S-[3-acetylamino-4,4,4-trifluoro-1-(2-oxo-pyrrolidin-1-yl)-butyl]dithiocarbonic acid O-ethyl ester,
ester of S-[3-acetylamino-1-{[(4-bromophenyl)-methanesulphonyl-amino]-methyl}-4,4,4-trifluoro-butyl) dithiocarbonic acid O-ethyl ester,
ester of S-[1-(2-acetylamino-3,3,3-trifluoro-propyl)-2-phenyl-cyclopropane]dithiocarbonic acid O-ethyl,
ester of 4-benzoylamino-2-ethoxythiocarbonylsulphanyl-5,5,5-trifluoro-butyl acetic acid,
4-tertbutyloxycarbamate-2-ethoxythiocarbonyl-sulphanyl-5,5,5-trifluoro-pentyl ester of acetic acid,
O-ethyl and S-(3-tertbutyloxycarbamate-1-diethoxy-methyl-4,4,4-trifluoro-butyl ester of dithiocarbonic acid,
O-ethyl and S-(3-tertbutyl-oxycarbamate-1-diethoxy-methyl-4,4,4-trifluoro-pentyl) diester of dithiocarbonic acid, O-ethyl and S-[3-acetoxy-1-(1,3-dioxo-1,3-dihydro-isoindol-2-ylmethyl)-4,4,4-trifluoro-butyl]diester of dithiocarbonic acid, O-ethyl and S-[3-acetoxy-4,4,4-trifluoro-1-trimethyl-silanylmethyl-butyl]diester of dithiocarbonic acid, 3-acetoxy-1-ethoxythiocarbonylsulphanyl-4,4,4-trifluorobutyl ester of acetic acid, O-ethyl and S-(3-acetoxy-1-diethoxymethyl-4,4,4-trifluoropentyl) diester of dithiocarbonic acid, O-ethyl and S-(3-acetoxy-1-cyanomethyl-4,4,4-trifluoro)butyl ester of dithiocarbonic acid, O-ethyl and S-1-(2-acetoxy-3,3,3-trifluoro-propyl)-4-oxopentyl diester of dithiocarbonic acid, 4-[4-bromo-phenyl)-methanesulphonyl-amino]-3-ethoxycarbonylsulphanyl-1-trifluoromethyl-butyl ester of acetic acid, O-ethyl and S-3-chloro-4,4,4-trifluoro-1-trimethylsilanylmethylbutyl diester of dithiocarbonic acid, 4-chloro-2-ethoxythiocarbonylsulphanyl-5,5,5-trifluoropentyl ester of acetic acid, O-ethyl and S-3-chloro-1-(1,3-dioxo-1,3-dihydro-isoindol-2-ylmethyl)-4,4,4-trifluoro-butyl ester of dithiocarbonic acid, O-ethyl and S-1-(2-chloro-3,3,3-trifluoro-propyl)-4-oxopentyl diester of dithiocarbonic acid, dimethyl and 4-chloro-2-ethoxythiocarbonyl-sulphanyl-5,5,5-trifluoro-pentyl ester of phosphonic acid, O-ethyl and S-3-chloro-1-cyanomethyl-4,4,4-trifluoro-butyl diester of diester of dithiocarbonic acid, O-ethyl and S-3-chloro-1-diethoxymethyl-4,4,4-trifluoropentyl dithiocarbonic acid, O-ethyl and S-3-chloro-1-(4-chloro-phenoxymethyl)-4,4,4-trifluoro-butyl diester of dithiocarbonic acid, O-ethyl and S-3-chloro-4,4,4-trifluoro-1-(2-oxo-pyrrolidin-1-yl)-butyl diester of dithiocarbonic acid.

Compounds having the formula (II) are particularly advantageous, particularly as an intermediate for organic synthesis, in particular in radical chemistry. In the same manner as the compounds having the formula (I), these compounds surprisingly have a high degree of reactivity, in particular in radical chemistry, in particular with respect to olefins and most particularly with respect to monosubstituted olefins.

Compounds having the formula (II) thus constitute key intermediates for the organic synthesis of functionalised compounds, such as α-perfluoroalkylamine derivatives, α-perfluoroalcohols or the halides of α-perfluoroalkyls, which are generally difficult to produce.

Methods for Converting Compounds Having the Formula (II)

The method for converting compounds having the formula (II) also constitutes subject-matter of the present invention.

In this case, the method according to the invention comprises the use of a compound having the formula (II) in one of the following reactions:
  reduction,
  removal,
  addition to an olefin,
  oxidation of the carbon which carries the thiocarbonylsulphanyl function in aldehyde, wherein these reactions result in the conversion or the displacement of the thiocarbonylsulphanyl function.

In the context of the present description, a "reduction" reaction is understood to be any reaction which involves the supply of electrons, by means of a reductive reagent which is rich in electrons, to the thiocarbonylsulphanyl function of the compound having the formula (II). This reaction results in the substitution of the thiocarbonylsulphanyl function by a hydrogen atom as illustrated in the general formula (IV):

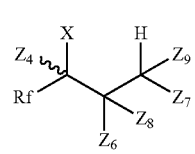

Formula (IV)

in which the groups $R^f$, X, $Z_4$, $Z_6$, $Z_7$, $Z_8$ and $Z_9$ have the above meaning for the compounds having the formula (II).

Compounds having the formula (IV) are particularly preferred, in which X=—$NZ_2Z_3$ where $Z_2$ and $Z_3$ have the above meaning.

The "removal" reaction, in the sense in which it is used in the present description, refers to a reaction resulting from two consecutive or concerted departures of two entities of a different nature, that is to say, a proton $H^+$ brought about by the attack of a base, on the one hand, and the departure of the anion $^-S(CS)Z_1$ brought about by the adjacent carbanion (in the α-position). This reaction leads to the production of a product which comprises a double bond between the carbon which initially carries the thiocarbonylsulphanyl function and the carbon in the α-position, complying with the general formula (V):

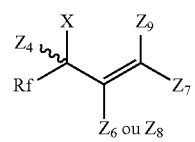

Formula (V)

The method for preparing compounds having the formula (IV) according to the invention therefore comprises the use of a compound having the formula (II) in which the groups X, $Z_4$, $Z_6$, $Z_7$, $Z_8$ and $Z_9$ and Rf have the above meaning, it being understood that at least one of the groups $Z_6$ and $Z_8$ represents a hydrogen atom, with a base.

Examples of a base include in particular tetrabutylammonium fluoride.

X preferably represents $NZ_2Z_3$ where $Z_2$ and $Z_3$ have the above meaning.

A "radical addition" reaction of a compound (II) to an olefin $Z_{10}Z_{11}(C=C)Z_{12}Z_{13}$, in the presence of a source of free radicals, complying with the definitions set out above, leads to the production of a compound which complies with the general formula (VI):

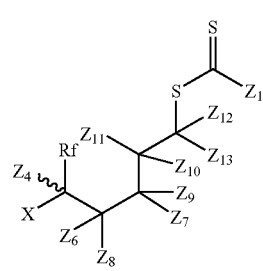

Formula (VI)

In which $R^f$, X, $Z_4$, $Z_6$, $Z_7$, $Z_8$ and $Z_9$ are as defined above and $Z_{10}$, $Z_{11}$, $Z_{12}$ and $Z_{13}$ comply with the definitions given above for $Z_6$, $Z_7$, $Z_8$ and $Z_9$.

"Oxidation of the carbon which carries the thiocarbonylsulphanyl function in aldehyde" is understood to be any reaction, in the presence of an organic or mineral acid, of a compound having the formula (II) in which $Z_7$, $Z_9$ each represent an acyloxy-radical and a hydrogen atom, resulting in compounds having the general formula (VII):

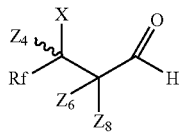

Formula (VII)

in which Rf, X, $Z_4$, $Z_6$ and $Z_8$ are as defined above.

X preferably represents —$NZ_2Z_3$ where $Z_2$ and $Z_3$ have the above meaning.

The aldehyde (VII) produced in the form of an acetal is also included within the concept of the invention.

By way of illustration of compounds produced using one of the methods for converting the above compounds having the formula (II), it is possible to mention in particular:

N-[3-(2-oxo-pyrrolidin-1-yl)-1-trifluoromethyl-allyl]acetamide,
N-[4-(1,3-dioxo-1,3-dihydro-isoindol-2-yl)-1-trifluoromethyl-butyl]acetamide,
ester of S-{1-[5-(1-acetylamino-2,2,2-trifluoro-ethyl)-2-oxo-[1,3]dioxolan-4-ylmethyl]-2,2-diethoxy-ethyl}dithiocarbonic acid O-ethyl ester,
N-[1-(5-bromo-1-methanesulphonyl-2,3-dihydro-1H-indol-3-ylmethyl)-2,2,2-trifluoro-ethyl]-acetamide,
N-(3,3-dimethoxy-1-trifluoromethyl-propyl)-acetamide,
4-acetyl-5,5,5-trifluoro-pent-1-ene,
ester of 1-[5-bromo-1-methanesulphonyl-2,3-dihydro-1H-indol-3-ylmethyl)-2,2,2-trifluoro-ethyl]acetic acid,
1-(3-chloro-4,4,4-trifluoro-but-1-enyl)-pyrrolidin-2-one,
2-(4-chloro-5,5,5-trifluoro-pentyl)-isoindole-1,3-dione.

Method for Preparing Compounds Having the Formula (VIII)

Following photochemical or chemical activation in the absence of reactive compounds, compounds having the formula (I) may lead to the formation of a compound having the general formula (VIII):

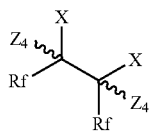

FORMULA (VIII)

in which X and $Z_4$ are as defined above, and Rf represents:
(i) a fluorine atom;
(ii) fluoroalkyl, more preferably perfluoroalkyl;
(iii) a poly- or per-halogenated aryl radical, or
(iv) a radical selected from $R_A$—$CF_2$, $R_A$—$CF_2$—$CF_2$—, $R_A$—$CF_2$—$CF(CF_3)$—, $CF_3$—$C(R_A)F$— and $(CF_3)R_A$—, with $R^A$ selected from an alkyl, acyl, aryl, aralkyl, alkene or alkyne group, cyclic hydrocarbons or heterocycles.

X preferably represents —$NZ_2Z_3$ or —$OZ_5$, more preferably —$NZ_2Z_3$, $Z_2$, $Z_3$ and $Z_5$ being as defined previously.

By way of illustration of preferred compounds having the formula (VII), it is possible to mention in particular an ester of 2-benzoxy-3,3,3-trifluoro-1-trifluoromethyl-propyl benzoic acid and N-(2-acetylamino-3,3,3-trifluoro-methylpropyl)acetamide.

The method for preparing compounds of this type having the formula (VIII) constitutes, according to another feature, subject-matter of the invention.

More precisely, the method according to the invention comprises a step for radical dimerisation of a compound having the general formula (I) and a step for recovering the compound having the formula (VIII).

In the context of the present invention, radical dimerisation is understood to be the formation of a carbon-carbon bond between two identical $(X)(Rf)(Z_4)C$. radicals.

This reaction comprises the use of a compound having the formula (I), preferably (Ia) or (Ib), with a source of free radicals.

In this context, it is particularly preferable for at least one of the groups $Z_2$ and $Z_3$ to represent an acyl group.

$Z_5$ preferably represents an acyl group, including aroyl, more preferably a benzoyl group.

With regard to the temperature and pressure conditions as well as the nature of the solvent and the source of free radicals which are particularly suitable for the radical dimerisation method according to the invention, they comply with the definitions set out above for the method for preparing compounds having the formula (II).

The compound (VIII) is generally produced in this context by means of dimerisation of the radical originating from the compound (I) with itself, in the presence of an at least stoichiometric quantity of a source of free radicals.

As has been emphasised above, one advantage of the compounds (I) according to the invention is that they have a high degree of reactivity in radical synthesis, in particular with respect to olefins.

These compounds have been found to be particularly advantageous in this context for introducing an $(X)(Rf)(Z_4)$C— group, in particular to a large variety of functional or non-functional olefins.

Another advantage is that the method for preparing compounds having the formula (II) constitutes a particularly flexible method for producing α-perfluoroalkylamine derivatives. The thiocarbonylsulphanyl function ($Z_1$—C(=S)—S—) present on the compound (II) can be readily reduced, removed, or even bring about a plurality of consecutive radical reactions. The resultant products can thus represent a particularly advantageous network for leading to complex trifluoromethylated structures.

Generally, the base products and reagents used in the methods for preparing compounds having the formula (I), (II) and (VII) are inexpensive.

Furthermore, the method for preparing compounds having the formula (II) according to the invention advantageously requires neutral experimental conditions and is therefore compatible with a large number of chemical functions which can be present on the olefin partner.

In a particularly advantageous manner, compounds having the formula (II) in the context of the invention provide convergent and rapid access to processed structures which contain a great variety of functions.

Finally, the presence of the thiocarbonylsulphanyl group, in particular a xanthate group, on the formed product (II) advantageously provides access to the extremely rich chemistry of sulphur (via thiols, sulphides, sulphones, sulphonic acids, sulphonamides, sulphonium salts, the ylides of sulphur, etc . . . ).

The following examples are given by way of non-limiting illustration of the present invention.

EXAMPLES

Example of Method for Preparing Compounds Having the Formula (Ia)

Example 1

Preparation of S-[1-(N-acetylamino)-2,2,2-trifluoroethyl]-O-ethyl dithiocarbonate a) N-(2,2,2-trifluoro-1-hydroxy-ethyl)-acetamide

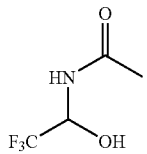

$C_4H_6F_3NO_2$
M = 157.09 g.mol$^{-1}$

Reaction:
A solution of 2,2,2-trifluoro-1-methoxy-ethanol (6.50 g, 50 mmol) and acetamide (2.95 g, 50 mmol) in 75 ml of 1,4-dioxane is brought to reflux for one hour. After returning to ambient temperature, the reaction admixture is concentrated at reduced pressure before being purified.

Purification:
Chromatography over silica gel (ethyl acetate-petroleum ether 4/6).
Product:
White crystalline.
Yield:
65%
MP (° C.)
117-119 (ethyl acetate-heptane)

b) N-(1-chloro-2,2,2-trifluoro-ethyl)-acetamide

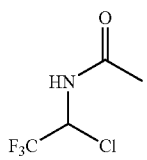

$C_4H_5ClF_3NO$
M = 175.54 g.mol$^{-1}$

Reaction:
A solution of alcohol a (2.00 g, 12.73 mmol) and phosphorus pentachloride (3.05 g, 14.64 mmol) is agitated at ambient temperature for 30 minutes, then at 70° C. for 15 minutes. After evaporation at reduced pressure, the residue is purified.
Purification
Crystallisation.
Product:
White crystalline.
Yield:
59%

MP (° C.)
78-81 (petroleum ether)
$^1$HNMR (δ, ppm) (CDCl$_3$, 400 MHz)
2.14 (s, 3H, COCH$_3$); 6.34 (qd, J=5.3 Hz, 11.1 Hz, 1H, CF$_3$CH); 6.47 (d, J=10.0 Hz, 1H, NH).
IR (ν, cm$^{-1}$)(CCl$_4$)
3436 (NH); 3315 (NH); 2995; 1726 (C=O); 1497; 1370; 1345; 1282; 1253; 1221; 1203; 1140.

c) Ester of dithiocarbonic acid S-(1-acetylamino-2,2,2-trifluoro-ethyl) O-ethyl ester

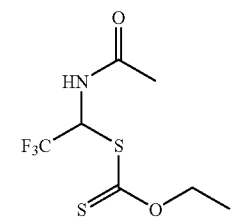

$C_7H_{10}F_3NO_2S_2$
M = 261.29 g.mol$^{-1}$

Reaction:
The salt of potassium ethylxanthogenate (208 mg, 1.29 mmol) is added to a solution of the chlorinated compound b (208 mg, 1.18 mmol) in 5 ml of acetone. After 15 minutes at ambient temperature, the reaction admixture is concentrated at reduced pressure. The residue is placed in ether, filtered and concentrated once more at reduced pressure.

Purification:
Chromatography over silica gel (ethyl acetate-petroleum ether 2/8).
Product:
White crystalline.
Yield:
100%
$^1$HNMR (δ, ppm) (CDCl$_3$, 400 MHz)
1.44 (t, J=7.0 Hz, 3H, CH$_2$CH$_3$); 2.09 (s, 3H, COCH$_3$); 4.69 (q, J=7.0 Hz, 2H, CH$_3$CH$_2$); 6.59 (qd, J=7.6 Hz, 10.0 Hz, 1H, CF$_3$CH); 6.89 (d, J=10.0 Hz, 1H, NH).
$^{13}$CNMR (δ, ppm) (CDCl$_3$, 100 MHz)
13.68 (CH$_3$CH$_2$); 22.96 (CH$_3$CO); 57.83 (q, J=38 Hz, CF$_3$CH); 71.42 (CH$_2$CH$_3$); 123.48 (q, J=280 Hz, CF$_3$); 169.63 (C=O); 206.87 (C=S).
IR (ν, cm$^{-1}$)(CCl$_4$)
3441 (NH); 2983; 1714 (C=O); 1489; 1368; 1331; 1270; 1234; 1196; 1122; 1047.
MP (° C.)
84-86 (ethyl acetate-heptane)
Mass (IC, NH$_3$)
262 (MH$^+$), 279 (MNH$_4^+$).

| | | Element: | |
|---|---|---|---|
| | | Carbon | Hydrogen |
| Microanalysis | Calculated (%) | 32.18 | 3.86 |
| | Actual (found) (%) | 32.57 | 3.91 |

Example 2

Preparation of O-ethyl and [[S-1-benzoyl-amino-2,2,2-trifluoro-ethyl]]S-1-tert-butyloxycarbonyl-amino-2,2,2-trifluoro-ethyl diester of dithiocarbonic acid a) N-(2,2,2-trifluoro-1-hydroxy-ethyl)tert-butylcarbamate

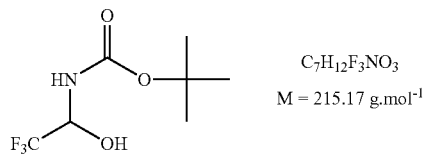

$C_7H_{12}F_3NO_3$
M = 215.17 g.mol$^{-1}$

Reaction:

A solution of 2,2,2-trifluoro-1-methoxy-ethanol (1.63 g, 12.5 mmol) and tert-butylcarbamate (1.46 g, 12.5 mmol) in 1,4-dioxane (20 ml) is brought to reflux for one hour. After returning to ambient temperature, the reaction admixture is concentrated at reduced pressure before being purified.

Purification:

Chromatography over silica gel (ethyl acetate-petroleum ether 4/6).

Product:

White crystals.

Yield:

55%.

MP

118° C. (ethyl acetate-heptane)

b) N-(1-chloro-2,2,2-trifluoro-ethyl)-tertbutylcarbamate

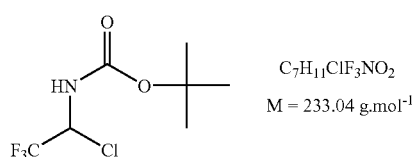

$C_7H_{11}ClF_3NO_2$
M = 233.04 g.mol$^{-1}$

Reaction:

Thionyl chloride (85 µL, 1.16 mmol) and pyridine (95 µL, 1.4 mmol) are added to a solution of alcohol A8 (250 mg, 1.16 mmol) in dichloromethane (10 ml). After 1.5 hours under reflux, the reaction admixture is cooled and concentrated at reduced pressure.

Product:

Yellow crystals.

Yield:

61%

MP

125° C. (ethyl acetate-heptane)

c) O-ethyl and S-1-tert-butyloxycarbonylamino-2,2,2-trifluoro-ethyl diester of dithiocarbonic acid

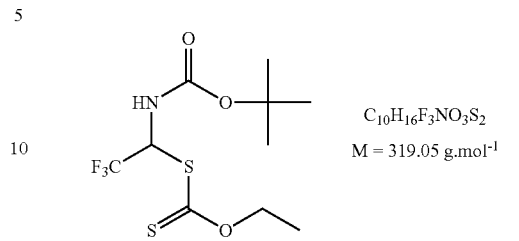

$C_{10}H_{16}F_3NO_3S_2$
M = 319.05 g.mol$^{-1}$

Reaction:

The salt of potassium ethylxanthogenate (230 mg, 1.42 mmol) is added to a solution of the chlorinated compound A10 (165 mg, 0.71 mmol) in acetone (8 ml). After 30 min at ambient temperature, the reaction admixture is concentrated at reduced pressure. The residue is placed in ether, filtered and once more concentrated at reduced pressure.

Purification:

Chromatography over silica gel (ethyl acetate-petroleum ether 2/98).

Product:

White crystals.

Yield:

100%

$^1$HNMR (δ, ppm) (CDCl$_3$, 400 MHz)

1.52 (s, 9H, 3×CH$_3$); 1.64 (t, J=6.8 Hz, 3H, CH$_2$CH$_3$); 4.69 (m, 2H, CH$_3$CH$_2$); 5.21 (d, J=10.0 Hz, 1H, NH); 6.32 (m, 1H, CF$_3$CH).

$^{13}$CNMR (δ, ppm) (CDCl$_3$, 100 MHz)

13.6 (CH$_3$CH$_2$); 28.1 (3×CH$_3$); 57.8 (q, J=38 Hz, CF$_3$CH); 69.5 (C(CH$_3$)$_3$); 71.4 (CH$_2$CH$_3$); 120.4 (q, J=278 Hz, CF$_3$); 167.6 (C=O); 205.6 (C=S).

IR (ν, cm$^{-1}$) (CCl$_4$)

3441 (NH); 2983; 2358; 1737 (C=O); 1489; 1368; 1335; 1236; 1193; 1153; 1123; 1048.

MP

80° C. (ethyl acetate-heptane)

Mass (IC, NH3)

320 (MH$^+$), 337 (MNH$_4^+$).

|  |  | Element | |
|---|---|---|---|
|  |  | Carbon | Hydrogen |
| Microanalysis: | Calculated (%) | 37.61 | 5.05 |
|  | Actual (%) | 37.42 | 5.23 |

Radical Additions

General Operating Method:

A solution of xanthate (n mmol) and olefin (2n mmol) in 1,2-dichloroethane (2n ml) is brought to reflux under argon for a few minutes before lauroyl peroxide (LP) is added at a rate of from 2 to 5 mol %/n every 90 minutes. Once the starting xanthate is completely consumed, the reaction medium is brought to ambient temperature then concentrated at reduced pressure before being purified.

Method for Preparing Compounds Having the Formula (IIA)

Radical Additions

Example 3

Ester of S-[1-(2-acetylamino-3,3,3-trifluoro-propyl)-4-oxo-pentyl]dithiocarbonic acid O-ethyl ester

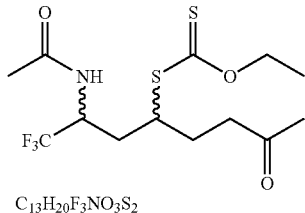

$C_{13}H_{20}F_3NO_3S_2$ $M = 359.43$ g.mol$^{-1}$

Reaction:
Carried out according to the general operating method with 160 mg (0.61 mmol) of xanthate of example 1 and 142 µl (1.23 mmol) of hex-5-en-2-one in 2 ml of 1,2-dichloroethane. The reaction is terminated after the addition of 5% of LP and 1 hour 30 minutes under reflux.

Purification:
Chromatography over silica gel (ethyl acetate-petroleum ether 1/1).

Product:
Pale yellow oil.

Yield:
88% (2 diastereoisomers at a ratio of 1/1)

$^1$HNMR (δ, ppm) (CDCl$_3$, 400 MHz)
1.37 (t, J=7.0 Hz, 3H, CH$_2$CH$_3$); 1.39 (t, J=7.0 Hz, 3H, CH$_2$CH$_3$); 1.67-1.86 (m, 2H); 1.90-2.16 (m, 6H); 1.98 (s, 3H, COCH$_3$); 2.10 (s, 3H, COCH$_3$); 2.11 (s, 3H, COCH$_3$); 2.12 (s, 3H, COCH$_3$); 2.51-2.70 (m, 4H); 3.64 (m, 1H, CHS); 3.87 (m, 1H, CHS); 4.58 (q, J=7.0 Hz, 2H, CH$_3$CH$_2$); 4.61 (q, J=7.0 Hz, 2H, CH$_3$CH$_2$); 4.75 (m, 1H, CF$_3$CH); 4.81 (m, 1H, CF$_3$CH); 6.35 (d, J=9.4 Hz, 1H, NH); 6.57 (d, J=10.0 Hz, 1H, NH).

$^{13}$CNMR (δ, ppm) (CDCl$_3$, 100 MHz)
13.78 (2 CH$_3$CH$_2$); 23.07 (2 CH$_3$CON); 25.59 (CH$_2$); 29.16 (CH$_2$); 29.97 (CH$_3$CO); 30.06 (CH$_3$CO); 32.74 (CH$_2$); 34.19 (CH$_2$); 40.24 (CH$_2$); 40.61 (CH$_2$); 46.51 (CHS); 47.07 (CHS); 48.33 (q, J=32 Hz, CF$_3$CH); 48.56 (q, J=30 Hz, CF$_3$CH); 70.49 (CH$_2$CH$_3$); 70.65 (CH$_2$CH$_3$); 124.88 (q, J=281 Hz, CF$_3$); 125.10 (q, J=281 Hz, CF$_3$); 170.39 (NC=O); 170.77 (NC=O); 207.32 (C=O); 208.15 (C=O); 213.69 (C=S); 214.09 (C=S).

IR (ν, cm$^{-1}$)
3442 (NH); 2983; 1714 (C=O); 1703 (C=O); 1504; 1443; 1369; (CCl$_4$) 1238; 1185; 1133; 1112; 1050.

Mass (IC, NH$_3$)
360 (MH$^+$), 377 (MNH$_4{}^+$).

|  |  | Element: | |
|---|---|---|---|
|  |  | Carbon | Hydrogen |
| Microanalysis | Calculated (%) | 43.44 | 5.61 |
|  | Actual (%) | 43.65 | 5.77 |

Example 4

Ester of S-[5-(1-acetylamino-2,2,2-trifluoro-ethyl)-2-oxo-[1,3]dioxolan-4-yl]dithiocarbonic acid O-ethyl ester Reaction:
Carried out according to the general operating method with 200 mg (0.77 mmol) of xanthate of example 1 and 200 mg (2.31 mmol) of 1,3-dioxol-2-one in 1.5 ml of 1,2-dichloroethane. The reaction is terminated after the addition of 20% of LP and 6 hours under reflux.

Purification:
Chromatography over silica gel (ether-petroleum ether 4/6 to 6/4).

Product:

First Diastereoisomer:
Rf (ether-petroleum ether 6/4)=0.30, pale yellow oil which slowly crystallises over a period of time.

Second Diastereoisomer:
Rf (ether-petroleum ether 6/4)=0.16, colourless crystalline.

Yield:
72% (2 diastereoisomers at a ratio of 1/1)

First Diastereoisomer
$^1$HNMR (δ, ppm) (CDCl$_3$, 400 MHz)
1.46 (t, J=7.0 Hz, 3H, CH$_2$CH$_3$); 2.16 (s, 3H, COCH$_3$); 4.69 (q, J=7.0 Hz, 2H, CH$_3$CH$_2$); 5.12 (d, J=5.3 Hz, 1H, CF$_3$CH(NAc)CH); 5.17 (qd, J=7.6 Hz, 10.0 Hz, 1H, CF$_3$CH); 6.04 (d, J=5.3 Hz, 1H, CHS); 7.38 (d, J=10.0 Hz, 1H, NH).

$^{13}$CNMR (δ, ppm) (CDCl$_3$, 100 MHz)
13.56 (CH$_3$CH$_2$); 22.61 (CH$_3$CO); 51.18 (q, J=29 Hz, CF$_3$CH); 71.55 (CH$_2$CH$_3$); 77.68 (CF$_3$CH(NAc)CH); 83.55 (CHS); 123.16 (q, J=283 Hz, CF$_3$); 152.95 (OC=O); 171.92 (NC=O); 205.72 (C=S).

IR (ν, cm$^{-1}$) (CCl$_4$)
3432 (NH); 3343 (NH); 2959; 1842; 1816 (C=O); 1741 (C=O); 1709; 1500; 1709; 1500; 1371; 1273; 1236; 1192; 1141; 1047.

Mass (IC, NH$_3$)
348 (MH$^+$); 365 (MNH$_4{}^+$).

|  |  | Element: | |
|---|---|---|---|
|  |  | Carbon | Hydrogen |
| Microanalysis | Calculated (%) | 34.58 | 3.48 |
|  | Actual (%) | 34.28 | 3.47 |

Second Diastereoisomer
$^1$HNMR (δ, ppm) (CDCl$_3$, 400 MHz)
1.48 (t, J=7.0 Hz, 3H, CH$_2$CH$_3$); 2.13 (s, 3H, COCH$_3$); 4.72 (q, J=7.0 Hz, 2H, CH$_3$CH$_2$); 4.85 (dd, J=5.3 Hz, 5.3 Hz, 1H, CF$_3$CH(NAc)CH); 5.19 (qdd, J=7.6 Hz, 5.3 Hz, 10.0 Hz, 1H, CF$_3$CH); 6.06 (d, J=10.0 Hz, 1H, NH); 6.35 (d, J=5.3 Hz, 1H, CHS).

$^{13}$CNMR (δ, ppm) (CD$_3$OD, 100 MHz)
13.86 (CH$_3$CH$_2$); 22.40 (CH$_3$CO); 52.86 (q, J=30 Hz, CF$_3$CH); 72.75 (CH$_2$CH$_3$); 77.29 (CF$_3$CH(NAc)CH); 85.58 (CHS); 125.03 (q, J=283 Hz, CF$_3$); 153.75 (OC=O); 173.66 (NC=O); 208.71 (C=S).

IR (ν, cm$^{-1}$)(CCl$_4$)
3258 (NH); 3064 (NH); 2985; 1818 (C=O); 1686; 1549; 1442; 1360; 1298; 1255; 1135; 1076; 1047.

Mass (IC, NH$_3$)
348 (MH$^+$); 365 (MNH$_4{}^+$).

|   |   | Element: | |
|---|---|---|---|
|   |   | Carbon | Hydrogen |
| Microanalysis | Calculated (%) | 34.58 | 3.48 |
|   | Actual (%) | 34.81 | 3.44 |

Example 5

Ester of 3-acetylamino-1-ethoxythiocarbonylsulphanyl-4,4,4-trifluoro-butyl acetic acid

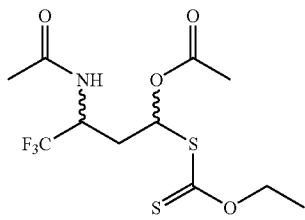

$C_{11}H_{16}F_3NO_4S_2$

M = 347.38 g.mol$^{-1}$

Reaction:
Carried out according to the general operating method with 200 mg (0.77 mmol) of xanthate of example 1 and 85 µL (0.92 mmol) of vinyl acetate in 1.5 ml of 1,2-dichloroethane. The reaction is terminated after the addition of 2.5% of LP and 1 hour 30 minutes under reflux.

Purification:
Chromatography over silica gel (ethyl acetate-petroleum ether 2/8 to 3/7).

Product:
Thick pale yellow oil which crystallises over a period of time

Yield:
95% (2 diastereoisomers at a ratio of 4/6)

$^1$H NMR (δ, ppm) (CDCl$_3$, 400 MHz)
1.38 (t, J=7.6 Hz, 3H, CH$_2$CH$_3$); 1.39 (t, J=7.0 Hz, 3H, CH$_2$CH$_3$); 2.03 (s, 6H, COCH$_3$); 2.06 (s, 3H, COCH$_3$); 2.07 (s, 3H, COCH$_3$); 2.12-2.22 (m, 2H, CF$_3$CH(NAc)CH$_2$); 2.38-2.51 (m, 2H, CF$_3$CH(NAc)CH$_2$); 4.60 (q, J=7.0 Hz, 2H, CH$_3$CH$_2$); 4.61 (q, J=7.6 Hz, 2H, CH$_3$CH$_2$); 4.70-4.83 (m, 2H, CF$_3$CH); 6.53 (dd, J=10.0 Hz, 2.9 Hz, 1H, CHS); 6.62 (d, J=9.4 Hz, 1H, NH); 6.64 (dd, J=8.2 Hz, 4.7 Hz, 1H, CHS); 6.78 (d, J=10.0 Hz, 1H, NH).

$^{13}$CNMR (δ, ppm) (CDCl$_3$, 100 MHz)
13.60 (CH$_3$CH$_2$); 20.66 (CH$_3$CO); 20.77 (CH$_3$CO); 22.80 (CH$_3$CO); 22.96 (CH$_3$CO); 32.66 (CH$_2$CHS); 33.33 (CH$_2$CHS); 47.36 (q, J=32 Hz, CF$_3$CH); 47.65 (q, J=32 Hz, CF$_3$CH); 70.45 (CH$_2$CH$_3$); 70.73 (CH$_2$CH$_3$); 76.00 (CHS); 78.30 (CHS); 124.63 (q, J=281 Hz, CF$_3$); 124.71 (q, J=281 Hz, CF$_3$); 168.95 (C=O); 169.67 (C=O); 170.48 (C=O); 170.72 (C=O); 209.33 (C=S); 209.86 (C=S).

IR (ν, cm$^{-1}$)(CCl$_4$)
3429 (NH); 2982; 1767 (C=O); 1706 (C=O); 1503; 1369; 1235; 1188; 1137; 1049.

Mass (IC, NH$_3$)
288 (M-AcOH+H$^+$); 348 (MH$^+$); 365 (MNH$_4^+$).

|   |   | Element: | |
|---|---|---|---|
|   |   | Carbon | Hydrogen |
| Microanalysis | Calculated (%) | 38.03 | 4.64 |
|   | Actual (%) | 37.79 | 4.51 |

Example 6

Ester of S-(3-acetylamino-4,4,4-trifluoro-1-trimethylsilanylmethyl-butyl) dithiocarbonic acid O-ethyl ester

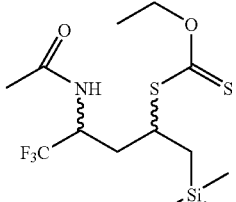

$C_{13}H_{24}F_3NO_2S_2Si$

M = 375.55 g.mol$^{-1}$

Reaction:
Carried out according to the general operating method with 200 mg (0.77 mmol) of xanthate of example 1 and 364 µl (2.29 mmol) of allyl-trimethyl-silane in 1.5 ml of 1,2-dichloroethane. The reaction is terminated after the addition of 5% of LP and 1 hour under reflux.

Purification:
Chromatograpy over silica gel (ethyl acetate-petroleum ether 1/9 to 2/8).

Product:

First Diastereoisomer:
Rf (ethyl acetate-petroleum ether 1/9)=0.38, colourless crystalline solid.

Second Diastereoisomer:
Rf (ethyl acetate-petroleum ether 1/9)=0.19, colourless crystalline solid.

Yield:
95% (2 diastereoisomers at a ratio of 40/60)

First Diastereoisomer (Majority)
$^1$HNMR (δ, ppm) (CDCl$_3$, 400 MHz)
0.03 (s, 9H, Si(CH$_3$)$_3$); 0.85-1.16 (m, 2H, CH$_2$Si(CH$_3$)$_3$); 1.42 (t, J=7.0 Hz, 3H, CH$_2$CH$_3$); 1.93-2.16 (m, 2H, CF$_3$CH(NAc)CH$_2$); 2.11 (s, 3H, COCH$_3$); 3.64 (m, 1H, CHS); 4.63 (q, J=7.0 Hz, 2H, CH$_3$CH$_2$); 4.71 (m, 1H, CF$_3$CH); 6.00 (d, J=9.4 Hz, 1H, NH).

$^{13}$CNMR (δ, ppm) (CDCl$_3$, 100 MHz)
−0.82 (Si(CH$_3$)$_3$); 13.87 (CH$_3$CH$_2$); 19.48 (CH$_2$); 23.12 (CH$_3$CO); 37.37 (CH$_2$); 43.79 (CHS); 48.44 (q, J=32 Hz, CF$_3$CH); 70.29 (CH$_2$CH$_3$); 124.99 (q, J=281 Hz, CF$_3$); 170.34 (NC=O); 215.11 (C=S).

IR (ν, cm$^{-1}$) (CCl$_4$)
3432 (NH); 2956; 1701 (C=O); 1507; 1250; 1218; 1184; 1130; 1112; 1051.

Mass (IC, NH$_3$)
254 (M-HSCSOEt+H+); 376 (MH$^+$); 393 (MNH$_4^+$).

|  | Element: | |
|---|---|---|
|  | Carbon | Hydrogen |
| Microanalysis Calculated (%) | 41.58 | 6.44 |
| Actual (%) | 41.48 | 6.41 |

Second Diastereoisomer (Minority)

$^1$HNMR (δ, ppm) (CDCl$_3$, 400 MHz)

0.07 (s, 9H, Si(CH$_3$)$_3$); 1.04-1.19 (m, 2H, CH$_2$Si(CH$_3$)$_3$); 1.40 (t, J=7.0 Hz, 3H, CH$_2$CH$_3$); 1.94-2.21 (m, 2H, CF$_3$CH(NAc)CH$_2$); 2.03 (s, 3H, COCH$_3$); 4.02 (m, 1H, CHS); 4.63 (q, J=7.0 Hz, 2H, CH$_3$CH$_2$); 4.84 (m, 1H, CF$_3$CH); 6.03 (d, J=10.0 Hz, 1H, NH).

$^{13}$CNMR (δ, ppm) (CDCl$_3$, 100 MHz)

−0.68 (Si(CH$_3$)$_3$); 13.86 (CH$_3$CH$_2$); 23.18 (CH$_2$); 23.26 (CH$_3$CO); 35.07 (CH$_2$); 44.98 (CHS); 48.50 (q, J=28 Hz, CF$_3$CH); 70.11 (CH$_2$CH$_3$); 125.13 (q, J=281 Hz, CF$_3$); 170.09 (NC=O); 213.53 (C=S).

IR (ν, cm$^{-1}$) (CCl$_4$)

3441 (NH); 2955; 1704 (C=O); 1441; 1367; 1251; 1217; 1183; 1129; 1112; 1048.

Mass (IC, NH$_3$)

254 (M-HSCSOEt+H$^+$); 376 (MH$^+$); 393 (MNH$_4^+$).

|  | Element: | |
|---|---|---|
|  | Carbon | Hydrogen |
| Microanalysis Calculated (%) | 41.58 | 6.44 |
| Actual (%) | 41.49 | 6.45 |

Example 7

Ester of S-(3-acetylamino-1-cyanomethyl-4,4,4-trifluoro-butyl) dithiocarbonic acid O-ethyl ester

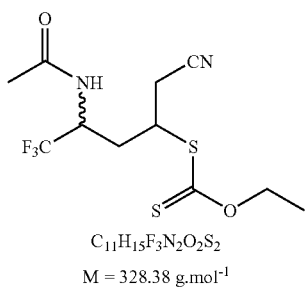

C$_{11}$H$_{15}$F$_3$N$_2$O$_2$S$_2$

M = 328.38 g.mol$^{-1}$

Reaction:

Carried out according to the general operating method with 200 mg (0.77 mmol) of xanthate of example 1 and 184 μL (2.29 mmol) of but-3-enenitrile in 1.5 ml of 1,2-dichloroethane. The reaction is terminated after the addition of 15% of LP and 4 hours 30 minutes under reflux.

Purification:

Chromatography over silica gel (ethyl acetate-petroleum ether 3/7).

Product:

Thick pale yellow oil.

Yield:

87% (2 diastereoisomers at a ratio of 4/6).

$^1$HNMR (δ, ppm) (CDCl$_3$, 400 MHz)

1.39 (t, J=7.0 Hz, 3H, CH$_2$CH$_3$); 1.40 (t, J=7.0 Hz, 3H, CH$_2$CH$_3$); 1.99 (s, 3H, COCH$_3$); 2.06 (s, 3H, COCH$_3$); 2.02-2.31 (m, 4H, CF$_3$CH(NAc)CH$_2$); 2.82-3.02 (m, 4H, CH$_2$CN); 3.92 (m, 1H, CHS); 4.01 (m, 1H, CHS); 4.61 (q, J=7.0 Hz, 2H, CH$_3$CH$_2$); 4.63 (q, J=7.0 Hz, 2H, CH$_3$CH$_2$); 4.73 (m, 1H, CF$_3$CH); 4.82 (m, 1H, CF$_3$CH); 6.90 (d, J=10.0 Hz, 1H, NH); 7.01 (d, J=9.4 Hz, 1H, NH).

$^{13}$CNMR (δ, ppm) (CDCl$_3$, 100 MHz)

13.66 (CH$_3$CH$_2$); 22.28 (CH$_2$); 22.79 (CH$_3$CO); 24.21 (CH$_2$); 30.40 (CH$_2$); 31.39 (CH$_2$); 42.48 (CHS); 43.11 (CHS); 48.20 (q, J=30 Hz, CF$_3$CH); 48.27 (q, J=30 Hz, CF$_3$CH); 70.98 (CH$_2$CH$_3$); 71.14 (CH$_2$CH$_3$); 116.53 (CN); 116.90 (CN); 124.52 (q, J=281 Hz, CF$_3$); 124.71 (q, J=281 Hz, CF$_3$); 170.93 (C=O); 171.24 (C=O); 211.24 (C=S); 211.34 (C=S).

IR (ν, cm$^{-1}$) (CCl$_4$)

3438 (NH); 2984; 1701 (C=O); 1505; 1442; 1369; 1237; 1191; 1139; 1112; 1049.

Mass (IC, NH$_3$)

329 (MH$^+$); 346 (MNH$_4^+$).

|  | Element: | |
|---|---|---|
|  | Carbon | Hydrogen |
| Microanalysis Calculated (%) | 40.23 | 4.60 |
| Actual (%) | 40.39 | 4.53 |

Example 8

Ester of S-(3-acetylamino-1-diethoxymethyl-4,4,4-trifluoro-butyl) dithiocarbonic acid O-ethyl ester

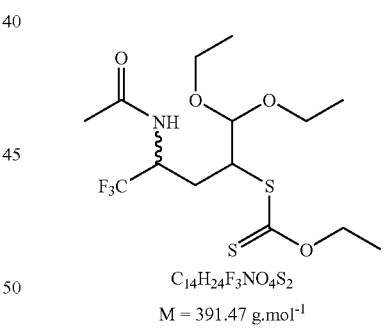

C$_{14}$H$_{24}$F$_3$NO$_4$S$_2$

M = 391.47 g.mol$^{-1}$

Reaction:

Carried out according to the general operating method with 200 mg (0.77 mmol) of xanthate of example 1 and 351 μL (2.29 mmol) of 3,3-diethoxy-propene in 1.5 ml of 1,2-dichloroethane. The reaction is terminated after the addition of 5% of LP and 1 hour 30 minutes under reflux.

Purification:

Chromatography over silica gel (ethyl acetate-petroleum ether 3/7).

Product:

Thick pale yellow oil.

Yield:

95% (2 diastereoisomers at a ratio of 1/1).

$^1$HNMR (δ, ppm) (CDCl$_3$, 400 MHz)

1.16 (t, J=7.0 Hz, 3H, CH$_2$CH$_3$); 1.17 (t, J=7.0 Hz, 3H, CH$_2$CH$_3$); 1.20 (t, J=7.0 Hz, 3H, CH$_2$CH$_3$); 1.21 (t, J=7.0 Hz, 3H, CH$_2$CH$_3$); 1.38 (t, J=7.0 Hz, 6H, CH$_2$CH$_3$); 1.80-2.19 (m, 3H, CF$_3$CH(NAc)CH$_2$); 1.98 (s, 3H, COCH$_3$); 2.05 (s, 3H, COCH$_3$); 2.49 (m, 1H, CF$_3$CH(NAc)CH$_2$); 3.43-3.76 (m, 8H, CH$_3$CH$_2$); 3.95-4.05 (m, 2H, CHS); 4.52 (d, J=3.0 Hz, 1H, CH(OEt)$_2$); 4.59 (d, J=3.0 Hz, 1H, CH(OEt)$_2$); 4.61 (q, J=7.0 Hz, 4H, CH$_3$CH$_2$); 4.73-4.91 (m, 2H, CF$_3$CH); 6.19 (d, J=9.4 Hz, 1H, NH); 6.31 (d, J=9.4 Hz, 1H, NH).

$^{13}$CNMR (δ, ppm) (CDCl$_3$, 100 MHz)

13.78 (2×CH$_3$CH$_2$); 15.08 (2×CH$_3$CH$_2$); 15.15 (CH$_3$CH$_2$); 15.34 (CH$_3$CH$_2$); 23.04 (CH$_3$CO); 23.13 (CH$_3$CO); 25.80 (CH$_2$CHS); 28.46 (CH$_2$CHS); 48.42 (q, J=30 Hz, CF$_3$CH); 49.08 (q, J=30 Hz, CF$_3$CH); 49.88 (CHS); 50.44 (CHS); 64.09 (CH$_2$CH$_3$); 64.31 (CH$_2$CH$_3$); 64.76 (CH$_2$CH$_3$); 65.54 (CH$_2$CH$_3$); 70.54 (CH$_2$CH$_3$); 70.63 (CH$_2$CH$_3$); 102.75 (CH(OEt)$_2$); 103.95 (CH(OEt)$_2$); 124.94 (q, J=281 Hz, CF$_3$); 125.17 (q, J=283 Hz, CF$_3$); 170.14 (C=O); 171.32 (C=O); 213.91 (C=S); 214.79 (C=S).

IR (ν, cm$^{-1}$) (CCl$_4$)

3443 (NH); 2979; 2930; 2875; 1741 (C=O); 1703 (C=O); 1508; 1443; 1370; 1341; 1284; 1218; 1185; 1135; 1112; 1054.

Mass (IC, NH$_3$)

346 (M-EtOH+H$^+$).

Example 9

Ester of S-[3-acetylamino-1-(1,3-dioxo-1,3-dihydro-isoindol-2-ylmethyl)-4,4,4-trifluoro-butyl]dithiocarbonic acid O-ethyl ester

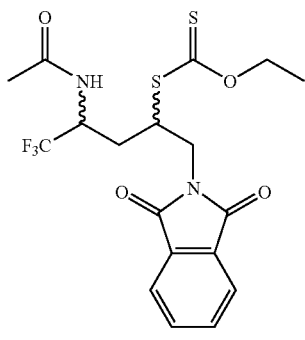

C$_{18}$H$_{19}$F$_3$N$_2$O$_4$S$_2$

M = 448.48 g.mol$^{-1}$

Reaction:

Carried out according to the general operating method with 200 mg (0.77 mmol) of xanthate of example 1 and 286 mg (1.53 mmol) of allyl phthalimide in 1.5 ml of 1,2-dichloroethane. The reaction is terminated after the addition of 10% of LP and 3 hours under reflux.

Purification:

Chromatography over silica gel (ethyl acetate-petroleum ether 4/6).

Product:

Colourless crystalline.

Yield:

77% (2 diastereoisomers at a ratio of 6/4)

$^1$H NMR (δ, ppm) (CDCl$_3$, 400 MHz)

1.33 (t, J=7.0 Hz, 3H, CH$_2$CH$_3$); 1.37 (t, J=7.0 Hz, 3H, CH$_2$CH$_3$); 2.02-2.24 (m, 4H, CF$_3$CH(NAc)CH$_2$); 2.02 (s, 3H, COCH$_3$); 2.19 (s, 3H, COCH$_3$); 3.93-4.06 (m, 4H, CH$_2$N); 4.16-4.23 (m, 1H, CHS); 4.23-4.30 (m, 1H, CHS); 4.51 (q, J=7.0 Hz, 2H, CH$_3$CH$_2$); 4.57 (q, J=7.0 Hz, 2H, CH$_3$CH$_2$); 4.90-5.11 (m, 2H, CF$_3$CH); 6.44 (d, J=10.0 Hz, 1H, NH); 6.53 (d, J=10.0 Hz, 1H, NH); 7.70-7.73 (m, 4H, H$_{Ar}$); 7.79-7.84 (m, 4H, H$_{Ar}$).

$^{13}$CNMR (δ, ppm) (CDCl$_3$, 100 MHz)

13.62 (CH$_3$CH$_2$); 13.71 (CH$_3$CH$_2$); 23.13 (CH$_3$CO); 23.19 (CH$_3$CO); 23.96 (CF$_3$CH(NAc)CH$_2$); 30.42 (CF$_3$CH(NAc)CH$_2$); 39.03 (CH$_2$N); 41.56 (CH$_2$N); 45.89 (CHS); 46.34 (CHS); 48.24 (q, J=31 Hz, CF$_3$CH); 48.62 (q, J=31 Hz, CF$_3$CH); 70.68 (CH$_2$CH$_3$); 70.71 (CH$_2$CH$_3$); 123.52 (CH$_{Ar}$); 123.61 (CH$_{Ar}$); 124.85 (q, J=279 Hz, CF$_3$); 124.99 (q, J=280 Hz, CF$_3$); 131.67 (Cq$_{Ar}$); 131.72 (Cq$_{Ar}$); 134.36 (2×CH$_{Ar}$); 168.17 (2×C=O$_{Ar}$); 168.24 (2×C=O$_{Ar}$); 170.34 (C=O); 170.75 (C=O); 211.9 (C=S); 212.75 (C=S).

IR (ν, cm$^{-1}$) (CCl$_4$)

3441 (NH); 2983; 1776 (C=O); 1722 (C=O); 1504; 1468; 1441; 1392; 1366; 1227; 1187; 1134; 1112; 1050.

Mass (IC, NH$_3$)

449 (MH$^+$); 366 (MNH$_4$$^+$).

|  |  | Element: | |
|---|---|---|---|
|  |  | Carbon | Hydrogen |
| Microanalysis | Calculated (%) | 48.21 | 4.27 |
|  | Actual (%) | 48.61 | 4.42 |

Example 10

Ester of diethyl (4-acetylamino-2-ethoxythiocarbonylsulphanyl-5,5,5-trifluoro-pentyl) phosphonic acid

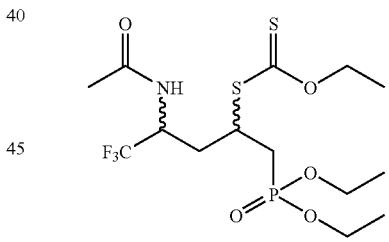

C$_{14}$H$_{25}$F$_3$NO$_5$PS$_2$

M = 439.45 g.mol$^{-1}$

Reaction:

Carried out according to the general operating method with 200 mg (0.77 mmol) of xanthate of example 1 and 407 mg (2.29 mmol) of diethyl allylphosphonic acid ester in 1.5 ml of 1,2-dichloroethane. The reaction is terminated after the addition of 5% of LP and 1 hour 30 minutes under reflux.

Purification:

Chromatography over silica gel (dichloromethane-methanol 99/1).

Product:

Pale yellow oil.

Yield:

86% (2 diastereoisomers at a ratio of 6/4)

$^1$HNMR (δ, ppm) (CDCl$_3$, 400 MHz)

1.29 (t, J=7.6 Hz, 6H, CH$_2$CH$_3$); 1.30 (t, J=7.0 Hz, 6H, CH$_2$CH$_3$); 1.25 (t, J=7.0 Hz, 3H, CH$_2$CH$_3$); 1.36 (t, J=7.0 Hz, 3H, CH$_2$CH$_3$); 1.99 (s, 3H, COCH$_3$); 2.02 (s, 3H, COCH$_3$); 2.06-2.45 (m, 8H, CH$_2$P+CF$_3$CH(NAc)CH$_2$); 3.92-4.16 (m, 10H, CH$_3$CH$_2$+CHS); 4.53-4.61 (m, 4H, CH$_3$CH$_2$); 4.65-4.79 (m, 2H, CF$_3$CH); 7.05 (d, J=8.8 Hz, 1H, NH); 7.10 (d, J=9.4 Hz, 1H, NH).

$^{13}$CNMR (δ, ppm) (CDCl$_3$, 100 MHz)
13.68 (2×CH$_3$CH$_2$); 16.34 (m, CH$_3$CH$_2$OP); 22.90 (2×CH$_3$CO); 29.02 (d, J=138 Hz, CH$_2$P); 31.26 (CF$_3$CH (NAc)CH$_2$); 31.45 (CF$_3$CH(NAc)CH$_2$); 31.75 (d, J=135 Hz, CH$_2$P); 41.52 (CHS); 42.09 (CHS); 48.37 (q, J=30 Hz, CF$_3$CH); 48.68 (q, J=30 Hz, CF$_3$CH); 62.21 (m, CH$_3$CH$_2$OP); 70.35 (2×CH$_2$CH$_3$); 124.85 (2×q, J=281 Hz, CF$_3$); 170.51 (C=O); 170.67 (C=O); 212.20 (C=S); 212.87 (C=S).

IR (ν, cm$^{-1}$) (CCl$_4$)
3309 (NH); 2983; 1699 (C=O); 1532; 1442; 1390; 1368; 1291; 1227; 1186; 1135; 1112; 1048; 1028.

Mass (IC, NH$_3$)
318 (M-HSCSOEt+H$^+$); 440 (MH$^+$); 457 (MNH$_4^+$).

|  |  | Element: | |
|---|---|---|---|
|  |  | Carbon | Hydrogen |
| Microanalysis | Calculated (%) | 38.26 | 5.73 |
|  | Actual (%) | 38.01 | 5.81 |

Example 11

Ester of 4-acetylamino-2-ethoxythiocarbonylsulphanyl-5,5,5-trifluoro-pentyl acetic acid

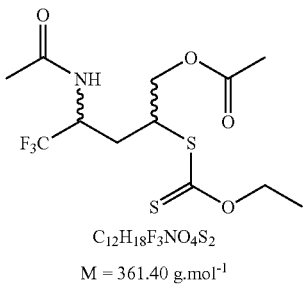

C$_{12}$H$_{18}$F$_3$NO$_4$S$_2$

M = 361.40 g.mol$^{-1}$

Reaction:
Carried out according to the general operating method with 200 mg (0.77 mmol) of xanthate of example 1 and 247 μL (3 mmol) of allyl acetate in 1.5 ml of 1,2-dichloroethane. The reaction is terminated after the addition of 5% of LP and 1 hour 30 minutes under reflux.

Purification:
Chromatography over silica gel (ethyl acetate-petroleum ether 3/7).

Product:
Pale yellow oil.

Yield:
84% (2 diastereoisomers at a ratio of 1/1).

$^1$HNMR (δ, ppm) (CDCl$_3$, 400 MHz)
1.38 (t, J=7.0 Hz, 3H, CH$_2$CH$_3$); 1.40 (t, J=7.0 Hz, 3H, CH$_2$CH$_3$); 1.89-2.15 (m, 3H, CF$_3$CH(NAc)CH$_2$); 1.99 (s, 3H, COCH$_3$); 2.06 (s, 3H, COCH$_3$); 2.07 (s, 3H, COCH$_3$); 2.08 (s, 3H, COCH$_3$); 2.20-2.27 (m, 3H, CF$_3$CH(NAc)CH$_2$); 3.92-3.98 (m, 1H, CHS); 4.09-4.15 (m, 1H, CHS); 4.24-4.41 (m, 4H, CH$_2$OCOCH$_3$); 4.60 (q, J=7.0 Hz, 2H, CH$_3$CH$_2$); 4.62 (q, J=7.0 Hz, 2H, CH$_3$CH$_2$); 4.72-4.91 (m, 2H, CF$_3$CH); 6.50 (d, J=9.4 Hz, 1H, NH); 6.64 (d, J=9.4 Hz, 1H, NH).

$^{13}$CNMR (δ, ppm) (CDCl$_3$, 100 MHz)
13.71 (CH$_3$CH$_2$); 13.73 (CH$_3$CH$_2$); 20.69 (CH$_3$CO); 20.78 (CH$_3$CO); 22.97 (CH$_3$CO); 22.99 (CH$_3$CO); 29.04 (CF$_3$CH(NAc)CH$_2$); 30.12 (CF$_3$CH(NAc)CH$_2$); 45.62 (CHS); 46.00 (CHS); 48.36 (q, J=30 Hz, CF$_3$CH); 48.49 (q, J=30 Hz, CF$_3$CH); 63.98 (CH$_2$OCOCH$_3$); 65.94 (CH$_2$OCOCH$_3$); 70.71 (CH$_2$CH$_3$); 70.83 (CH$_2$CH$_3$); 124.75 (q, J=281 Hz, CF$_3$); 124.99 (q, J=281 Hz, CF$_3$); 170.49 (C=O); 170.64 (C=O); 170.75 (C=O); 170.86 (C=O); 212.39 (C=S); 212.94 (C=S).

IR (ν, cm$^{-1}$)(CCl$_4$)
3442 (NH); 2984; 1752 (C=O); 1703 (C=O); 1506; 1442; 1381; 1367; 1340; 1227; 1186; 1137; 1112; 1052.

Mass (IC, NH$_3$)
302 (M-HOAc+H$^+$); 362 (MH$^+$); 379 (MNH$_4^+$).

|  |  | Element: | |
|---|---|---|---|
|  |  | Carbon | Hydrogen |
| Microanalysis | Calculated (%) | 39.88 | 5.02 |
|  | Actual (%) | 40.08 | 5.07 |

Example 12

Ester of S-[3-acetylamino-4,4,4-trifluoro-1-(2-oxo-pyrrolidin-1-yl)-butyl]dithiocarbonic acid O-ethyl ester

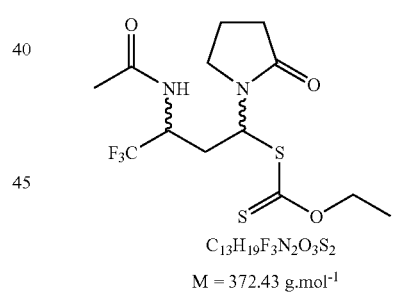

C$_{13}$H$_{19}$F$_3$N$_2$O$_3$S$_2$

M = 372.43 g.mol$^{-1}$

Reaction:
Carried out according to the general operating method with 200 mg (0.77 mmol) of xanthate of example 1 and 104 μL (mmol) of vinyl-pyrrolidin-2-one in 1.5 ml of 1,2-dichloroethane. The reaction is terminated after the addition of 10% of LP and 3 hours under reflux.

Purification:
Chromatography over silica gel (dichloromethane-methanol 98/2).

Product:
Unstable pale yellow oil which leads to the enamide of example 13.

Yield:
62% (2 diastereoisomeres at a ratio of 4/6) 21% of the enamide of example 13

$^1$HNMR (δ, ppm) (CDCl$_3$, 400 MHz)

1.41 (t, J=7.0 Hz, 3H, CH$_2$CH$_3$); 1.42 (t, J=7.0 Hz, 3H, CH$_2$CH$_3$); 2.02-2.26 (m, 7H, CH$_2$CO+CF$_3$CH(NAc)CH$_2$); 2.07 (s, 3H, COCH$_3$); 2.09 (s, 3H, COCH$_3$); 2.35-2.42 (m, 4H, CH$_2$CH$_2$CH$_2$); 2.60-2.67 (m, 1H, CF$_3$CH(NAc)CH$_2$); 3.41-3.57 (m, 4H, CH$_2$N); 4.50-4.62 (m, 1H, CF$_3$CH); 4.64 (q, J=7.0 Hz, 2H, CH$_3$CH$_2$); 4.65 (q, J=7.0 Hz, 2H, CH$_3$CH$_2$); 4.74-4.86 (m, 1H, CF$_3$CH); 5.90 (dd, J=12.3 Hz, 4.1 Hz, 1H, CHS); 6.02 (dd, J=8.2 Hz, 7.6 Hz, 1H, CHS); 6.69 (d, J=10.0 Hz, 1H, NH); 7.29 (d, J=10.0 Hz, 1H, NH).

$^{13}$CNMR (δ, ppm) (CDCl$_3$, 100 MHz)

13.68 (CH$_3$CH$_2$); 13.76 (CH$_3$CH$_2$); 18.00 (CH$_2$CH$_2$CH$_2$); 18.15 (CH$_2$CH$_2$CH$_2$); 22.94 (CH$_3$CO); 23.02 (CH$_3$CO); 30.66 (CH$_2$CO); 30.84 (CH$_2$CO); 31.06 (CF$_3$CH(NAc)CH$_2$); 31.25 (CF$_3$CH(NAc)CH$_2$); 44.95 (CH$_2$N); 45.24 (CH$_2$N); 47.49 (q, J=30 Hz, CF$_3$CH); 48.08 (q, J=32 Hz, CF$_3$CH); 58.33 (CHS); 58.98 (CHS); 70.62 (CH$_2$CH$_3$); 70.71 (CH$_2$CH$_3$); 124.75 (q, J=281 Hz, CF$_3$); 124.82 (q, J=282 Hz, CF$_3$); 170.54 (C=O); 170.86 (C=O); 175.52 (C=O); 175.57 (C=O); 210.06 (C=S); 211.76 (C=S).

IR (ν, cm$^{-1}$) (CCl$_4$)

3439 (NH); 3298 (NH); 2984; 1703 (C=O); 1501; 1416; 1368; 1286; 1265; 1226; 1183; 1132; 1111; 1049.

Mass (IC, NH$_3$)

251 (M-HSCSOEt+H$^+$); 268 (M-HSCSOEt+NH$_4$$^+$); 373 (MH$^+$); 390 (MNH$_4$$^+$).

Example 13

Ester of S-[3-acetylamino-1-{[(4-bromo-phenyl)-methanesulphonyl-amino]-methyl}-4,4,4-trifluoro-butyl]dithiocarbonic acid O-ethyl ester C$_{17}$H$_{22}$BrF$_3$N$_2$O$_4$S$_3$ M = 551.463 g.mol$^{-1}$ Reaction:
Carried out according to the general operating method with 261 mg (1 mmol) of xanthate of example 1 and 580 mg (2 mmol) of N-allyl-N-(4-bromo-phenyl)-methanesulphonamide in 2 ml of 1,2-dichloroethane. The reaction is terminated after the addition of 20% of LP and 7 hours under reflux.

Purification:
Chromatography over silica gel (ethyl acetate-petroleum ether 4/6).

Product:
White foam.

Yield:
77% (2 diastereoisomers at a ratio of 1/1)

$^1$HNMR (δ, ppm) (CDCl$_3$, 400 MHz)

1.29 (t, J=7.0 Hz, 3H, CH$_2$CH$_3$); 1.33 (t, J=7.0 Hz, 3H, CH$_2$CH$_3$); 1.86 (s, 3H, COCH$_3$); 1.90-2.04 (m, 2H, CF$_3$CH(NAc)CH$_2$); 1.94 (s, 3H, COCH$_3$); 2.19-2.30 (m, 2H, CF$_3$CH(NAc)CH$_2$); 2.83 (s, 6H, SO$_2$CH$_3$); 3.56-3.70 (m, 2H, CHS); 3.81-3.96 (m, 4H, CH$_2$N); 4.44-4.57 (m, 4H, CH$_3$CH$_2$); 4.70-4.83 (m, 2H, CF$_3$CH); 6.50 (d, J=9.4 Hz, 1H, NH); 6.67 (d, J=9.4 Hz, 1H, NH); 7.20 (d, J=8.2 Hz, 2H, H$_{Ar}$(HC=CNSO$_2$)); 7.30 (d, J=8.2 Hz, 2H, H$_{Ar}$(HC=CNSO$_2$)); 7.51 (d, J=8.2 Hz, 2H, H$_{Ar}$(HC=CBr)); 7.54 (d, J=8.2 Hz, 2H, HA, (HC=CBr)).

$^{13}$CNMR (δ, ppm) (CDCl$_3$, 100 MHz)

13.53 (CH$_3$CH$_2$); 13.61 (CH$_3$CH$_2$); 22.64 (CH$_3$CO); 22.75 (CH$_3$CO); 28.18 (CF$_3$CH(NAc)CH$_2$); 29.52 (CF$_3$CH(NAc) CH$_2$); 36.70 (CH$_3$SO$_2$); 36.97 (CH$_3$SO$_2$); 44.84 (CHS); 45.67 (CHS); 48.03 (q, J=32 Hz, 2×CF$_3$CH); 51.40 (CH$_2$N); 53.37 (CH$_2$N); 70.61 (2×CH$_2$CH$_3$); 122.64 (2×Cq$_{Ar}$Br); 124.64 (q, J=281 Hz, CF$_3$); 124.79 (q, J=281 Hz, CF$_3$); 130.32 (CH$_{Ar}$); 130.43 (CH$_{Ar}$); 132.73 (2×CH$_{Ar}$); 137.14 (Cq$_{Ar}$NSO$_2$); 137.31 (Cq$_{Ar}$NSO$_2$); 170.43 (C=O); 170.72 (C=O); 211.49 (C=S); 212.54 (C=S).

IR (ν, cm$^{-1}$) (CCl$_4$)

3437 (NH); 2984; 1700 (C=O); 1488; 1442; 1358; 1227; 1187; 1162; 1140; 1112; 1050; 1012.

Mass (IC, NH$_3$)

552 (MH$^+$); 569 (MNH$_4$$^+$).

|  |  | Element: | |
|---|---|---|---|
|  |  | Carbon | Hydrogen |
| Microanalysis | Calculated (%) | 37.03 | 4.02 |
|  | Actual (%) | 37.06 | 4.11 |

Example 14

Ester dithiocarbonic acid S-[1-(2-acetylamino-3,3,3-trifluoro-propyl)-2-phenyl-cyclopropane]O-ethyl

C$_{17}$H$_{20}$F$_3$NO$_5$S$_2$

M = 391.48 g.mol$^{-1}$

Reaction:
Carried out according to the general operating method with 131 mg (0.50 mmol) of xanthate of example 1 and 130 mg (1.00 mmol) of 1-methylen-2-phenylcyclopropane in 1,2-dichloroethane (2 ml). The reaction is terminated after the addition of 10% of LP (20 mg) and 3 hours under reflux.

Purification:
Chromatography over silica gel (ether-petroleum ether 3/7).

Product:

First Diastereoisomer:
Rf (ether-petroleum ether 3/7)=0.20, pale yellow oil which crystallises slowly.

Second Diastereoisomer:
Rf (ether-petroleum ether 3/7)=0.16, pale yellow oil.

Yield:
68% (2 diastereoisomers at a ratio of 3/1)

First Diastereoisomer (Majority):

$^1$HNMR (δ, ppm) (CDCl$_3$, 400 MHz)

1.46 (t, J=5.0 Hz, 3H, CH$_2$CH$_3$); 1.86 (s, 3H, COCH$_3$); 2.05 (d, J=7.0 Hz, 2H, CH$_2$CHC$_{Ar}$); 1.86-2.16 (m, 2H,

CH$_2$CHCF$_3$); 2.71 (dd, J$_1$=8.0 Hz, J$_2$=0.8 Hz, 1H, CHC$_{Ar.}$); 4.59-4.64 (m, 2H, CH$_3$CH$_2$); 4.64-4.68 (m, 1H, CHCF$_3$); 5.06 (d, J=9.4 Hz, 1H, NH); 7.20-7.50 (m, 5H, H$_{Ar.}$).

$^{13}$CNMR (δ, ppm) (CDCl$_3$, 100 MHz)

13.6 (CH$_3$CH$_2$); 16.6 (CH$_3$CO); 21.9 (CH$_2$CHCF$_3$); 28.8 (CH$_2$CHC$_{Ar.}$); 31.1 (CHC$_{Ar.}$); 32.8 (Cq$_{cyclo}$); 49.9 (q, J=29 Hz, CF$_3$CH); 70.1 (OCH$_2$CH$_3$); 124.2 (CF$_3$); 129.6 (2×CH$_{Ar.}$); 130.0 (2×CH$_{Ar.}$); 130.8 (CH$_{Ar.}$); 138.4 (Cq$_{Ar.}$); 170.9 (NC=O); 212.7 (C=S).

IR (ν, cm$^{-1}$)(CCl$_4$)

3432 (NH); 2927; 1702 (C=O); 1498; 1225; 1224 (C=S); 1221; 1124; 1051.

Mass (IC, NH3)

392 (MH$^+$); 409 (MNH$_4^+$).

|  |  | Element: | |
|---|---|---|---|
|  |  | Carbon | Hydrogen |
| Microanalysis | Calculated (%) | 52.16 | 5.15 |
|  | Actual (%) | 52.25 | 5.08 |

MP

137° C. (ethyl acetate-heptane)

Second Diastereoisomer (Minority)

$^1$HNMR (δ, ppm) (CDCl$_3$, 400 MHz)

1.36 (t, J=5.0 Hz, 3H, CH$_2$CH$_3$); 1.96 (s, 3H, COCH$_3$); 2.45 (d, J=12.0 Hz, 2H, CH$_2$CHC$_{Ar.}$); 1.96-2.43 (m, 2H, CH$_2$CHCF$_3$); 2.83 (dd, J$_1$=5.7 Hz, J$_2$=0.8 Hz, 1H, CHC$_{Ar.}$); 4.64-4.69 (m, 2H, CH$_3$CH$_2$); 4.89-4.98 (m, 1H, CHCF$_3$); 6.25 (d, J=11.4 Hz, 1H, NH); 7.10-7.50 (m, 5H, H$_{Ar.}$).

$^{13}$CNMR (δ, ppm) (CD$_3$OD, 100 MHz)

13.9 (CH$_3$CH$_2$); 16.7 (CH$_3$CO); 32.5 (Cq$_{cyclo}$); 31.1 (CHC$_{Ar.}$) 28.6 (CH$_2$CHC$_{Ar.}$); 21.9 (CH$_2$CHCF$_3$); 49.6 (q, J=29 Hz, CF$_3$CH); 70.2 (OCH$_2$CH$_3$); 124.1 (CF$_3$); 129.5 (2×CH$_{Ar.}$); 129.9 (2×CH$_{Ar.}$); 130.3 (CH$_{Ar.}$); 138.3 (Cq$_{Ar.}$); 170.5 (NC=O); 212.8 (C=S).

IR (ν, cm$^{-1}$) (CCl$_4$)

3432 (NH); 2927; 1702 (C=O); 1498; 1225; 1224 (C=S); 1221; 1124; 1051.

Mass (IC, NH3)

392 (MH$^+$); 409 (MNH$_4^+$).

Example 15

Ester of 4-benzoylamino-2-ethoxythio-carbonyl-sulphanyl-5,5,5-trifluoro-butyl acetic acid

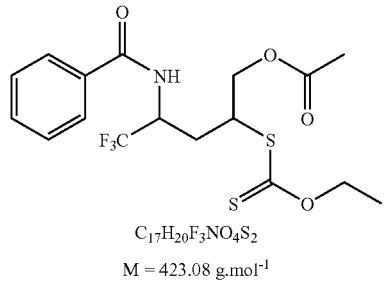

C$_{17}$H$_{20}$F$_3$NO$_4$S$_2$

M = 423.08 g.mol$^{-1}$

Reaction:

Carried out according to the general operating method with 500 mg (1.55 mmol) of xanthate S-(1-benzoylamino-2,2,2-trifluoro-ethyl) ester dithiocarbonic acid O-ethyl ester [operating method of the xanthate to be provided] and 333 μL (3 mmol) of allyl acetate in 1,2-dichloroethane (3 ml). The reaction is terminated after the addition of 10% of LP (62 mg) and 1 hour 30 minutes under reflux.

Purification:

Chromatography over silica gel (ether-petroleum ether 3/7).

Product:

Pale yellow oil.

Yield:

84% (admixture of 2 diastereoisomers at a ratio of 1/1).

$^1$HNMR (δ, ppm) (CDCl$_3$, 400 MHz)

1.32 (t, J=7.0 Hz, 1.5H, CH$_2$CH$_3$); 1.38 (t, J=7.0 Hz, 1.5H, CH$_2$CH$_3$); 1.89-2.15 (m, 1H, CF$_3$CHNCH$_2$); 1.99 (s, 1.5H, COCH$_3$); 2.06 (s, 1.5H, COCH$_3$); 2.20-2.27 (m, 1H, CF$_3$CHNCH$_2$); 3.92-3.98 (m, 0.5H, CHS); 4.09-4.15 (m, 0.5H, CHS); 4.24-4.41 (m, 2H, CH$_2$OCOCH$_3$); 4.52 (q, J=6.1 Hz, 1H, CH$_3$CH$_2$); 4.54 (q, J=5.0 Hz, 1H, CH$_3$CH$_2$); 4.98-5.12 (m, 1H, CF$_3$CH); 6.20 (d, J=8.7 Hz, 0.5H, NH); 6.54 (d, J=8.9 Hz, 0.5H, NM); 7.31-7.92 (m, 5H, CH$_{Ar.}$).

$^{13}$CNMR (δ, ppm) (CDCl$_3$, 100 MHz)

13.7 (CH$_3$CH$_2$); 22.9 (CH$_3$CO); 29.0 (0.5×CF$_3$CHCH$_2$); 30.1 (0.5×CF$_3$CHCH$_2$); 45.6 (0.5×CHS); 46.0 (0.5×CHS); 48.3 (q, J=30 Hz, 0.5×CF$_3$CH); 48.4 (q, J=30 Hz, 0.5×CF$_3$CH); 63.9 (0.5×CH$_2$OCOCH$_3$); 65.9 (0.5×CH$_2$OCOCH$_3$); 70.7 (0.5×CH$_2$CH$_3$); 70.8 (0.5×CH$_2$CH$_3$); 124.5 (q, J=281 Hz, 0.5×CF$_3$); 124.9 (q, J=Hz, 0.5×CF$_3$); 132.5 (2.5×CH$_{Ar.}$); 133.7 (2.5×CH$_{Ar.}$); 145.4 (0.5×Cq$_{Ar.}$); 146.3 (0.5×Cq$_{Ar.}$); 170.4 (0.5×OC=O); 170.6 (0.5×OC=O); 170.7 (0.5×C=O); 170.8 (0.5×C=O); 212.3 (0.5×C=S); 212.9 (0.5×C=S).

IR (ν, cm$^{-1}$) (CCl$_4$)

3442 (NH); 2984; 1752 (OC=O); 1703 (NC=O); 1506; 1442; 1381; 1367; 1340; 1224 (C=S); 1186; 1137; 1112; 1052.

Mass (IC, NH3)

424 (MH$^+$); 441 (MNH$_4^+$).

|  |  | Element: | |
|---|---|---|---|
|  |  | Carbon | Hydrogen |
| Microanalysis | Calculated (%) | 48.22 | 4.76 |
|  | Actual (%) | 48.08 | 4.83 |

Example 16

4-tertbutyloxycarbamate-2-ethoxythiocarbonylsulphanyl-5,5,5-trifluoro-pentylic ester of acetic acid

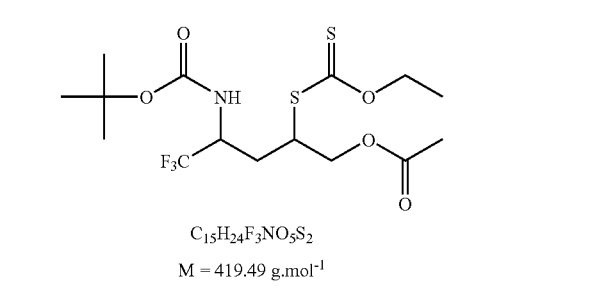

C$_{15}$H$_{24}$F$_3$NO$_5$S$_2$

M = 419.49 g.mol$^{-1}$

Reaction:

Carried out according to the general operating method with 50 mg (0.2 mmol) of xanthate of example 2 and 32 mg (0.4 mmol) of allyl acetate in 1,2-dichloroethane (1 ml). The reaction is terminated after the addition of 15% of LP (12 mg) and 4 hours 30 minutes under reflux.

Purification:

Chromatography over silica gel (ethyl acetate-petroleum ether 5/95).

Product:

Pale yellow oil.

Yield:

76% (2 diastereoisomers at a ratio of 1/1)

First Diastereoisomer:

$^1$HNMR (δ, ppm) (CDCl$_3$, 400 MHz)

1.38 (t, J=7.0 Hz, 3H, CH$_2$CH$_3$); 2.0 (s, 9H, 3×CH$_3$); 2.12 (s, 3H, COCH$_3$); 2.18-2.25 (m, 2H, CF$_3$CHNCH$_2$); 3.97-4.05 (m, 1H, CHS); 4.30 (dd, J$_1$=2.9 Hz, J$_2$=12.2 Hz, 1H, 1×CH$_2$OCOCH$_3$); 4.49 (dd, J$_1$=2.9 Hz, J$_2$=12.2 Hz, 1H, 1×CH$_2$OCOCH$_3$); 4.61 (q, J=5.9 Hz, 1H, CF$_3$CH); 4.65 (q, J=7.0 Hz, 2H, CH$_3$CH$_2$); 4.92 (d, J=11.7 Hz, 1H, NH).

NMR$^{13}$C (δ, ppm) (CDCl$_3$, 100 MHz)

13.7 (CH$_3$CH$_2$); 18.3 (3×CH$_3$); 28.6 (CH$_3$CO); 30.1 (CF$_3$CHNCH$_2$); 46.0 (CHS); 48.5 (q, J=30 Hz, CF$_3$CH); 65.9 (CH$_2$OCOCH$_3$); 70.8 (CH$_2$CH$_3$); 125.0 (q, J=Hz, CF$_3$); 152.2 (C(CH$_3$)$_3$); 170.6 (C=O); 170.9 (C=O); 212.7 (C=S).

IR (ν, cm$^{-1}$) (CCl$_4$)

3442 (NH); 2983; 1753 (C=O); 1422; 1263; 894; 869.

Mass (IC, NH3)

420 (MH$^+$); 437 (MNH$_4^+$).

|  |  | Element: | |
|---|---|---|---|
|  |  | Carbon | Hydrogen |
| Microanalysis | Calculated (%) | 42.95 | 5.77 |
|  | Actual (%) | 42.92 | 5.78 |

Second Diastereoisomer:

$^1$HNMR (δ, ppm) (CDCl$_3$, 400 MHz) 1.38 (t, J=7.0 Hz, 3H, CH$_2$CH$_3$); 2.05 (s, 9H, 3×CH$_3$); 2.14 (s, 3H, COCH$_3$); 2.19-2.22 (m, 2H, CF$_3$CHNCH$_2$); 4.05-4.12 (m, 1H, CHS); 4.32 (dd, J$_1$=2.9 Hz, J$_2$=12.2 Hz, 1H, 1×CH$_2$OCOCH$_3$); 4.42 (dd, J$_1$=2.9 Hz, J$_2$=12.2 Hz, 1H, 1×CH$_2$OCOCH$_3$); 4.56 (q, J=5.8 Hz, 1H, CF$_3$CH); 4.62 (q, J=7.0 Hz, 2H, CH$_3$CH$_2$); 4.75 (d, J=12.4 Hz, 1H, NH).

$^{13}$CNMR (δ, ppm) (CDCl$_3$, 100 MHz)

13.7 (CH$_3$CH$_2$); 18.5 (3×CH$_3$); 28.4 (CH$_3$CO); 29.0 (CF$_3$CHNCH$_2$); 45.6 (CHS); 48.5 (q, J=30 Hz, CF$_3$CH); 64.0 (CH$_2$OCOCH$_3$); 70.7 (CH$_2$CH$_3$); 124.7 (q, J=Hz, CF$_3$); 152.4 (C(CH$_3$)$_3$); 170.5 (C=O); 170.7 (C=O); 212.4 (C=S).

IR (ν, cm$^{-1}$) (CCl$_4$)

3442 (NH); 2983; 1732 (C=O); 1422; 1263; 894; 869.

Mass (IC, NH3)

420 (MH$^+$); 437 (MNH$_4^+$).

Example 17

O-ethyl and S-(3-tertbutyloxycarbamate-1-diethoxy-methyl-4,4,4-trifluoro-butyl ester of dithiocarbonic acid

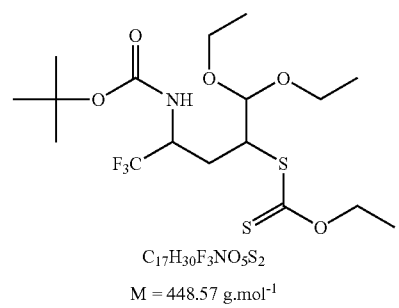

C$_{17}$H$_{30}$F$_3$NO$_5$S$_2$

M = 448.57 g.mol$^{-1}$

Reaction:

Carried out according to the general operating method with 50 mg (0.2 mmol) of xanthate of example 2 and 48 μL (0.4 mmol) of 3,3-diethoxy-propene in 1,2-dichloroethane (1 ml). The reaction is terminated after the addition of 15% of LP (12 mg) and 4 hours 30 minutes under reflux.

Purification:

Chromatography over silica gel (ethyl acetate-petroleum ether 5/95).

Product:

Thick pale yellow oil.

Yield:

94% (admixture of 2 diastereoisomers at a ratio of 1/1)

$^1$HNMR (δ, ppm) (CDCl$_3$, 400 MHz)

1.23 (t, J=6.1 Hz, 1.5H, CH$_2$CH$_3$); 1.25 (t, J=6.1 Hz, 1.5H, CH$_2$CH$_3$); 1.26 (t, J=6.1 Hz, 1.5H, CH$_2$CH$_3$); 1.28 (t, J=6.1 Hz, 1.5H, CH$_2$CH$_3$); 1.45 (t, J=6.1 Hz, 3H, CH$_2$CH$_3$); 1.52 (s, 4.5H, C(CH$_3$)$_3$); 1.56 (s, 4.5H, C(CH$_3$)$_3$); 1.75 (dd, J$_1$=4.0 Hz, J$_2$=14.2 Hz, 0.5H, CF$_3$CHNCH$_2$); 1.85 (dd, J$_1$=4.0 Hz, J$_2$=14.2 Hz, 0.5H, CF$_3$CHNCH$_2$); 2.15 (dd, J$_1$=4.0 Hz, J$_2$=14.2 Hz, 0.5H, CF$_3$CHNCH$_2$); 2.55 (dd, J$_1$=4.0 Hz, J$_2$=14.2 Hz, 0.5H, CF$_3$CHNCH$_2$); 3.53 (q, J=6.0 Hz, 1H, CH$_3$CH$_2$O); 3.55 (q, J=6.0 Hz, 1H, CH$_3$CH$_2$O); 3.63 (q, J=6.0 Hz, 1H, CH$_3$CH$_2$O); 3.78 (q, J=6.0 Hz, 1H, CH$_3$CH$_2$O); 3.85-4.02 (m, 1H, CHS); 4.06-4.12 (m, 1H, CH(OEt)$_2$); 4.48-4.51 (m, 1H, CF$_3$CH); 4.63 (q, J=6.1 Hz, 1H, CH$_3$CH$_2$); 4.73 (q, J=6.1 Hz, 1H, CH$_3$CH$_2$); 4.81 (d, J=12.2 Hz, 0.5H, NH); 4.83 (d, J=12.2 Hz, 0.5H, NH).

$^{13}$CNMR (δ, ppm) (CDCl$_3$, 100 MHz)

13.8 (CH$_3$CH$_2$); 15.2 (CH$_3$CH$_2$); 15.2 (0.5×CH$_3$CH$_2$); 15.3 (0.5×CH$_3$CH$_2$); 19.5 (3×CH$_3$); 25.8 (0.5×CH$_2$CHS); 28.5 (0.5×CH$_2$CHS); 48.4 (q, J=30 Hz, 0.5×CF$_3$CH); 49.0 (q, J=30 Hz, 0.5×CF$_3$CH); 49.9 (0.5×CHS); 50.4 (0.5×CHS); 64.0 (0.5×CH$_2$CH$_3$); 64.3 (0.5×CH$_2$CH$_3$); 64.7 (0.5×CH$_2$CH$_3$); 65.5 (0.5×CH$_2$CH$_3$); 70.5 (0.5×CH$_2$CH$_3$); 70.6 (0.5×CH$_2$CH$_3$); 102.7 (0.5×CH(OEt)$_2$); 103.9 (0.5×CH(OEt)$_2$); 124.9 (q, J=281 Hz, 0.5×CF$_3$); 125.1 (q, J=281 Hz, 0.5×CF$_3$); 150.4 (0.5×C(CH$_3$)$_3$); 151.2 (0.5×C(CH$_3$)$_3$); 170.1 (0.5×C=O); 171.3 (0.5×C=O); 213.9 (0.5×C=S); 214.7 (0.5×C=S).

IR (ν, cm$^{-1}$) (CCl$_4$)

3443 (NH); 2976; 2905; 2805; 1734 (C=O); 1720 (C=O); 1594; 1246; 1213; 1180; 1168; 1070.

Mass (IC, NH3)

402 (MH$^+$-EtOH).

| | | Element: | |
|---|---|---|---|
| | | Carbon | Hydrogen |
| Microanalysis | Calculated (%) | 48.20 | 6.97 |
| | Actual (%) | 47.05 | 6.93 |

Example 18

O-ethyl and S-(3-tertbutyl-oxycarbamate-1-diethoxy-methyl-4,4,4-trifluoro-butyl) diester of dithiocarbonic acid

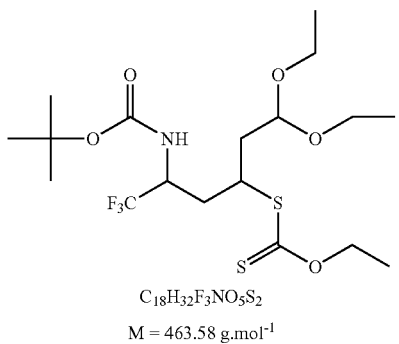

$C_{18}H_{32}F_3NO_5S_2$

M = 463.58 g.mol$^{-1}$

Reaction:
Carried out according to the general operating method with 200 mg (0.6 mmol) of xanthate of example 2 and 181 mg (1.25 mmol) of 4,4-diethoxy-butene in 1,2-dichloroethane (2 ml). The reaction is terminated after the addition of 15% of LP (36 mg) and 4 hours 30 minutes under reflux.

Purification:
Chromatography over silica gel (ethyl acetate-petroleum ether 5/95).

Product:
Thick pale yellow oil.

Yield:
72% (admixture of 2 diastereoisomers at a ratio of 1/1)

$^1$HNMR (δ, ppm) (CDCl$_3$, 400 MHz)

0.92 (dd, J$_1$=8.8 Hz, J$_2$=13.3 Hz, 1H, SCH—CH$_2$—CH); 0.95 (dd, J$_1$=8.8 Hz, J$_2$=13.3 Hz, 1H, SCH—CH$_2$—CH); 1.20 (t, J=7.0 Hz, 1.5H, CH$_2$CH$_3$); 1.25 (t, J=7.0 Hz, 1.5H, CH$_2$CH$_3$); 1.26 (t, J=7.0 Hz, 1.5H, CH$_2$CH$_3$); 1.28 (t, J=7.0 Hz, 1.5H, CH$_2$CH$_3$); 1.45 (t, J=7.0 Hz, 3H, CH$_2$CH$_3$); 1.52 (s, 4.5H, C(CH$_3$)$_3$); 1.56 (s, 4.5H, C(CH$_3$)$_3$); 1.98-2.07 (m, 1H, CF$_3$CHNCH$_2$); 2.08-2.15 (m, 1H, CF$_3$CHNCH$_2$); 3.68-3.74 (m, 2H, CH$_3$CH$_2$O); 3.79-3.82 (m, 2H, CH$_3$CH$_2$O); 3.92-3.99 (m, 1H, CH(OEt)$_2$); 4.02-4.13 (m, 1H, CHS); 4.43-4.51 (m, 1H, CF$_3$CH); 4.59-4.65 (m, 1H, CH$_3$CH$_2$O); 3.64-3.67 (m, 1H, CH$_3$CH$_2$O); 6.01 (d, J=12.0 Hz, 0.5H, NH); 6.13 (d, J=12.0 Hz, 0.5H, NH).

$^{13}$CNMR (δ, ppm) (CDCl$_3$, 100 MHz)

13.7 (CH$_3$CH$_2$); 13.8 (CH$_3$CH$_2$); 15.1 (0.5×CH$_3$CH$_2$); 15.3 (0.5×CH$_3$CH$_2$); 19.8 (3×CH$_3$); 21.1 (0.5×CH—CH$_2$—CH); 21.3 (0.5×CH—CH$_2$—CH); 28.5 (0.5×CH$_2$CHS); 28.7 (0.5×CH$_2$CHS); 49.2 (q, J=30 Hz, 0.5×CF$_3$CH); 49.5 (q, J=30 Hz, 0.5×CF$_3$CH); 51.8 (0.5×CHS); 52.1 (0.5×CHS); 64.04 (0.5×CH$_2$CH$_3$); 64.2 (0.5×CH$_2$CH$_3$); 65.2 (0.5×CH$_2$CH$_3$); 65.5 (0.5×CH$_2$CH$_3$); 70.4 (0.5×CH$_2$CH$_3$); 70.6 (0.5×CH$_2$CH$_3$); 100.9 (0.5×CH(OEt)$_2$); 101.3 (0.5×CH(OEt)$_2$); 122.8 (q, J=Hz, 0.5×CF$_3$); 123.0 (q, J=283 Hz, 0.5×CF$_3$); 158.3 (0.5×C(CH$_3$)$_3$); 158.4 (0.5×C(CH$_3$)$_3$); 170.0 (0.5×C=O); 171.4 (0.5×C=O); 214.0 (0.5×C=S); 214.2 (0.5×C=S).

IR (ν, cm$^{-1}$) (CCl$_4$)

3440 (NH); 2973; 2910; 2810; 1732 (C=O); 1730 (C=O); 1594; 1243; 1210; 1176; 1164; 1064.

Mass (IC, NH3)

420 (MH$^+$-EtOH).

Conversions of the Adducts Having the Formula (IIA)

Example 19

N-[3-(2-oxo-pyrrolidin-1-yl)-1-trifluoromethyl-allyl] acetamide

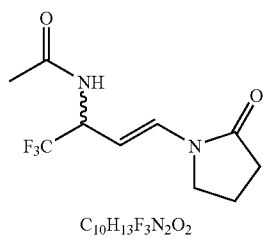

$C_{10}H_{13}F_3N_2O_2$

M = 250.22 g.mol$^{-1}$

Reaction:
A solution of xanthate of example 12 (170 mg, 0.45 mmol) in 5 ml of chlorobenzene is brought to reflux for 2 hours. The crude reaction product is brought to ambient temperature then concentrated at reduced pressure before being purified.

Purification:
Chromatography over silica gel (dichloromethane-methanol 98/2).

Product:
Pale yellow oil.

Yield:
Quantitative.

$^1$HNMR (δ, ppm) (CDCl$_3$, 400 MHz)

2.03 (s, 3H, COCH$_3$); 2.06-2.14 (m, 2H, CH$_2$CH$_2$CH$_2$); 2.46 (dd, J=7.3 Hz, 7.3 Hz, 2H, CH$_2$CO); 3.49 (dd, J=7.3 Hz, 7.3 Hz, 2H, CH$_2$N); 4.87 (dd, J=14.7 Hz, 6.4 Hz, 1H, CH=CHN); 5.22 (qdd, J=9.4 Hz, 7.6 Hz, 6.4 Hz, 1H, CF$_3$CH); 7.20 (d, J=14.7 Hz, 1H, CH=CHN); 7.43 (d, J=9.4 Hz, 1H, NH).

$^{13}$CNMR (δ, ppm) (CDCl$_3$, 100 MHz)

17.33 (CH$_2$CH$_2$CH$_2$); 22.82 (CH$_3$CO); 31.04 (CH$_2$CO); 45.09 (CH$_2$N); 50.60 (q, J=30 Hz, CF$_3$CH); 101.48 (CH=CHN); 124.53 (q, J=281 Hz, CF$_3$); 128.57 (CH=CHN); 170.28 (C=O); 173.84 (C=O).

IR (ν, cm$^{-1}$) (CCl$_4$)

3444 (NH); 2980; 1708 (C=O); 1667; 1558; 1497; 1400; 1262; 1235; 1186; 1131.

Mass (IC, NH$_3$)

251 (MH$^+$); 268 (MNH$_4^+$).

|   |   | Element: | |
|---|---|---|---|
|   |   | Carbon | Hydrogen |
| Microanalysis | Calculated (%) | 48.00 | 5.24 |
|   | Actual (%) | 47.62 | 5.31 |

|   |   | Element: | |
|---|---|---|---|
|   |   | Carbon | Hydrogen |
| Microanalysis | Calculated (%) | 54.88 | 4.61 |
|   | Actual (%) | 54.84 | 4.58 |

Example 20

N-[4-(1,3-dioxo-1,3-dihydro-isoindol-2-yl)-1-trifluoromethyl-butyl]acetamide

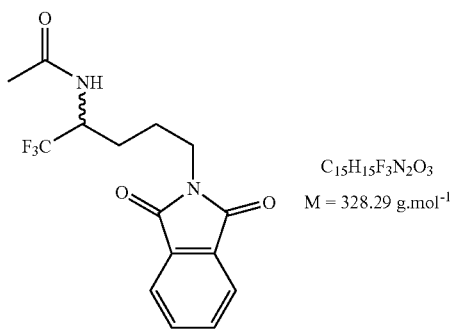

$C_{15}H_{15}F_3N_2O_3$

M = 328.29 g.mol$^{-1}$

Reaction:

LP is added, at a rate of 10 mol % (22 mg, 0.056 mmol) every hour, to a solution of the xanthate adduct of example 9 (250 mg, 0.56 mmol) in 4 ml propan-2-ol, which solution has been degassed beforehand at reflux under argon. The reaction is stopped after 11 hours under reflux and the addition of 110% of LP (244 mg, 0.61 mmol). The reaction medium is then brought to ambient temperature and concentrated at reduced pressure before being purified.

Purification:
Chromatography over silica gel (ethyl acetate-petroleum ether 4/6).
Product:
White crystalline.
Yield:
78%
$^1$HNMR (δ, ppm) (CDCl$_3$, 400 MHz)
1.48-1.60 (m, 1H, CF$_3$CH(NAc)CH$_2$); 1.74-1.89 (m, 3H, CH$_2$CH$_2$N+CF$_3$CH(NAc)CH$_2$); 3.69 (t, J=6.8 Hz, 2H, CH$_2$CH$_2$N); 4.59-4.72 (m, 1H, CF$_3$CH); 6.40 (d, J=9.3 Hz, 1H, NH); 7.69-7.71 (m, 2H, H$_{Ar.}$); 7.79-7.81 (m, 2H, H$_{Ar.}$).
$^{13}$CNMR (δ, ppm) (CDCl$_3$, 100 MHz)
23.02 (CH$_3$CO); 24.72 (CH$_2$); 25.14 (CH$_2$); (CH$_2$N); 50.18 (q, J=30 Hz, CF$_3$CH); 123.35 (2×CH$_{Ar.}$); 125.05 (q, J=281 Hz, CF$_3$); 131.93 (Cq$_{Ar.}$); 134.19 (2×CH$_{Ar.}$); 168.48 (2×C=O$_{Ar.}$); 170.55 (C=O).
IR (ν, cm$^{-1}$)(CCl$_4$)
3445 (NH); 2932; 1774 (C=O); 1717 (C=O); 1505; 1438; 1396; 1369; 1244; 1187; 1136.
MP (° C.)
179-180 (ethyl acetate-heptane)
Mass (IC, NH$_3$)
329 (MH$^+$); 345 (MNH$_4^+$).

Example 21

Ester of dithiocarbonic acid S-{1-[5-(1-acetylamino-2,2,2-trifluoro-ethyl)-2-oxo-[1,3]dioxolan-4-ylmethyl]-2,2-diethoxy-ethyl}O-ethyl ester

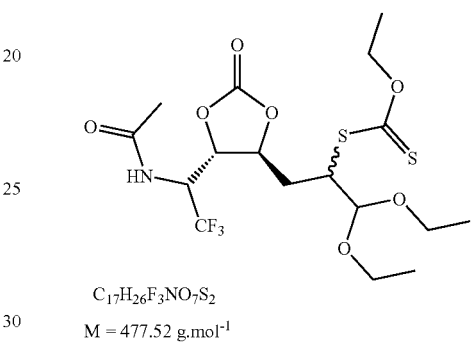

$C_{17}H_{26}F_3NO_7S_2$

M = 477.52 g.mol$^{-1}$

Reaction:
Carried out according to the general operating method with 95 mg (0.27 mmol) of xanthate of example 4 and 125 µl (0.82 mmol) of 3,3-diethoxy-propene in 1 ml of 1,2-dichloroethane. The reaction is terminated after the addition of 5% of LP and 1 hour under reflux.
Purification:
Chromatography over silica gel (ethyl acetate-petroleum ether 3/7).
Product:
Pale yellow oil.
Yield:
40% (2 diastereoisomers at a ratio of 1/1), isolated with 17% of the double addition product:

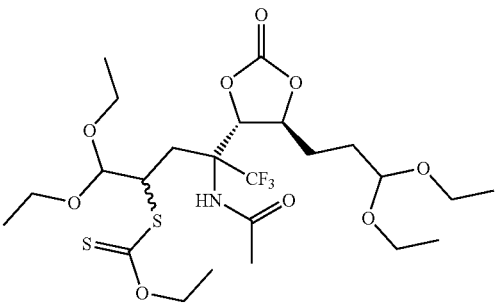

$^1$HNMR (δ, ppm) b (CDCl$_3$, 400 MHz)
1.17 (t, J=7.0 Hz, 3H, CH$_2$CH$_3$); 1.19 (t, J=7.0 Hz, 3H, CH$_2$CH$_3$); 1.22 (t, J=7.0 Hz, 3H, CH$_2$CH$_3$); 1.23 (t, J=7.0 Hz, 3H, CH$_2$CH$_3$); 1.42 (t, J=7.0 Hz, 3H, CH$_2$CH$_3$); 1.43 (t, J=7.0 Hz, 3H, CH$_2$CH$_3$); 1.95-2.15 (m, 2H, CH$_2$CHS); 2.07 (s, 3H, COCH$_3$); 2.09 (s, 3H, COCH$_3$); 2.37-2.45 (m, 2H, CH$_2$CHS;

3.42-3.82 (m, 8H, CH₃CH₂); 4.05-4.15 (m, 2H, CHS); 4.49-4.59 (m, 2H, CHOCO); 4.59 (s, 1H, CH(OEt)₂); 4.60 (s, 1H, CH(OEt)₂); 4.63 (q, J=7.0 Hz, 2H, CH₃CH₂); 4.64 (q, J=7.0 Hz, 2H, CH₃CH₂); 4.77-4.89 (m, 1H, CHOCO); 4.97-5.09 (m, 3H, CF₃CH+CHOCO); 6.81 (d, J=9.4 Hz, 1H, NH); 6.83 (d, J=9.4 Hz, 1H, NH).

$^{13}$CNMR (δ, ppm) (CDCl₃, 100 MHz)

13.78 (2×CH₃CH₂); 15.15 (CH₃CH₂); 15.23 (CH₃CH₂); 15.29 (2×CH₃CH₂); 22.70 (CH₃CO); 22.78 (CH₃CO); 33.22 (CH₂CHS); 34.24 (CH₂CHS); 48.94 (CHS); 49.66 (CHS); 51.01 (q, J=31 Hz, CF₃CH); 51.08 (q, J=31 Hz, CF₃CH); 64.36 (CH₂CH₃); 64.47 (CH₂CH₃); 65.35 (CH₂CH₃); 65.59 (CH₂CH₃); 70.75 (CH₂CH₃); 70.84 (CH₂CH₃); 76.37 (CHOCO); 77.10 (CHOCO); 77.91 (CHOCO); 78.39 (CHOCO); 103.49 (CH(OEt)₂); 103.57 (CH(OEt)₂); 123.58 (q, J=282 Hz, CF₃); 123.64 (q, J=283 Hz, CF₃); 153.34 (OC=O); 153.46 (OC=O); 170.58 (NC=O); 170.70 (NC=O); 212.76 (C=S); 213.04 (C=S).

Mass (IC, NH3)

433 (M-EtOH+H⁺); 496 (MNH₄⁺).

Example 22

N-(3,3-dimethoxy-1-trifluoromethyl-propyl)-acetamide

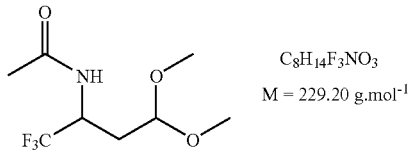

C₈H₁₄F₃NO₃

M = 229.20 g.mol⁻¹

Reaction:

A catalytic quantity of (±)-10-camphorsulphonic acid is added to a solution of xanthate of example 5 (200 mg, 0.57 mmol) in 10 ml of methanol. The whole is brought to reflux for 24 hours. The crude reaction product is then brought to ambient temperature then concentrated at reduced pressure before being purified.

Purification:

Chromatography over silica gel (ethyl acetate-petroleum ether 7/3).

Product:

Colourless crystalline.

Yield:

72% (10% of the aldehyde which corresponds to the unprotected product is also isolated).

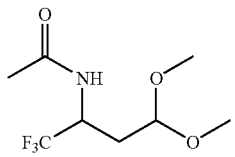

$^1$HNMR (δ, ppm) (CDCl₃, 400 MHz)

1.90 (ddd, J=14.4 Hz, 10.0 Hz, 4.0 Hz, 1H, CH₂); 2.04 (ddd, J=14.4 Hz, 7.6 Hz, 3.3 Hz, 1H, CH₂); 2.02 (s, 3H, COCH₃); 3.31 (s, 3H, OCH₃); 3.33 (s, 3H, OCH₃); 4.43 (dd, J=7.6 Hz, 4.0 Hz, 1H, CH(OMe)₂); 4.66-4.78 (m, 1H, CF₃CH); 6.66 (d, J=9.4 Hz, 1H, NH).

$^{13}$CNMR (δ, ppm) (CDCl₃, 100 MHz)

22.97 (CH₃CO); 31.69 (CH₂); 47.54 (q, J=31 Hz, CF₃CH); 53.29 (OCH₃); 53.88 (OCH₃); 101.55 (CH(OMe)₂); 125.09 (q, J=281 Hz, CF₃); 170.46 (NC=O).

IR (ν, cm⁻¹) (CCl₄)

3444 (NH); 2936; 2833; 1704 (C=O); 1505; 1434; 1371; 1285; 1248; 1188; 1138; 1065.

MP (° C.)

56-58 (ethyl acetate-heptane).

Mass (IC, NH₃)

198 (M-MeOH+H⁺); 230 (MH⁺).

|  |  | Element: | |
| --- | --- | --- | --- |
|  |  | Carbon | Hydrogen |
| Microanalysis | Calculated (%) | 41.92 | 6.16 |
|  | Actual (%) | 41.84 | 6.09 |

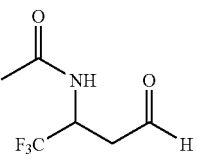

$^1$HNMR (δ, ppm) (CDCl₃, 400 MHz)

2.01 (s, 3H, COCH₃); 2.79-2.83 (m, 2H, CH₂); 5.08-5.21 (m, 1H, CF₃CH); 7.15 (d, J=9.4 Hz, 1H, NH); 9.68 (s, 1H, HC=O).

$^{13}$CNMR (δ, ppm) (CDCl₃, 100 MHz)

22.76 (CH₃CO); 41.86 (CH₂); 458554 (q, J=33 Hz, CF₃CH); 124.76 (q, J=281 Hz, CF₃); 170.54 (NC=O); 197.18 (HC=O).

Example 23

N-[1-(5-bromo-1-methanesulphonyl-2,3-dihydro-1H-indol-3-ylmethyl)-2,2,2-trifluoro-ethyl]-acetamide

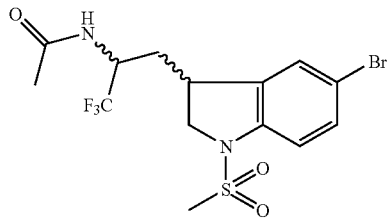

C₁₄H₁₆BrF₃N₂O₃S

M = 429.25 g.mol⁻¹

Reaction:

LP is added, at a rate of 10 mol % (28 mg, 0.07 mmol) every hour, to a solution of the xanthate adduct of example 13 (396 mg, 0.72 mmol) in 4 ml of 1,2-dichloroethane, which solution has been degassed beforehand at reflux under argon. The reaction is stopped after 11 hours under reflux and the addition of 110% of LP (314 mg, 0.790 mmol). The reaction medium is then brought to ambient temperature and concentrated at reduced pressure before being purified.

Purification:

Chromatography over silica gel (ethyl acetate-petroleum ether 5/5).

Product:

White crystalline.

Yield:

90% (2 diastereoisomers at a ratio of 6/4)

First Diastereoisomer (Majority)

$^1$HNMR (δ, ppm) ((CD$_3$)$_2$CO, 400 MHz)

1.92-2.10 (m, 1H, CF$_3$CH(NAc)CH$_2$); 1.97 (s, 3H, COCH$_3$); 2.18-2.24 (m, 1H, CF$_3$CH(NAc)CH$_2$); 3.01 (s, 3H, SO$_2$CH$_3$); 3.52-3.63 (m, 1H, NCH$_2$CH); 3.83 (d, J=10.3 Hz, 5.4 Hz, 1H, NCH$_2$); 4.15 (d, J=10.3 Hz, 10.0 Hz, 1H, NCH$_2$); 4.80-4.95 (m, 1H, CF$_3$CH); 7.29 (d, J=8.6 Hz, 1H, H$_{Ar}$(HC=CNSO$_2$)); 7.41 (d, J=8.6 Hz, 1H, H$_{Ar}$(HC=CBr)); 7.66 (s, 1H, H$_{Ar}$(HC=CBr)); 7.76 (d, J=9.4 Hz, 1H, NH).

$^{13}$CNMR (δ, ppm) (CD$_3$)$_2$CO, 400 MHz)

22.76 (CH$_3$CO); 33.25 (CF$_3$CH(NAc)CH$_2$); 34.82 (NCH$_2$); 37.40 (CH$_3$SO$_2$); 49.28 (q, J=30 Hz, CF$_3$CH); 57.08 (NCH$_2$); 115.83 (CH$_{Ar.}$); 116.26 (Cq$_{Ar.}$); 126.42 (q, J=281 Hz, CF$_3$); 129.51 (CH$_{Ar.}$); 132.12 (CH$_{Ar.}$); 137.35 (Cq$_{Ar.}$); 142.52 (Cq$_{Ar.}$); 170.72 (C=O).

Second Diastereoisomer (Minority)

$^1$HNMR (δ, ppm) (CD$_3$)$_2$CO, 400 MHz)

1.96-2.07 (m, 1H, CF$_3$CH(NAc)CH$_2$); 2.03 (s, 3H, COCH$_3$); 2.20-2.27 (m, 1H, CF$_3$CH(NAc)CH$_2$); 3.02 (s, 3H, SO$_2$CH$_3$); 3.57-3.66 (m, 1H, NCH$_2$CH); 3.82 (d, J=10.0 Hz, 7.5 Hz, 1H, NCH$_2$); 4.11 (d, J=10.0 Hz, 9.5 Hz, 1H, NCH$_2$); 4.74-4.87 (m, 1H, CF$_3$CH); 7.29 (d, J=8.5 Hz, 1H, H$_{Ar}$(HC=CNSO$_2$)); 7.40 (d, J=8.5 Hz, 1H, H$_{Ar}$(HC=CBr)); 7.41 (s, 1H, H$_{Ar}$(HC=CBr)); 7.67 (d, J=9.3 Hz, 1H, NH).

$^{13}$CNMR (δ, ppm) (CD$_3$)$_2$CO, 400 MHz)

22.77 (CH$_3$CO); 32.87 (CF$_3$CH(NAc)CH$_2$); 34.70 (NCH$_2$); 36.71 (CH$_3$SO$_2$); 49.04 (q, J=30 Hz, CF$_3$CH); 56.42 (NCH$_2$); 115.86 (CH$_{Ar.}$); 116.22 (Cq$_{Ar.}$); 126.50 (q, J=281 Hz, CF$_3$); 128.38 (CH$_{Ar.}$); 131.99 (CH$_{Ar.}$); 137.83 (Cq$_{Ar.}$); 142.79 (Cq$_{Ar.}$); 170.87 (C=O).

Analyses on the Admixture of Diastereoisomers

IR (ν, cm$^{-1}$) (nujol)

3285 (NH); 1759 (C=O); 1549; 1352; 1307; 1269; 1214; 1161; 1128; 1112.

Mass (IC, NH$_3$)

430 (MH$^+$); 447 (MNH$_4^+$).

|  |  | Element: | |
|---|---|---|---|
|  |  | Carbon | Hydrogen |
| Microanalysis | Calculated (%) | 39.17 | 3.76 |
|  | Actual (%) | 38.73 | 3.69 |

Example 24

Ester of S-{2-[5-(1-acetylamino-2,2,2-trifluoro-ethyl)-2-oxo-[1,3]dioxolan-4-yl]-1-trimethylsilanyl-methyl-ethyl}dithiocarbonic acid O-ethyl ester

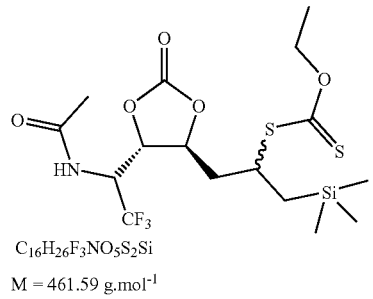

$C_{16}H_{26}F_3NO_5S_2Si$

M = 461.59 g.mol$^{-1}$

Reaction:

Carried out according to the general operating method with 130 mg (0.37 mmol) of xanthate of example 4 and 178 μl (1.12 mmol) of allyl-trimethyl-silane in 1 ml of 1,2-dichloroethane. The reaction is terminated after the addition of 5% of LP and 45 minutes under reflux.

Purification:

Chromatography over silica gel (ether-petroleum ether 3/7).

Product:

Pale yellow oil.

Yield:

72% (2 diastereoisomers at a ratio of 1/1)

$^1$HNMR (δ, ppm) (CDCl$_3$, 400 MHz)

0.07 (s, 9H, (CH$_3$)$_3$Si); 0.08 (s, 9H, (CH$_3$)$_3$Si); 0.96-1.15 (m, 4H, CH$_2$Si(CH$_3$)$_3$); 1.41 (t, J=7.0 Hz, 3H, CH$_2$CH$_3$); 1.42 (t, J=7.0 Hz, 3H, CH$_2$CH$_3$); 2.12 (s, 6H, 2×COCH$_3$); 2.14-2.35 (m, 4H, 2×OCHCH$_2$CHS); 3.83-3.90 (m, 1H, CHS); 3.90-3.97 (m, 1H, CHS); 4.54-4.62 (m, 2H, 2×CHSCH$_2$CHO); 4.63 (q, J=7.0 Hz, 2H, CH$_3$CH$_2$); 4.64 (q, J=7.0 Hz, 2H, CH$_3$CH$_2$); 4.75 (d, 1H, J=5.8 Hz, 1H, CF$_3$CHCH(NAc)CHO); 4.84 (d, 1H, J=6.58 Hz, 1H, CF$_3$CHCH(NAc)CHO); 4.93-5.04 (m, 2H, CF$_3$CH); 7.45 (d, J=10.5 Hz, 1H, NH); 7.47 (d, J=10.5 Hz, 1H, NH).

$^{13}$CNMR (δ, ppm) (CDCl$_3$, 100 MHz)

0.79 to –0.65 (m, (CH$_3$)$_3$Si); 13.81 (2×CH$_3$CH$_2$); 20.99 (OCHCH$_2$CHS); 22.57 (2×CH$_3$CO); 22.92 (OCHCH$_2$CHS); 41.29 (CH$_2$Si); 42.12 (CH$_2$Si); 43.72 (CHS); 44.33 (CHS); 50.70 (q, J=32 Hz, 2×CF$_3$CH); 70.25 (CH$_2$CH$_3$); 70.29 (CH$_2$CH$_3$); 76.75 (CHOC=O); 77.19 (CHOC=O); 77.83 (CHOC=O); 77.99 (CHOC=O); 123.45 (q, J=283 Hz, 2×CF$_3$); 154.02 (OC=O); 154.13 (OC=O); 171.66 (NC=O); 171.83 (NC=O); 213.11 (C=S); 213.22 (C=S).

IR (ν, cm$^{-1}$) (CCl$_4$)

3435 (NH); 3328 (NH); 2954; 1807 (C=O); 1697 (C=O); 1502; 1371; 1301; 1277; 1251; 1221; 1189; 1142; 1111; 1050.

Mass (IC, NH$_3$)

340 (M-HSCSOEt+H$^+$); 463 (MH$^+$); 480 (MNH$_4^+$).

Example 25

N-[1-(5-ethoxy-2-oxo-[1,3]dithiolan-4-ylmethyl)-2,2,2-trifluoro-ethyl]-acetamide

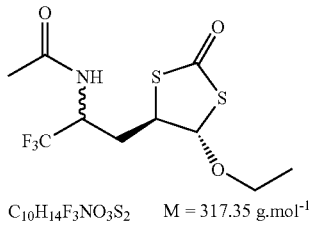

$C_{10}H_{14}F_3NO_3S_2$   $M = 317.35$ g.mol$^{-1}$

Reaction:

4 drops of concentrated sulphuric acid are added to a solution of xanthate adduct of example 8 in 10 ml of methanol. After 48 hours at ambient temperature, the methanol is evaporated at reduced pressure and the residue is placed in dichloromethane. A saturated solution of sodium hydrogen carbonate is added and the organic phase is separated. After drying over magnesium sulphate, filtration and concentration in a vacuum, the organic residue is then purified.

Purification:

Chromatography over silica gel (ethyl acetate-petroleum ether 3/7).

Product:

Pale yellow oil.

Yield:

21%

$^1$HNMR (δ, ppm) (CDCl$_3$, 400 MHz)

1.24 (t, J=7.0 Hz, 3H, CH$_2$CH$_3$); 1.27 (t, J=7.0 Hz, 3H, CH$_2$CH$_3$); 2.02-2.08 (m, 2H, CF$_3$CH(NAc)CH$_2$); 2.07 (s, 3H, COCH$_3$); 2.08 (s, 3H, COCH$_3$); 2.45 (ddd, 1H, J=14.6 Hz, 8.2 Hz, 4.1 Hz, 1H, CF$_3$CH(NAc)CH$_2$); 2.57 (ddd, 1H, J=14.6 Hz, 10.0 Hz, 2.9 Hz, 1H, CF$_3$CH(NAc)CH$_2$); 3.44-3.54 (m, 2H, CH$_2$CH$_3$); 3.70-3.84 (m, 2H, CH$_2$CH$_3$); 4.03-4.07 (m, 1H, CH$_2$CHS); 4.30-4.75 (m, 1H, CH$_2$CHS); 4.67-4.88 (m, 2H, CF$_3$CH); 5.52 (d, J=1.9 Hz, 1H, SCH(OEt)); 5.60 (d, J=3.5 Hz, 1H, SCH(OEt)); 6.59 (d, J=10.0 Hz, 1H, NH); 6.63 (d, J=9.4 Hz, 1H, NH).

$^{13}$CNMR (δ, ppm) (CDCl$_3$, 100 MHz)

14.45 (CH$_2$CH$_3$); 14.66 (CH$_2$CH$_3$); 22.97 (CH$_3$CO); 23.07 (CH$_3$CO); 28.25 (CH$_2$CHS); 33.31 (CH$_2$CHS); 47.95 (q, J=30 Hz, CF$_3$CH); 48.87 (q, J=30 Hz, CF$_3$CH); 53.21 (CH$_2$CHS); 54.49 (CH$_2$CHS); 65.68 (CH$_2$CH$_3$); 65.92 (CH$_2$CH$_3$); 90.58 (SCH(OEt)); 94.07 (SCH(OEt)); 123.51 (q, J=282 Hz, CF$_3$); 123.58 (q, J=282 Hz, CF$_3$); 170.85 (NC=O); 171.14 (NC=O); 195.48 (SC=O); 195.67 (SC=O).

IR (ν, cm$^{-1}$) (CCl$_4$)

3439 (NH); 2981; 1701 (C=O); 1666 (C=O); 1549; 1500; 1239; 1192; 1144.

Mass (IC, NH$_3$)

272 (M-EtOH+H$^+$); 318 (MH$^+$); 335 (MNH$_4^+$).

Example 26

4-benzoylamino-5,5-5-trifluoro-butyl ester of acetic acid

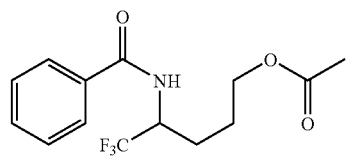

$C_{14}H_{16}F_3NO_3$ $M = 303.11$ g.mol$^{-1}$

Reaction:

LP is added, at a rate of 10% (52 mg, 0.13 mmol) every hour, to a solution of xanthate adduct of example 15 (551 mg, 1.30 mmol) in propan-2-ol (8 ml), which solution has been degassed beforehand at reflux under argon. The reaction is stopped after 11 hours under reflux and the addition of 120% of LP (6.2 g, 15.5 mmol). The reaction medium is then brought to ambient temperature and concentrated at reduced pressure before being purified.

Purification:

Chromatography over silica gel (ethyl acetate-petroleum ether 1/9).

Product:

Translucent crystals.

Yield:

62%

$^1$HNMR (δ, ppm) (CDCl$_3$, 400 MHz)

1.6 (quin, J=7.2 Hz, 2H, CH$_2$CH$_2$CH$_2$); 2.01 (s, 3H, COCH$_3$); 2.23 (t, J=8.3 Hz, 2H, CF$_3$CHNCH$_2$); 4.05 (t, J=8.8 Hz, 2H, CH$_2$OCOCH$_3$); 4.85 (m, 1H, CF$_3$CH); 6.34 (d, J=8.9 Hz, 1H, NH); 7.41-7.92 (m, 5H, CH$_{Ar.}$).

NMR$^{13}$C (δ, ppm) (CDCl$_3$, 100 MHz)

22.8 (CH$_3$CO); 28.4 (q, J=30 Hz, CF$_3$CH); 33.2 (CF$_3$CHNCH$_2$); 31.8 (CF$_3$CHNCH$_2$); 63.7 (CH$_2$OCOCH$_3$); 124.7 (q, J=281 Hz, CF$_3$); 128.5 (2×CH$_{Ar.}$); 128.9 (2×CH$_{Ar.}$); 129.2 (CH$_{Ar.}$); 132.4 (Cq$_{Ar.}$); 179.6 (C=O); 180.0 (C=O).

IR (ν, cm$^{-1}$) (CCl$_4$)

3451 (NH); 2926; 2881; 1710 (C=O); 1688 (C=O); 1510; 1486; 1455; 1367; 1236; 1187; 1147; 1072.

Mass (IC, NH3)

304 (MH$^+$); 321 (MNH$_4^+$).

| | | Element | |
|---|---|---|---|
| | | Carbon | Hydrogen |
| Microanalysis | Calculated (%) | 55.44 | 5.32 |
| | Actual (%) | 55.27 | 5.18 |

MP

49° C. (ether)

Examples of the Method for Preparing Compounds Having the Formula (VIIIA)

Example 27

N-(2-acetylamino-3,3,3-trifluoro-1-trifluoromethyl-propyl)-acetamide

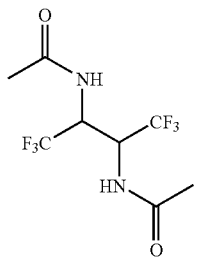

$C_8H_{10}F_6N_2O_2$
M = 280.17 g.mol$^{-1}$

Reaction:

LP is added, at a rate of 10 mol % (80 mg, 0.2 mmol) every 10 minutes, to a solution of xanthate of example 1 (522 mg, 2 mmol) in 16 ml of chlorobenzene, which solution has been degassed beforehand at reflux under argon. The reaction is stopped after 2 hours under reflux and the addition of 120% of LP (960 mg, 2.4 mmol). The reaction medium is then brought to ambient temperature and concentrated at reduced pressure before being purified.

Purification:

By means of precipitation in an admixture of ether-petroleum ether 1/9.

Product:

Colourless solid.

Yield:

79% (2 diastereoisomers at a ratio of 7/5)

First Diastereoisomer (Majority)

$^1$HNMR (δ, ppm) ((CD$_3$)$_2$SO, 400 MHz)

1.90 (s, 6H, CH$_3$CO); 4.90-5.03 (m, 2H, CF$_3$CH); 8.86 (d, J=8.7 Hz, 2H, NH).

$^{13}$CNMR (δ, ppm) ((CD$_3$)$_2$SO, 400 MHz)

22.21 (2×CH$_3$CO); 47.77 (q, J=29 Hz, 2×CF$_3$CH); 124.01 (q, J=282 Hz, 2×CF$_3$); 169.61 (2×NC=O).

Second Diastereoisomer (Minority)

NMR$^1$H (δ, ppm) ((CD$_3$)$_2$SO, 400 MHz)

1.98 (s, 6H, CH$_3$CO); 5.17 (qd, J=8.2 Hz, 9.2 Hz, 2H, CF$_3$CH); 8.41 (d, J=9.2 Hz, 2H, NH).

$^{13}$CNMR (δ, ppm) ((CD$_3$)$_2$SO, 400 MHz)

22.40 (2×CH$_3$CO); 47.19 (q, J=29 Hz, 2×CF$_3$CH); 123.89 (q, J=282 Hz, 2×CF$_3$); 169.54 (2×NC=O).

Analyses on the Admixture of Diastereoisomers

IR (v, cm$^{-1}$) (nujol)

3284 (NH); 3072; 1674 (C=O); 1547; 1340; 1301; 1255; 1238; 1181; 1153; 1108.

Mass (IC, NH$_3$)

281 (MH$^+$); 298 (MNH$_4^+$).

| | | Element: | |
|---|---|---|---|
| | | Carbon | Hydrogen |
| Microanalysis | Calculated (%) | 34.30 | 3.60 |
| | Actual (%) | 33.67 | 3.63 |

Example of the Method for Preparing Compounds Having the Formula (I$_B$)

Synthesis of Xanthate 2-Trifluoromethylethanol

Example 28

O-ethyl and S-(1-hydroxy-2,2,2-trifluoro-ethyl) ester of dithiocarbonic acid

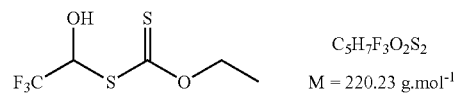

$C_5H_7F_3O_2S_2$
M = 220.23 g.mol$^{-1}$

Reaction:

The salt of potassium ethylxanthogenate (737 mg, 4.62 mmol) is added to a solution of 2,2,2-trifluoro-1-methoxy-ethanol (300 mg, 2.31 mmol) in acetone (5 ml). The reaction admixture is cooled to 0° C. and sulphuric acid (123.6 μL, 2.31 mmol) is added drop by drop. After 1 hour at 0° C., the reaction admixture is concentrated at reduced pressure. The residue is placed in ether, filtered and concentrated again at reduced pressure.

Product:

Yellow oil.

Yield:

69%

NMR$^1$H (δ, ppm) (CDCl$_3$, 400 MHz)

1.54 (t, J=6.3 Hz, 3H, CH$_2$CH$_3$); 4.71 (q, J=6.3 Hz, 2H, CH$_3$CH$_2$); 6.02 (q, J=5.7 Hz, 1H, CF$_3$CH).

NMR$^{13}$C (δ, ppm) (CDCl$_3$, 100 MHz)

13.7 (CH$_3$CH$_2$); 57.8 (q, J=30 Hz, CF$_3$CH); 71.4 (CH$_2$CH$_3$); 124.4 (q, J=280 Hz, CF$_3$); 207.1 (C=S).

IR (v, cm$^{-1}$)(CCl$_4$)

2961; 1453; 1314; 1231; 1130; 1052; 1023.

Mass (IC, NH3)

221 (MH$^+$), 238 (MNH$_4^+$).

Example 29

O-ethyl and S-(1-acetyl-2,2,2-trifluoro-ethyl) ester of dithiocarbonic acid

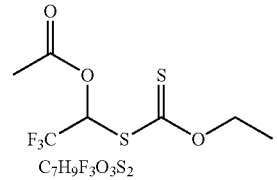

$C_7H_9F_3O_3S_2$
M = 262.27 g.mol$^{-1}$

Reaction:

The salt of potassium ethylxanthogenate (4.61 g, 46.2 mmol) is added to a solution of 2,2,2-trifluoro-1-methoxyethanol (3 g, 23.1 mmol) in acetone (15 ml). The reaction admixture is cooled to 0° C. and sulphuric acid (1.24 ml, 23.1 mmol) is added drop by drop. After 1 hour at 0° C., the reaction admixture is concentrated at reduced pressure. The residue is placed in ether, filtered and concentrated again at reduced pressure.

The residue is placed in acetone (5 ml), cooled to 0° C. Sulphuric acid (1.24 ml, 23.1 mmol), then acetic anhydride (21.7 ml, 231 mmol) are added drop by drop.

After one hour at 0° C., the reaction admixture is concentrated at reduced pressure, placed in ether, washed in water and then with an aqueous solution saturated with potassium carbonate, dried and concentrated again at reduced pressure.

Purification:
Chromatography over silica gel (ethyl acetate-petroleum ether 1/9)
Product:
Yellow oil.
Yield:
60%
$^1$HNMR ($\delta$, ppm) (CDCl$_3$, 400 MHz)
1.48 (t, J=5.8 Hz, 3H, CH$_2$CH$_3$); 2.21 (s, 3H, COCH$_3$); 4.71 (q, J=5.8 Hz, 2H, CH$_3$CH$_2$); 7.32 (q, J=6.0 Hz, 1H, CF$_3$CH).
$^{13}$CNMR ($\delta$, ppm) (CDCl$_3$, 100 MHz)
12.5 (CH$_3$CH$_2$); 21.0 (COCH$_3$); 57.6 (q, J=38 Hz, CF$_3$CH); 70.4 (CH$_2$CH$_3$); 123.0 (q, J=280 Hz, CF$_3$); 179.5 (C=O); 206.9 (C=S).

IR ($\nu$, cm$^{-1}$) (CCl$_4$)
2986; 2939; 1778 (C=O); 1442; 1370; 1344; 1194; 1131; 1032; 868; 823.
Mass (IC, NH3)
262 (MH$^+$), 279 (MNH$_4$$^+$).

Example 30

1-ethoxythiocarbonylsulphanyl-2,2,2-trifluoro-ethyl ester of benzoic acid

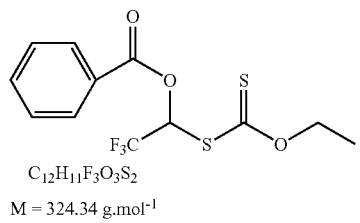

$C_{12}H_{11}F_3O_3S_2$

M = 324.34 g.mol$^{-1}$

Reaction:
The salt of potassium ethylxanthogenate (4.61 g, 46.2 mmol) is added to a solution of 2,2,2-trifluoro-1-methoxy-ethanol (3 g, 23.1 mmol) in acetone (15 ml). The reaction admixture is cooled to 0° C. and sulphuric acid (1.24 ml, 23.1 mmol) is added drop by drop. After one hour at 0° C., the reaction admixture is concentrated at reduced pressure. The residue is placed in ether, washed in water, then with an aqueous solution saturated with potassium carbonate, dried and concentrated again at reduced pressure.

This residue is then placed in dichloromethane (5 ml) and cooled to 0° C. Benzoic anhydride (6.27 g, 27.7 mmol), DMAP (4-dimethylaminopyridine) (845 mg, 6.93 mmol), and triethylamine (5.51 ml, 39.3 mmol) are added drop by drop.

After 3 hours at 0° C., the reaction admixture is concentrated at reduced pressure, placed in dichloromethane, washed in water and then with an aqueous solution saturated with ammonium chloride, dried and concentrated again at reduced pressure.

Purification:
Chromatography over silica gel (ethyl acetate-petroleum ether 5/95)
Product:
Dark yellow oil.
Yield:
58%
$^1$HNMR ($\delta$, ppm) (CDCl$_3$, 400 MHz)
1.30 (t, J=6.2 Hz, 3H, CH$_2$CH$_3$); 3.86-3.91 (m, 1H, CH$_3$CH$_2$); 3.96-4.01 (m, 1H, CH$_3$CH$_2$); 6.28 (q, J=4.0 Hz, 1H, CF$_3$CH); 7.50 (t, J=8.0 Hz, 2H$_{Ar}$, CH$_{Ar}$=CH$_{Ar}$=CH$_{Ar}$Cq$_{Ar}$); 7.65 (t, J=7.6 Hz, 1H$_{Ar}$,CH$_{Ar}$=CH$_{Ar}$=CH$_{Ar}$Cq$_{Ar}$); 8.13 (t, 2H$_{Ar}$, J=7.2 Hz, CH$_{Ar}$=CH$_{Ar}$=CH$_{Ar}$Cq$_{Ar}$).
$^{13}$CNMR ($\delta$, ppm) (CDCl$_3$, 100 MHz)
14.3 (CH$_3$CH$_2$); 68.5 (CH$_2$CH$_3$); 90.0 (q, J=39 Hz, CF$_3$CH); 120.0 (q, J=279 Hz, CF$_3$); 127.3 (2×CH$_{Ar}$); 128.2 (2×CH$_{Ar}$); 129.8 (CH$_{Ar}$); 133.5 (C$_{qAr}$); 164.3 (C=O); 214.1 (C=S).

IR ($\nu$, cm$^{-1}$) (CCl$_4$)
2984; 2929; 1739 (C=O); 1601; 1452; 1290; 1262; 1193; 1169 (C=S); 1113; 1078; 1062; 1025; 988.
Mass (IC, NH3)
325 (MH$^+$), 342 (MNH$_4$$^+$).

Radical Additions

Examples of the Method for Preparing Compounds Having the Formula (IIB)

Example 31

O-ethyl and S-[3-acetoxy-1-(1,3-dioxo-1,3-dihydro-isoindol-2-ylmethyl)-4,4,4-trifluoro-butyl]diester of dithiocarbonic acid

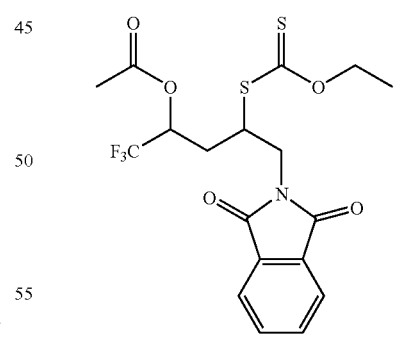

$C_{18}H_{18}F_3NO_5S_2$

M = 449.47 g.mol$^{-1}$

Reaction:
Carried out according to the general operating method with 337 mg (1.29 mmol) of xanthate of example 29 and 481 mg (2.57 mmol) of allyl phthalimide in 1,2-dichloroethane (3 ml). The reaction is terminated after the addition of 15% of LP (26 mg) and 4 hours 30 minutes under reflux.

Purification:
Chromatography over silica gel (ethyl acetate-petroleum ether 1/9 then 2/8).

Product:
Pale yellow oil.
Yield:
78% (admixture of 2 diastereoisomers at a ratio of 1/1)
$^1$HNMR (δ, ppm) (CDCl$_3$, 400 MHz) 1.22 (2t, J=7.0 Hz, 3H, CH$_2$CH$_3$); 1.38-1.42 (m, 2H, CF$_3$CH(OAc)CH$_2$); 2.18 (s, 1.5H, COCH$_3$); 2.22 (s, 1.5H, COCH$_3$); 3.98-4.02 (m, 2H, CH$_2$N); 4.21-4.24 (m, 0.5H, CHS); 4.52 (q, J=7.0 Hz, 1H, CH$_3$CH$_2$); 4.54 (q, J=7.0 Hz, 1H, CH$_3$CH$_2$); 4.54-4.57 (m, 0.5H, CHS); 5.63-5.66 (m, 1H, CF$_3$CH); 7.70-7.73 (m, 2H, H$_{Ar.}$(C$_q$CH=CH)); 7.79-7.84 (m, 2H, H$_{Ar.}$(C$_q$CH=CH)).
$^{13}$CNMR (δ, ppm) (CDCl$_3$, 100 MHz)
12.2 (0.5×CH$_3$CH$_2$); 12.3 (0.5×CH$_3$CH$_2$); 20.0 (0.5×CH$_3$CO); 21, (0.5×CH$_3$CO); 30.2 (0.5×CF$_3$CH(OAc)CH$_2$); 30.4 (0.5×CF$_3$CH(OAc)CH$_2$); 39.8 (0.5×CH$_2$N); 40.2 (0.5×CH$_2$N); 43.8 (0.5×CHS); 44.1 (0.5×CHS); 63.5 (q, J=35 Hz, 0.5×CF$_3$CH); 63.7 (q, J=35 Hz, 0.5×CF$_3$CH); 69.9 (0.5×CH$_2$CH$_3$); 69.9 (0.5×CH$_2$CH$_3$); 121.6 (CH$_{Ar.}$(C$_q$CH=CH)); 121.6 (CH$_{Ar.}$(C$_q$CH=CH)); 124.6 (q, J=272 Hz, 0.5×CF$_3$); 124.9 (q, J=280 Hz, 0.5×CF$_3$); 130.8 (Cq$_{Ar.}$); 132.2 (Cq$_{Ar.}$); 165.3 (2×CH$_{Ar.}$(C$_q$CH=CH)); 167.0 (C=O$_{Ar.}$); 167.0 (C=O$_{Ar.}$); 168.0 (0.5×C=O); 168.0 (0.5×C=O); 212.0 (0.5×C=S); 212.5 (0.5×C=S).
IR (ν, cm$^{-1}$) (CCl$_4$)
2982; 2928; 1766 (C=O); 1723 (C=O); 1615; 1468; 1430; 1392; 1371; 1283; 1213; 1146; 1112; 1049.
Mass (IC, NH3)
450 (MH$^+$); 467 (MNH$_4^+$).

|  |  | Element: | |
|---|---|---|---|
|  |  | Carbon | Hydrogen |
| Microanalysis | Calculated (%) | 48.10 | 4.04 |
|  | Actual (%) | 48.06 | 4.09 |

Example 32

O-ethyl and S-(3-acetoxy-4,4,4-trifluoro-1-trimethyl-silanylmethyl-butyl) ester of dithiocarbonic acid

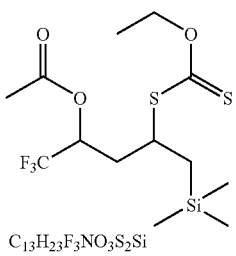

C$_{13}$H$_{23}$F$_3$NO$_3$S$_2$Si
M = 376.54 g.mol$^{-1}$

Reaction:
Carried out according to the general operating method with 300 mg (1.14 mmol) of xanthate of example 29 and 392 mg (3.43 mmol) of allyltrimethylsilane in 1,2-dichloroethane (4 ml). The reaction is terminated after the addition of 5% of LP (22 mg) and 1 hour 45 minutes under reflux.
Purification:
Chromatography over silica gel (ethyl acetate-petroleum ether 1/9 then 2/8).

Product:
White crystals.
Yield:
80% (admixture of 2 diastereoisomers at a ratio of 2/3)
$^1$HNMR (δ, ppm) (CDCl$_3$, 400 MHz)
0.08 (s, 3.6H, Si(CH$_3$)$_3$); 0.09 (s, 5.4H, Si(CH$_3$)$_3$); 0.83-1.15 (m, 2H, CH$_2$Si(CH$_3$)$_3$); 1.42 (t, J=6.4 Hz, 3H, CH$_2$CH$_3$); 2.03-2.26 (m, 2H, CF$_3$CH(OAc)CH$_2$); 2.15 (s, 1.2H, COCH$_3$); 2.17 (s, 1.8H, COCH$_3$); 3.72 (m, 0.4H, CHS); 3.95 (m, 0.6H, CHS); 4.65 (q, J=6.4 Hz, 2H, CH$_3$CH$_2$); 5.39-5.45 (m, 0.4H, CF$_3$CH); 5.48-5.52 (m, 0.6H, CF$_3$CH).
$^{13}$CNMR (δ, ppm) (CDCl$_3$, 100 MHz)
−0.7 (1.2×Si(CH$_3$)$_3$); −0.7 (1.8×Si(CH$_3$)$_3$); 13.8 (0.4×CH$_3$CH$_2$); 13.8 (0.6×CH$_3$CH$_2$); 19.7 (0.4×CH$_2$OAcCHCF$_3$); 19.8 (0.6×CH$_2$OAcCHCF$_3$); 22.1 (0.4×CH$_3$CO); 22.5 (0.6×CH$_3$CO); 34.9 (0.4×CH$_2$SiMe$_3$); 35.2 (0.6×CH$_2$SiMe$_3$); 43.4 (0.4×CHS); 43.7 (0.6×CHS); 68.1 (q, J=32 Hz, 0.4×CF$_3$CH); 68.2 (q, J=32 Hz, 0.6×CF$_3$CH); 70.3 (0.4×CH$_2$CH$_3$); 70.5 (0.6×CH$_2$CH$_3$); 122.3 (q, J=281 Hz, 0.4×CF$_3$); 125.4 (q, J=281 Hz, 0.6×CF$_3$); 170.1 (0.4×C=O); 170.3 (0.6×C=O); 212.1 (0.4×C=S); 213.2 (0.6×C=S).
IR (ν, cm$^{-1}$)(CCl$_4$)
2956; 2927; 2855; 2355; 1764 (C=O); 1441; 1371; 1285; 1268; 1214; 1182; 1140; 1112; 979; 938.
Mass (IC, NH3)
377 (MH$^+$); 394 (MNH$_4^+$).
MP
120° C. (ether)

Example 33

3-acetoxy-1-ethoxythiocarbonylsulphanyl-4,4,4-trifluoro-butyl ester of acetic acid

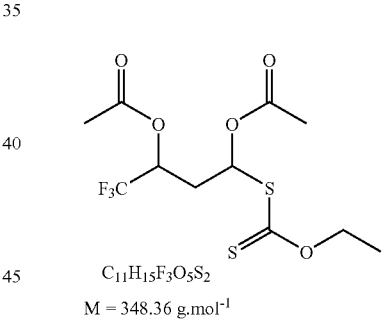

C$_{11}$H$_{15}$F$_3$O$_5$S$_2$
M = 348.36 g.mol$^{-1}$

Reaction: Carried out according to the general operating method with 200 mg (0.77 mmol) of xanthate of example 29 and 77 μL (0.92 mmol) of vinyl acetate in 1,2-dichloroethane (1.5 ml). The reaction is terminated after the addition of 5% of LP (15 mg) and 1 hour 30 minutes under reflux.
Purification:
Chromatography over silica gel (ethyl acetate-petroleum ether 1/9).
Product:
Thick pale yellow oil.
Yield:
79% (admixture of 2 diastereoisomers at a ratio of 1/1)
$^1$HNMR (δ, ppm) (CDCl$_3$, 400 MHz)
1.48 (t, J=6.7 Hz, 1.5H, CH$_2$CH$_3$); 1.49 (t, J=6.7 Hz, 1.5H, CH$_2$CH$_3$); 2.12 (s, 3H, COCH$_3$); 2.23 (s, 3H, COCH$_3$); 2.39-2.46 (m, 1H, CF$_3$CH(OAc)CH$_2$); 2.49-2.52 (m, 1H, CF$_3$CH (OAc)CH$_2$); 4.60 (q, J=6.7 Hz, 1H, CH$_3$CH$_2$); 4.61 (q, J=6.7 Hz, 1H, CH$_3$CH$_2$); 5.43-5.48 (m, 0.5H, CF$_3$CH); 5.49-5.52 (m, 0.5H, CF$_3$CH); 6.68-6.73 (m, 0.5H, CHS); 6.79-6.84 (m, 0.5H, CHS).

$^{13}$CNMR (δ, ppm) (CDCl$_3$, 100 MHz)

13.4 (0.5×CH$_3$CH$_2$); 13.6 (0.5×CH$_3$CH$_2$); 20.8 (0.5×CH$_3$CO); 20.9 (0.5×CH$_3$CO); 22.9 (0.5×CH$_3$CO); 23.1 (0.5×CH$_3$CO); 33.1 (0.5×CH$_2$CHS); 33.5 (0.5×CH$_2$CHS); 47.6 (q, J=32 Hz, 0.5×CF$_3$CH); 47.8 (q, J=32 Hz, 0.5×CF$_3$CH); 70.5 (0.5×CH$_2$CH$_3$); 70.7 (0.5×CH$_2$CH$_3$); 77.2 (0.5×CHS); 77.9 (0.5×CHS); 125.2 (q, J=281 Hz, 0.5×CF$_3$); 125.7 (q, J=281 Hz, 0.5×CF$_3$); 168.9 (0.5×OC=O); 169.8 (0.5×OC=O); 170.6 (0.5×C=O); 170.8 (0.5×C=O); 209.2 (0.5×C=S); 209.7 (0.5×C=S).

IR (ν, cm$^{-1}$) (CCl$_4$)

3511; 2983; 2938; 2869; 2412; 1764 (C=O); 1720 (C=O); 1641; 1430; 1398; 1371; 1284; 1228; 1146; 1111; 1086; 1048; 1016.

Mass (IC, NH3)

289 (M H$^+$—AcOH); 349 (MH$^+$); 366 (MNH$_4^+$).

Example 34

O-ethyl and S-(3-acetoxy-1-diethoxymethyl-4,4,4-trifluoro-pentyl) diester of dithiocarbonic acid

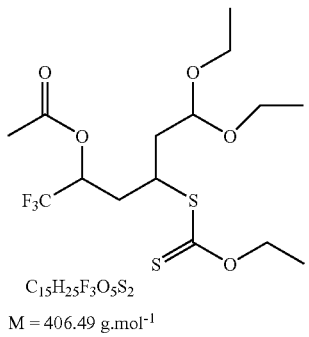

C$_{15}$H$_{25}$F$_3$O$_5$S$_2$

M = 406.49 g.mol$^{-1}$

Reaction:

Carried out according to the general operating method with 200 mg (0.76 mmol) of xanthate of example 29 and 220 mg (1.5 mmol) of 4,4-diethoxy-butene in 1,2-dichloroethane (2 ml). The reaction is terminated after the addition of 5% of LP (15 mg) and 1 hour 30 minutes under reflux.

Purification:

Chromatography over silica gel (ethyl acetate-petroleum ether 1/9).

Product:

Thick pale yellow oil.

Yield:

82% (admixture of 2 diastereoisomers at a ratio of 1/1)

$^1$HNMR (δ, ppm) (CDCl$_3$, 400 MHz)

1.20 (t, J=7.0 Hz, 6H, CH(OCH$_2$CH$_3$)$_2$); 1.25 (t, J=7.0 Hz, 3H, CH$_2$CH$_3$); 1.42 (dd, J$_1$=7.5 Hz, J$_2$=9.1 Hz, 2H, CH—CH$_2$—CH(OCH$_2$CH$_3$)$_2$); 2.25-2.28 (m, 2H, CF$_3$CH (OAc)CH$_2$); 3.51-3.55 (m, 2H, CH$_3$CH$_2$O); 3.59-3.65 (m, 2H, CH$_3$CH$_2$O); 4.62-4.67 (m, 2H, CH$_3$CH$_2$O); 5.05 (dd, J$_1$=9.2 Hz, J$_2$=12.0 Hz, 0.5H, CH(OEt)$_2$); 5.12 (dd, J$_1$=9.2 Hz, J$_2$=12.0 Hz, 0.5H, CH(OEt)$_2$); 5.47-5.52 (m, 0.5H, CHS); 5.61-5.64 (m, 0.5H, CHS); 5.89-5.93 (m, 1H, CF$_3$CH).

$^{13}$CNMR (δ, ppm) (CDCl$_3$, 100 MHz)

13.9 (CH$_3$CH$_2$); 14.5 (CH$_3$CH$_2$); 16.2 (0.5×CH$_3$CH$_2$); 17.2 (0.5×CH$_3$CH$_2$); 21.0 (0.5×CH—CH$_2$—CH(OCH$_2$CH$_3$)$_2$)); 21.2 (0.5×CH—CH$_2$—CH(OCH$_2$CH$_3$)$_2$)); 24.3 (0.5×CH$_3$CO); 24.5 (0.5×CH$_3$CO); 30.2 (0.5×CF$_3$CH(OAc) CH$_2$); 30.6 (0.5×CF$_3$CH(OAc)CH$_2$); 43.1 (q, J=30 Hz, 0.5×CF$_3$CH); 43.5 (q, J=30 Hz, 0.5×CF$_3$CH); 51.2 (0.5×CHS); 51.5 (0.5×CHS); 61.8 (0.5×CH$_2$CH$_3$); 62.1 (0.5×CH$_2$CH$_3$); 64.0 (0.5×CH$_2$CH$_3$); 64.2 (0.5×CH$_2$CH$_3$); 69.7 (0.5×CH$_2$CH$_3$); 69.8 (0.5×CH$_2$CH$_3$); 100.9 (0.5×CH(OEt)$_2$); 101.3 (0.5×CH(OEt)$_2$); 122.9 (q, J=Hz, 0.5×CF$_3$); 123.1 (q, J=283 Hz, 0.5×CF$_3$); 158.3 (0.5×C=O); 158.6 (0.5×C=O); 214.1 (0.5×C=S); 214.4 (0.5×C=S).

IR (ν, cm$^{-1}$)(CCl$_4$)

2978; 2928; 2336; 1764 (C=O); 1442; 1372; 1283; 1215; 1182; 1142; 1112; 1052.

Mass (IC, NH3)

363 (MH$^+$-EtOH).

Example 35

O-ethyl and S-(3-acetoxy-1-cyanomethyl-4,4,4-trifluoro)butyl ester of dithiocarbonic acid

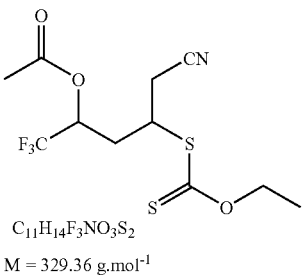

C$_{11}$H$_{14}$F$_3$NO$_3$S$_2$

M = 329.36 g.mol$^{-1}$

Reaction:

Carried out according to the general operating method with 200 mg (0.77 mmol) of xanthate of example 29 and 109 μL (2.31 mmol) of but-3-enenitrile in 1,2-dichloroethane (2 ml). The reaction is terminated after the addition of 10% of LP (31 mg) and 3 hours under reflux.

Purification:

Chromatography over silica gel (ethyl acetate-petroleum ether 5/95).

Product:

Thick pale yellow oil.

Yield:

92% (admixture of 2 diastereoisomers at a ratio of 3/2)

$^1$HNMR (δ, ppm) (CDCl$_3$, 400 MHz)

1.41 (t, J=7.0 Hz, 1.8H, CH$_2$CH$_3$); 1.46 (t, J=7.0 Hz, 1.2H, CH$_2$CH$_3$); 2.15 (s, 1.8H, COCH$_3$); 2.21 (s, 1.2H, COCH$_3$); 2.08-2.31 (m, 2H, CF$_3$CH(OAc)CH$_2$); 2.82-3.07 (m, 2H, CH$_2$CN); 3.90-3.95 (m, 0.6H, CHS); 4.03-4.07 (m, 0.4H, CHS); 4.61 (q, J=7.0 Hz, 1.2H, CH$_3$CH$_2$); 4.63 (q, J=7.0 Hz, 0.8H, CH$_3$CH$_2$); 5.41-5.45 (m, 0.6H, CF$_3$CH); 5.57-5.60 (m, 0.4H, CF$_3$CH).

$^{13}$CNMR (δ, ppm) (CDCl$_3$, 100 MHz)

13.7 (CH$_3$CH$_2$); 20.1 (0.6×CF$_3$CH(OAc)CH$_2$); 22.3 (CH$_3$CO); 24.2 (0.4×CF$_3$CH(OAc)CH$_2$); 30.8 (0.6×CH$_2$CN); 31.5 (0.4×CH$_2$CN); 42.0 (0.6×CHS); 42.4 (0.4×CHS); 66.4 (q, J=30 Hz, 0.6×CF$_3$CH); 66.7 (q, J=30 Hz, 0.4×CF$_3$CH); 70.6 (0.6×CH$_2$CH$_3$); 70.9 (0.4×CH$_2$CH$_3$); 115.9 (0.6×CN); 116.1 (0.4×CN); 121.6 (q, J=281 Hz, 0.6× CF$_3$); 124.9 (q, J=281 Hz, 0.4×CF$_3$); 168.5 (0.6×C=O); 169.1 (0.4×C=O); 210.5 (0.6×C=S); 210.9 (0.4×C=S).

IR (ν, cm$^{-1}$)(CCl$_4$)

2928; 1764 (C=O); 1372; 1279; 1210; 1186; 1111; 1083; 1049; 1006; 969.

Mass (IC, NH3)

330 (MH$^+$); 347 (MNH$_4^+$).

Example 36

O-ethyl and S-1-(2-acetoxy-3,3,3-trifluoro-propyl)-4-oxo-pentyl diester of dithiocarbonic acid

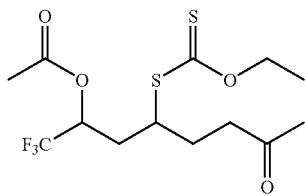

$C_{13}H_{19}F_3O_4S_2$ $M = 360.42$ g.mol$^{-1}$

Reaction:

Carried out according to the general operating method with 200 mg (0.76 mmol) of xanthate according to example 29 and 225 mg (2.28 mmol) of hex-5-en-2-one in 1,2-dichloroethane (2 ml). The reaction is terminated after the addition of 10% of LP (30 mg) and 3 hours under reflux.

Purification:

Chromatography over silica gel (ethyl acetate-petroleum ether 5/95).

Product:

Pale yellow oil.

Yield

88% (admixture of 2 diastereoisomers at a ratio of 3/2)

$^1$HNMR (δ, ppm) (CDCl$_3$, 400 MHz)

1.42 (t, J=7.0 Hz, 1.8H, CH$_2$CH$_3$); 1.47 (t, J=7.0 Hz, 1.2H, CH$_2$CH$_3$); 1.69-1.74 (m, 1.2H, CH$_2$COCH$_3$); 1.78-1.82 (m, 0.8H, CH$_2$COCH$_3$); 1.98 (s, 1.8H, COCH$_3$); 2.10 (s, 1.8H, COCH$_3$); 2.11 (s, 1.2H, COCH$_3$); 2.12 (s, 1.2H, COCH$_3$); 2.02-2.31 (m, 2H, CH$_2$CH$_2$COCH$_3$); 2.51-2.70 (m, 2H, CH$_2$CHS); 3.68-3.74 (m, 0.6H, CHS); 3.91-3.95 (m, 0.4H, CHS); 4.58 (q, J=7.0 Hz, 1.2H, CH$_3$CH$_2$); 4.64 (q, J=7.0 Hz, 0.8H, CH$_3$CH$_2$); 5.39-5.51 (m, 0.6H, CF$_3$CH); 5.49-5.54 (m, 0.4H, CF$_3$CH).

$^{13}$CNMR (δ, ppm) (CDCl$_3$, 100 MHz)

13.3 (CH$_3$CH$_2$); 20.3 (CH$_3$CO); 24.4 (0.6×CH$_2$COCH$_3$); 25.7 (0.4×CH$_2$COCH$_3$); 29.6 (0.6×CH$_3$CO); 31.5 (0.4× CH$_3$CO); 32.5 (0.6×CH$_2$CH$_2$COCH$_3$); 33.5 (0.4× CH$_2$CH$_2$COCH$_3$); 39.8 (0.6×CH$_2$CHS); 40.0 (0.4× CH$_2$CHS); 45.9 (0.6×CHS); 46.4 (0.4×CHS); 66.7 (q, J=32 Hz, 0.6×CF$_3$CH); 67.0 (q, J=30 Hz, 0.4×CF$_3$CH); 69.9 (0.6× CH$_2$CH$_3$); 70.3 (0.4×CH$_2$CH$_3$); 124.5 (q, J=281 Hz, 0.6× CF$_3$); 124.6 (q, J=281 Hz, 0.4×CF$_3$); 168.6 (0.6×OC=O); 169.2 (0.4×OC=O); 206.7 (0.6×C=O); 206.9 (0.4×C=O); 212.4 (0.6×C=S); 213.2 (0.4×C=S).

IR (ν, cm$^{-1}$)(CCl$_4$)

2983; 2926; 2335; 1764 (OC=O); 1721 (NC=O); 1441; 1371; 1283; 1214; 1182; 1141; 1053; 909.

Mass (IC, NH3)

361 (MH$^+$), 378 (MNH$_4^+$).

|  |  | Element: | |
| --- | --- | --- | --- |
|  |  | Carbon | Hydrogen |
| Microanalysis | Calculated (%) | 44.91 | 5.65 |
|  | Actual (%) | 44.91 | 5.66 |

Example 37

4-[4-bromo-phenyl)-methanesulphonyl-amino]-3-ethoxycarbonyl-sulphanyl-1-trifluoromethyl-butyl] ester of acetic acid

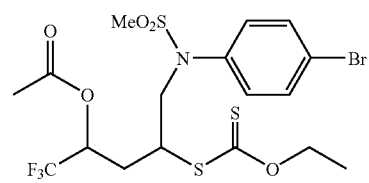

$C_{17}H_{21}BrF_3NO_3S_3$ $M = 552.42$ g.mol$^{-1}$

Reaction:

Carried out according to the general operating method with 1.54 g (5.88 mmol) of xanthate of example 29 and 2.55 mg (8.88 mmol) of N-allyl-N-(4-bromophenyl)-methanesulphonamide in 1,2-dichloroethane (8 ml). The reaction is terminated after the addition of 20% of LP (468 mg) and 8 hours under reflux.

Purification:

Chromatography over silica gel (ethyl acetate-petroleum ether 1/9).

Product:

Pale yellow oil.

Yield:

71% (2 diastereoisomers at a ratio of 1/1)

First Diastereoisomer $^1$HNMR (δ, ppm) (CDCl$_3$, 400 MHz)

1.28 (t, J=7.0 Hz, 3H, CH$_2$CH$_3$); 1.96 (s, 3H, COCH$_3$); 2.29-2.35 (m, 2H, CF$_3$CH(OAc)CH$_2$); 2.93 (s, 3H, SO$_2$CH$_3$); 3.67-3.73 (m, 1H, CHS); 3.94-3.99 (m, 2H, CH$_2$N); 4.31 (q, J=7.0 Hz 2H, CH$_3$CH$_2$); 4.59-4.64 (m, 1H, CF$_3$CH); 7.23 (d, J=8.0 Hz, 2H, H$_{Ar}$(HC=CNSO$_2$)); 7.53 (d, J=8.0 Hz, 2H, H$_{Ar}$(HC=CBr)).

$^{13}$CNMR (δ, ppm) (CDCl$_3$, 100 MHz) 13.6 (CH$_3$CH$_2$); 24.8 (CH$_3$CO); 31.3 (CF$_3$CH(OAc)CH$_2$); 31.6 (CH$_3$SO$_2$); 34.0 (CHS); 48.6 (q, J=30 Hz, CF$_3$CH); 52.3 (CH$_2$N); 70.0 (CH$_2$CH$_3$); 122.0 (Cq$_{Ar}$Br); 129.9 (q, J=281 Hz, CF$_3$); 131.4 (CH$_{Ar}$(HC=CNSO$_2$)); 133.53 (CH$_{Ar}$(HC=CNSO$_2$)); 133.5 (2×CH$_{Ar}$(HC=CBr)); 146.5 (Cq$_{Ar}$NSO$_2$); 180.0 (C=O); 213.1 (C=S).

IR (ν, cm$^{-1}$)(CCl$_4$)

2983; 1705 (C=O); 1439; 1358; 1226; 1184; 1162; 1135; 1110; 1039; 1008.

Mass (IC, NH3)

553 (MH$^+$); 570 (MNH$_4^+$).

|  |  | Element: | |
| --- | --- | --- | --- |
|  |  | Carbon | Hydrogen |
| Microanalysis | Calculated (%) | 36.96 | 3.83 |
|  | Actual (%) | 36.75 | 3.89 |

Second Diastereoisomer $^1$HNMR (δ, ppm) (CDCl$_3$, 400 MHz)

1.25 (t, J=7.0 Hz, 3H, CH$_2$CH$_3$); 1.96 (s, 3H, COCH$_3$); 2.24-2.31 (m, 2H, CF3CH(OAc)CH$_2$); 2.87 (s, 3H, SO$_2$CH$_3$);

3.51-3.59 (m, 1H, CHS); 3.78-3.83 (m, 2H, CH$_2$N); 4.27 (q, J=7.0 Hz 2H, CH$_3$CH$_2$); 4.61-4.65 (m, 1H, CF$_3$CH); 7.18 (d, J=8.0 Hz, 2H, H$_{Ar}$(HC=CNSO$_2$)); 7.51 (d, J=8.0 Hz, 2H, H$_{Ar}$(HC=CBr)).

$^{13}$CNMR (δ, ppm) (CDCl$_3$, 100 MHz)

13.5 (CH$_3$CH$_2$); 22.5 (CH$_3$CO); 30.0 (CF$_3$CH(OAc)CH$_2$); 31.5 (CH$_3$SO$_2$); 33.9 (CHS); 48.6 (q, J=30 Hz, CF$_3$CH); 51.6 (CH$_2$N); 76.7 (CH$_2$CH$_3$); 122.0 (Cq$_{Ar}$Br); 129.5 (q, J=281 Hz, CF$_3$); 131.2 (CH$_{Ar}$(HC=CNSO$_2$)); 133.5 (CH$_{Ar}$(HC=CNSO$_2$)); 133.5 (2×CH$_{Ar}$(HC=CBr)); 146.1 (Cq$_{Ar}$NSO$_2$); 179.9 (C=O); 213.0 (C=S).

IR (ν, cm$^{-1}$)(CCl$_4$)

2987; 1709 (C=O); 1442; 1354; 1221; 1178; 1157; 1117; 1035; 1001.

Mass (IC, NH3)

553 (MH$^+$); 570 (MNH$_4^+$).

|  |  | Element: | |
|---|---|---|---|
|  |  | Carbon | Hydrogen |
| Microanalysis | Calculated (%) | 36.96 | 3.83 |
|  | Actual (%) | 36.87 | 3.74 |

Conversions of the Adducts

Example 38

4-acetoxy-5,5,5-trifluoro-pent-1-ene

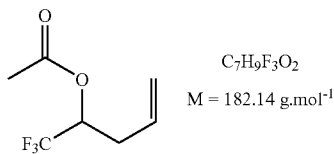

C$_7$H$_9$F$_3$O$_2$

M = 182.14 g.mol$^{-1}$

Reaction: A normal solution of tetrabutylammonium fluoride in THF (265 ml, 1.06 mmol) is added to a solution of xanthate of example 32 (200 mg, 0.53 mmol) in tetrahydrofuran (3 ml). After 2 hours at ambient temperature, the admixture is concentrated at reduced pressure before being purified.

Purification:

Chromatography over silica gel (ethyl acetate-petroleum ether 1/9).

Product:

Pale yellow oil.

Yield:

74%.

$^1$HNMR (δ, ppm) (CDCl$_3$, 400 MHz)

2.14 (s, 3H, OCOCH$_3$); 3.08-3.14 (m, 2H, CH$_2$); 3.65-3.72 (m, 1H, CH=CH$_2$); 4.43-4.47 (m, 2H, CH=CH$_2$); 4.58-4.63 (m, 1H, CF$_3$CH).

$^{13}$CNMR (δ, ppm) (CDCl$_3$, 100 MHz)

19.7 (CH$_2$); 22.3 (CH$_3$CO); 67.5 (q, J=30 Hz, CF$_3$CH); 69.8 (CH=CH$_2$); 102.5 (CH=CH$_2$); 123.8 (q, J=281 Hz, CF$_3$); 170.2 (C=O).

IR (ν, cm$^{-1}$)(CCl$_4$)

2830; 2340; 1765 (C=O); 1431; 1385; 1272; 1195; 1128; 985; 927.

Mass (IC, NH3)

183 (MH$^+$); 200 (MNH$_4^+$).

|  |  | Element: | |
|---|---|---|---|
|  |  | Carbon | Hydrogen |
| Microanalysis | Calculated (%) | 46.06 | 4.77 |
|  | Actual (%) | 47.16 | 4.98 |

Example 39

1-[5-bromo-1-methanesulphonyl-2,3-dihydro-1H-indol-3-ylmethyl)-2,2,2-trifluoro-ethyl]ester of acetic acid

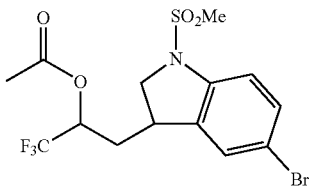

C$_{14}$H$_{15}$BrF$_3$NO$_4$S

M = 430.24 g.mol$^{-1}$

Reaction:

LP is added, at a rate of 10 mol % (21 mg, 0.054 mmol) every hour, to a solution of the xanthate adduct of example 37 (300 mg, 0.54 mmol) in 1,2-dichloroethane (4 ml), which solution has been degassed beforehand at reflux under argon. The reaction is stopped after 13 hours 30 minutes under reflux and the addition of 120% of LP (258 mg, 0.65 mmol). The reaction medium is then brought to ambient temperature and concentrated at reduced pressure before being purified.

Purification:

Chromatography over silica gel (ethyl acetate-petroleum ether 1/9).

Product:

Pale yellow oil.

Yield:

88% (admixture of 2 diastereoisomers at a ratio of 1/1)

$^1$HNMR (δ, ppm) (CDCl$_3$, 400 MHz)

1.78-1.87 (m, 0.5H, CF$_3$CH(OAc)CH$_2$); 1.86-1.93 (m, 0.5H, CF$_3$CH(OAc)CH$_2$); 1.98 (s, 1.5H, COCH$_3$); 2.01 (s, 1.5H, COCH$_3$); 2.19-2.23 (m, 0.5H, CF$_3$CH(OAc)CH$_2$); 2.22-2.26 (m, 0.5H, CF$_3$CH(OAc)CH$_2$); 3.04 (s, 1.5H, SO$_2$CH$_3$); 3.06 (s, 1.5H, SO$_2$CH$_3$); 3.65-3.70 (m, 0.5H, CHCH$_2$N); 3.71-3.74 (m, 0.5H, CHCH$_2$N); 3.87 (dd, J$_1$=10.1 Hz, J$_2$=9.9 Hz, 0.5H, CH$_2$N); 3.90 (dd, J$_1$=10.1 Hz, J$_2$=10.0 Hz, 0.5H, CH$_2$N); 4.08 (dd, J$_1$=10.0 Hz, J$_2$=9.9 Hz, 0.5H, CH$_2$N); 4.10 (dd, J$_1$=10.0 Hz, J$_2$=10.0 Hz, 0.5H, CH$_2$N); 4.79-4.85 (m, 0.5H, CF$_3$CH); 4.87-4.90 (m, 0.5H, CF$_3$CH); 7.25 (d, J=8.5 Hz, 0.5H, H$_{Ar}$(HC=CNSO$_2$)); 7.27 (d, J=8.6 Hz, 0.5H, H$_{Ar}$(HC=CNSO$_2$)); 7.40 (d, J=8.5 Hz, 0.5H, H$_{Ar}$(HC=CBr)); 7.42 (d, J=8.6 Hz, 0.5H, H$_{Ar}$(HC=CBr)); 7.70 (s, 0.5H, H$_{Ar}$(HC=CBr)); 7.72 (s, 0.5H, H$_{Ar}$(HC=CBr)).

$^{13}$CNMR (δ, ppm) (CDCl$_3$, 100 MHz)

22.8 (CH$_3$CO); 32.8 (0.5×CF$_3$CH(OAc)CH$_2$); 33.1 (0.5×CF$_3$CH(OAc)CH$_2$); 34.4 (0.5×CH$_2$N); 34.6 (0.5×CH$_2$N); 36.8 (0.5×CH$_3$SO$_2$); 36.9 (0.5×CH$_3$SO$_2$); 48.5 (q, J=30 Hz, 0.5×CF$_3$CH); 48.7 (q, J=30 Hz, 0.5×CF$_3$CH); 55.8 (0.5×CHCH$_2$N); 56.3 (0.5×CHCH$_2$N); 115.5 (0.5×CH$_{Ar}$=CNSO$_2$); 115.7 (0.5×CH$_{Ar}$=CNSO$_2$); 116.3 (0.5×Cq$_{Ar}$Br); 116.6 (0.5×Cq$_{Ar}$Br); 126.8 (q, J=Hz, 0.5×CF$_3$); 127.0 (q, J=281 Hz, 0.5×CF$_3$); 128.3 (0.5×CH$_{Ar}$=CBr);

128.5 (0.5×CH$_{Ar}$=CBr); 132.0 (0.5×CH$_{Ar}$=CBr); 132.1 (0.5×CH$_{Ar}$=CBr); 137.5 (0.5×Cq$_{Ar}$NSO$_2$); 137.8 (0.5× Cq$_{Ar}$NSO$_2$); 142.8 (0.5×Cq$_{Ar}$); 143.0 (0.5×Cq$_{Ar}$); 170.9 (0.5×C=O); 171.3 (0.5×C=O).

IR (ν, cm$^{-1}$) (CCl$_4$)

1759 (C=O); 1549; 1352; 1307; 1269; 1214; 1161; 1128; 1112.

Mass (IC, NH3)

431 (MH$^+$); 448 (MNH$_4{}^+$).

|  |  | Element: | |
| --- | --- | --- | --- |
|  |  | Carbon | Hydrogen |
| Microanalysis | Calculated (%) | 39.08 | 3.51 |
|  | Actual (%) | 39.17 | 3.63 |

Examples of Methods for Preparing Compounds Having the Formula (VIIIB)

Example 40

2-benzoxy-3,3,3-trifluoro-1-trifluoromethyl-propyl ester of benzoic acid

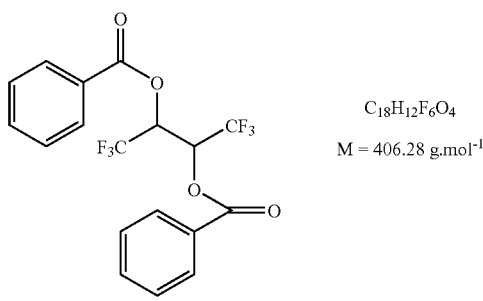

C$_{18}$H$_{12}$F$_6$O$_4$
M = 406.28 g.mol$^{-1}$

Reaction:

LP is added, at a rate of 10 mol % (52 mg, 0.13 mmol) every 10 minutes, to a solution of xanthate of example 30 (430 mg, 1.3 mmol) in chlorobenzene (14 ml), which solution has been degassed beforehand at reflux under argon. The reaction is stopped after 4 hours under reflux and the addition of 140% of LP (724 mg, 1.8 mmol). The reaction medium is then brought to ambient temperature and concentrated at reduced pressure before being purified.

Purification:

By means of precipitation in an admixture of ether-petroleum ether 5/95.

Product:

Colourless solid.

Yield:

65% (admixture of 2 diastereoisomers at a ratio of 1/1)

$^1$HNMR (δ, ppm) (CD$_3$)$_2$SO, 400 MHz)

4.57-4.64 (m, 1H, CF$_3$CH); 4.66-4.69 (m, 1H, CF$_3$CH); 7.31-7.39 (m, 4H$_{Ar}$, CH$_{Ar}$=CH$_{Ar}$=CH$_{Ar}$C$_{qAr}$); 7.48-7.53 (m, 2H$_{Ar}$, CH$_{Ar}$=CH$_{Ar}$=CH$_{Ar}$C$_{qAr}$); 7.77-7.89 (m, 4H$_{Ar}$, CH$_{Ar}$=CH$_{Ar}$=CH$_{Ar}$C$_{qAr}$).

$^{13}$CNMR (δ, ppm) ((CD$_3$)$_2$SO, 400 MHz)

78.4 (q, J=31 Hz, CF$_3$CH); 79.8 (q, J=31 Hz, CF$_3$CH); 117.03 (q, J=283 Hz, CF$_3$); 118.09 (q, J=283 Hz, CF$_3$); 126.4 (2×CH$_{Ar}$); 126.8 (2×CH$_{Ar}$); 129.1 (2×CH$_{Ar}$); 129.3 (2×CH$_{Ar}$); 129.7 (2×CH$_{Ar}$); 131.5 (C$_{qAr}$); 131.8 (C$_{qAr}$); 159.5 (C=O); 160.0 (C=O).

IR (ν, cm$^1$) (nujol)

2976; 1702 (C=O); 1547; 1340; 1301; 1255; 1238; 1181; 1153; 1108.

Mass (IC, NH3)

407 (MH$^+$); 424 (MNH$_4{}^+$).

Examples of the Method for Preparing Compounds Having the Formula (Ic)

Synthesis of 2-trifluoromethylethylchloro xanthate

Example 41

O-ethyl and S-1-chloro-2,2,2-trifluoro-ethyl diester of dithiocarbonic acid a) O-ethyl and S-1-hydroxy-2,2,2-trifluoro-ethyl diester of dithiocarbonic acid

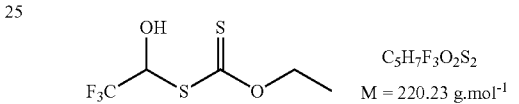

C$_5$H$_7$F$_3$O$_2$S$_2$
M = 220.23 g.mol$^{-1}$

Reaction:

The salt of potassium ethylxanthogenate (737 mg, 4.62 mmol) is added to a solution of 2,2,2-trifluoro-1-methoxyethanol (300 mg, 2.31 mmol) in acetone (5 ml). The reaction admixture is cooled to 0° C. and sulphuric acid (123.6 μL, 2.31 mmol) is added drop by drop. After one hour at 0° C., the reaction admixture is concentrated at reduced pressure. The residue is placed in ether, filtered and concentrated again at reduced pressure.

Product:

Yellow oil.

Yield:

69%

$^1$HNMR (δ, ppm) (CDCl$_3$, 400 MHz)

1.54 (t, J=6.3 Hz, 3H, CH$_2$CH$_3$); 4.71 (q, J=6.3 Hz, 2H, CH$_3$CH$_2$); 6.02 (q, J=5.71 Hz, 1H, CF$_3$CH).

$^{13}$CNMR (δ, ppm) (CDCl$_3$, 100 MHz) 13.7 (CH$_3$CH$_2$); 57.8 (q, J=30 Hz, CF$_3$CH); 71.4 (CH$_2$CH$_3$); 124.4 (q, J=280 Hz, CF$_3$); 207.1 (C=S).

IR (ν, cm$^{-1}$)(CCl$_4$)

2961; 1453; 1314; 1231; 1130; 1052; 1023.

Mass (IC, NH3)

221 (MH$^+$), 238 (MNH$_4{}^+$).

b) O-ethyl and S-1-chloro-2,2,2-trifluoro-ethyl diester of dithiocarbonic acid

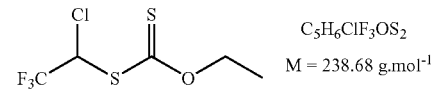

C$_5$H$_6$ClF$_3$OS$_2$
M = 238.68 g.mol$^{-1}$

Reaction:

A solution of alcohol 41a) (1.38 g, 6.3 mmol) and phosphorus pentachloride (1.30 g, 6.3 mmol) is agitated at ambient temperature for 1 hour. After evaporation at reduced pressure, the residue is purified.

Purification:

Chromatography over silica gel (petroleum ether and ethyl acetate 1/9 then 2/8).

Product:

Yellow oil.

Yield:

18%

$^1$HNMR (δ, ppm) (CDCl$_3$, 400 MHz)

1.49 (t, J=6.8 Hz, 3H, CH$_2$CH$_3$); 4.75 (q, J=6.8 Hz, 2H, CH$_3$CH$_2$); 6.27 (q, J=8.4 Hz, 1H, CF$_3$CH).

$^{13}$CNMR (δ, ppm) (CDCl$_3$, 100 MHz)

13.9 (CH$_3$CH$_2$); 22.6 (q, J=35 Hz, CF$_3$CH); 71.5 (CH$_2$CH$_3$); 121.1 (q, J=282 Hz, CF$_3$); 211.1 (C=S).

IR (ν, cm$^{-1}$)(CCl$_4$)

2986; 2939; 1442; 1370; 1344; 1194; 1131; 1032; 868; 823.

Mass (IC, NH$_3$)

238 (M), 240 (M+2); 193 (MH+−EtOH).

|  |  | Element: | |
|---|---|---|---|
|  |  | Carbon | Hydrogen |
| Microanalysis | Calculated (%) | 25.16 | 2.53 |
|  | Actual (%) | 25.19 | 2.51 |

Radical Additions

Examples of Methods for Preparing Compounds Having the Formula (IIC)

The general operating method is as set out above for the preparation of the compounds (IIa).

Example 42

O-ethyl and S-3-chloro-4,4,4-trifluoro-1-trimethylsilanylmethylbutyl diester of dithiocarbonic acid

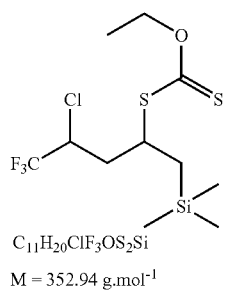

C$_{11}$H$_{20}$ClF$_3$OS$_2$Si

M = 352.94 g.mol$^{-1}$

Reaction:

Carried out according to the general operating method with 133 mg (0.64 mmol) of xanthate of example 41 and 220 mg (2.29 mmol) of allyltrimethylsilane in 1,2-dichloroethane (2 ml). The reaction is terminated after the addition of 5% of LP (13 mg) and 1 hour 30 minutes under reflux.

Purification:

Chromatography over silica gel (ethyl acetate-petroleum ether 1/9).

Product:

Yellow oil.

Yield:

88% (admixture of 2 diastereoisomers at a ratio of 2/3)

$^1$HNMR (δ, ppm) (CDCl$_3$, 400 MHz)

0.12 (s, 3.6H, Si(CH$_3$)$_3$); 0.31 (s, 5.4H, Si(CH$_3$)$_3$); 1.13-1.18 (m, 0.8H, CH$_2$Si(CH$_3$)$_3$); 1.30-1.35 (m, 1.2H, CH$_2$Si (CH$_3$)$_3$); 1.48 (t, J=7.0 Hz, 3H, CH$_2$CH$_3$); 2.08-2.14 (m, 0.8H, CF$_3$CHClCH$_2$); 2.24-2.29 (m, 1.2H, CF$_3$CHClCH$_2$); 4.01-4.08 (m, 0.4H, CHS); 4.10-4.15 (m, 0.6H, CHS); 4.18-4.23 (m, 0.4H, CF$_3$CH); 4.27-4.35 (m, 0.6H, CF$_3$CH); 4.69-4.76 (m, 2H, CH$_3$CH$_2$);

$^{13}$CNMR (δ, ppm) (CDCl$_3$, 100 MHz)

−0.7 (1.2×Si(CH$_3$)$_3$); −0.8 (1.8×Si(CH$_3$)$_3$); 13.9 (CH$_3$CH$_2$); 27.3 (0.4×CH$_2$Si(CH$_3$)$_3$); 28.2 (0.6×CH$_2$Si (CH$_3$)$_3$); 33.3 (0.4×CH$_2$CF$_3$CHCl); 35.5 (0.6× CH$_2$CF$_3$CHCl); 43.3 (0.4×CHS); 47.4 (0.6×CHS); 51.3 (q, J=28 Hz, 0.4×CF$_3$CH); 52.4 (q, J=28 Hz, 0.6×CF$_3$CH); 70.5 (CH$_2$CH$_3$); 120.3 (q, J=Hz, 0.4×CF$_3$); 122.4 (q, J=281 Hz, 0.6×CF$_3$); 213.1 (0.4×C=S); 215.2 (0.6×C=S).

IR (ν, cm$^{-1}$) (CCl$_4$)

2956; 1471; 1441; 1415; 1373; 1328; 1313; 1220; 1178; 1123; 1051; 982; 937.

Mass (IC, NH3)

354 (MH$^+$); 371 (MNH$_4^+$).

|  |  | Element: | |
|---|---|---|---|
|  |  | Carbon | Hydrogen |
| Microanalysis | Calculated (%) | 37.43 | 5.71 |
|  | Actual (%) | 37.66 | 5.94 |

Example 43

4-chloro-2-ethoxythiocarbonylsulphanyl-5,5,5-trifluoro-pentyl ester of acetic acid

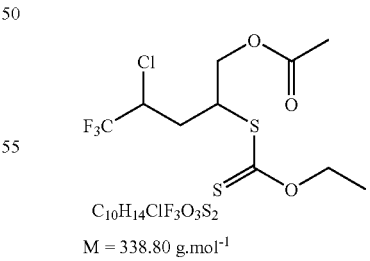

C$_{10}$H$_{14}$ClF$_3$O$_3$S$_2$

M = 338.80 g.mol$^{-1}$

Reaction:

Carried out according to the general operating method with 200 mg (0.84 mmol) of xanthate of example 41 and 232 µL (2.5 mmol) of allyl acetate in 1,2-dichloroethane (2 ml). The reaction is terminated after the addition of 5% of LP (17 mg) and 1 hour 30 minutes under reflux.

Purification:

Chromatography over silica gel (ethyl acetate-petroleum ether 1/9).

Product:

Pale yellow oil.

Yield:

74% (2 diastereoisomers at a ratio of 6/1).

First Diastereoisomer (Majority)

$^1$HNMR ($\delta$, ppm) (CDCl$_3$, 400 MHz)

1.44 (t, J=7.0 Hz, 3H, CH$_2$CH$_3$); 2.06 (s, 3H, COCH$_3$); 2.35-2.55 (m, 2H, CF$_3$CHClCH$_2$); 4.18-4.22 (m, 1H, CHS); 4.30-4.35 (m, 2H, CH$_2$OCOCH$_3$); 4.43 (q, J=7.0 Hz, 2H, CH$_3$CH$_2$); 4.49-4.55 (m, 1H, CF$_3$CH).

$^{13}$CNMR ($\delta$, ppm) (CDCl$_3$, 100 MHz)

13.1 (CH$_3$CH$_2$); 20.7 (CH$_3$CO); 32.0 (CF$_3$CHClCH$_2$); 42.3 (CHS); 56.3 (q, J=28 Hz, CF$_3$CH); 64.0 (CH$_2$OCOCH$_3$); 70.5 (CH$_2$CH$_3$); 118.7 (q, J=281 Hz, CF$_3$); 169.1 (C=O); 210.3 (C=S).

IR ($\nu$, cm$^{-1}$) (CCl$_4$)

2984; 1751 (C=O); 1461; 1438; 1379; 1363; 1310; 1266; 1228; 1185; 1130; 1050.

Mass (IC, NH3)

339 (MH$^+$); 356 (MNH$_4$$^+$).

|  |  | Element: | |
|---|---|---|---|
|  |  | Carbon | Hydrogen |
| Microanalysis | Calculated (%) | 35.44 | 4.17 |
|  | Actual (%) | 35.17 | 4.08 |

Second Diastereoisomer (Minority)

$^1$HNMR ($\delta$, ppm) (CDCl$_3$, 400 MHz)

1.46 (t, J=7.0 Hz, 3H, CH$_2$CH$_3$); 2.11 (s, 3H, COCH$_3$); 2.21-2.31 (m, 2H, CF$_3$CHClCH$_2$); 4.17-4.22 (m, 1H, CHS); 4.29-4.37 (m, 2H, CH$_2$OCOCH$_3$); 4.45 (q, J=7.0 Hz, 2H, CH$_3$CH$_2$); 4.51-4.58 (m, 1H, CF$_3$CH).

$^{13}$CNMR ($\delta$, ppm) (CDCl$_3$, 100 MHz)

13.2 (CH$_3$CH$_2$); 20.9 (CH$_3$CO); 31.1 (CF$_3$CHClCH$_2$); 43.5 (CHS); 58.4 (q, J=28 Hz, CF$_3$CH); 66.1 (CH$_2$OCOCH$_3$); 68.1 (CH$_2$CH$_3$); 120.4 (q, J=281 Hz, CF$_3$); 170.2 (C=O); 212.4 (C=S).

IR ($\nu$, cm$^{-1}$)(CCl$_4$)

2980; 1749 (C=O); 1450; 1437; 1357; 1308; 1264; 1225; 1183; 1135; 1047.

Mass (IC, NH3)

339 (MH$^+$); 356 (MNH$_4$$^+$).

|  |  | Element: | |
|---|---|---|---|
|  |  | Carbon | Hydrogen |
| Microanalysis | Calculated (%) | 35.44 | 4.17 |
|  | Actual (%) | 35.46 | 4.12 |

Example 44

O-ethyl and S-3-chloro-1-(1,3-dioxo-1,3-dihydro-isoindol-2-ylmethyl)-4,4,4-trifluoro-butyl ester of dithiocarbonic acid

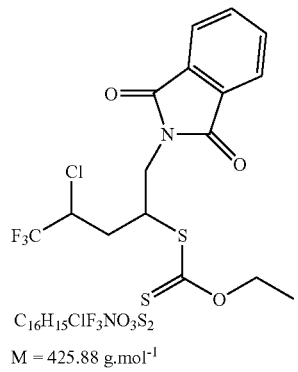

C$_{16}$H$_{15}$ClF$_3$NO$_3$S$_2$

M = 425.88 g.mol$^{-1}$

Reaction:

Carried out according to the general operating method with 200 mg (0.84 mmol) of xanthate of example 41 and 427 mg (2.5 mmol) of N-allylphthalimide in 1,2-dichloroethane (2 ml). The reaction is terminated after the addition of 10% of LP and 3 hours under reflux.

Purification:

Chromatography over silica gel (ethyl acetate-petroleum ether 5/95).

Product:

Translucent crystals.

Yield:

65% (admixture of 2 diastereoisomers at a ratio of 1/1).

$^1$HNMR ($\delta$, ppm) (CDCl$_3$, 400 MHz)

1.37-1.43 (m, 3H, CH$_2$CH$_3$); 2.15-2.24 (m, 0.5H, CF$_3$CHClCH$_2$); 2.29-2.33 (m, 1H, CF$_3$CHClCH$_2$); 2.39-2.43 (m, 0.5H, CF$_3$CHClCH$_2$); 3.93-4.02 (m, 2H, CH$_2$N); 4.01-4.06 (m, 1H, CH$_3$CH$_2$); 4.04-4.14 (m, 1H, CH$_3$CH$_2$); 4.31-4.38 (m, 0.5H, CHS); 4.38-4.47 (m, 0.5H, CHS); 5.49-5.56 (m, 0.5H, CF$_3$CH); 5.59-5.66 (m, 0.5H, CF$_3$CH); 7.72-7.74 (m, 2H, H$_{Ar}$(C$_q$CH=CH)); 7.76-7.84 (m, 2H, H$_{Ar.}$(C$_q$CH=CH).).

$^{13}$CNMR ($\delta$, ppm) (CDCl$_3$, 100 MHz) 12.2 (0.5× CH$_3$CH$_2$); 12.3 (0.5×CH$_3$CH$_2$); 30.8 (0.5×CF$_3$CHClCH$_2$); 31.5 (0.5×CF$_3$CHClCH$_2$); 38.7 (0.5×CH$_2$N); 39.5 (0.5× CH$_2$N); 43.5 (0.5×CHS); 44.0 (0.5×CHS); 49.5 (q, J=31 Hz, 0.5×CF$_3$CH); 50.0 (q, J=35 Hz, 0.5×CF$_3$CH); 115.9 (0.5× CH$_2$CH$_3$); 116.0 (0.5×CH$_2$CH$_3$); 118.4 (q, J=278 Hz, 0.5× CF$_3$); 120.3 (q, J=278 Hz, 0.5×CF$_3$); 129.8 (2×Cq$_{Ar.}$); 132.8 (2×CH$_{Ar.}$(C$_q$CH=CH)); 133.2 (2×CH$_{Ar.}$(C$_q$CH=CH)); 159.3 (C=O$_{Ar.}$); 162.4 (C=O$_{Ar.}$); 211.5 (0.5×C=S); 212.7 (0.5×C=S).

IR ($\nu$, cm$^{-1}$)(CCl$_4$)

2926; 1776; 1722 (C=O); 1430; 1391; 1328; 1265; 1223; 1189; 1131; 1112; 1048; 887.

Mass (IC, NH3)

427 (MH$^+$); 444 (MNH$_4$$^+$).

|               |                |        |          |
|---------------|----------------|--------|----------|
|               |                | Element: |        |
|               |                | Carbon | Hydrogen |
| Microanalysis | Calculated (%) | 49.64  | 3.82     |
|               | Actual (%)     | 49.51  | 3.93     |

Example 45

O-ethyl and S-1-(2-chloro-3,3,3-trifluoro-propyl)-4-oxo-pentyl diester of dithiocarbonic acid

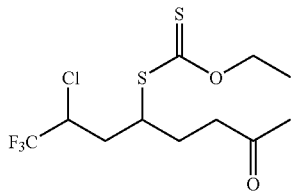

$C_{11}H_{16}Cl_3O_2S_2$
$M = 336.83$ g.mol$^{-1}$

Reaction:
Carried out according to the general operating method with 450 mg (1.89 mmol) of xanthate of example 41 and 657 µL (5.67 mmol) of hex-5-en-2-one in 1,2-dichloroethane (4 ml). The reaction is terminated after the addition of 10% of LP (75 mg) and 3 hours 15 minutes under reflux.

Purification:
Chromatography over silica gel (ethyl acetate-petroleum ether 5/95).

Product:
Dark yellow oil.

Yield:
55% over the four steps, relative to the hemiacetal trifluoroacetaldehyde (admixture of 2 diastereoisomers at a ratio of 1/1)

$^1$HNMR (δ, ppm) (CDCl$_3$, 400 MHz)
0.95 (t, J=7.0 Hz, 1.5H, CH$_2$CH$_3$); 0.98 (t, J=7.0 Hz, 1.5H, CH$_2$CH$_3$); 1.19-1.25 (m, 1H, CH$_2$COCH$_3$); 1.35 (s, 1.5H, COCH$_3$); 1.36 (s, 1.5H, COCH$_3$); 1.35-1.39 (m, 1H, CH$_2$COCH$_3$); 1.41-1.47 (m, 2H, CH$_2$CH$_2$COCH$_3$); 1.69-1.74 (m, 2H, CH$_2$CHCF$_3$); 3.10 (q, J=7.0 Hz, 1H, CH$_3$CH$_2$); 3.12 (q, J=7.0 Hz, 1H, CH$_3$CH$_2$); 3.39-3.46 (m, 0.5H, CHS); 3.51-3.53 (m, 0.5H, CHS); 4.54-4.59 (m, 0.5H, CF$_3$CH); 4.59-4.61 (m, 0.5H, CF$_3$CH).

$^{13}$CNMR (δ, ppm) (CDCl$_3$, 100 MHz)
13.8 (CH$_3$CH$_2$); 22.5 (0.5×CH$_2$COCH$_3$); 22.7 (0.5×CH$_2$COCH$_3$); 28.2 (0.5×CH$_3$CO); 28.3 (0.5×CH$_3$CO); 29.0 (0.5×CHCH$_2$COCH$_3$); 29.2 (0.5×CH$_2$CH$_2$COCH$_3$); 29.3 (0.5×CH$_2$CHCF$_3$); 29.4 (0.5×CH$_2$CHCF$_3$); 31.8 (0.5×CHS); 32.1 (0.5×CHS); 35.7 (q, J=31 Hz, 0.5×CF$_3$CH); 35.8 (q, J=31 Hz, 0.5×CF$_3$CH); 69.6 (0.5×CH$_2$CH$_3$); 70.2 (0.5×CH$_2$CH$_3$); 126.8 (q, J=281 Hz, 0.5×CF$_3$); 127.3 (q, J=281 Hz, 0.5×CF$_3$); 208.2 (0.5×C=O); 209.3 (0.5×C=O); 215.1 (0.5×C=S); 216.2 (0.5×C=S).

IR (ν, cm$^{-1}$)(CCl$_4$)
2926; 2854; 1691 (C=O); 1465; 1216; 1112; 1052.

Mass (IC, NH3)
337 (MH$^+$), 354 (MNH$_4^+$).

|               |                |        |          |
|---------------|----------------|--------|----------|
|               |                | Element: |        |
|               |                | Carbon | Hydrogen |
| Microanalysis | Calculated (%) | 39.23  | 4.79     |
|               | Actual (%)     | 39.03  | 4.73     |

Example 46

Dimethyl and 4-chloro-2-ethoxythiocarbonylsulphanyl-5,5,5-trifluoro-pentyl ester of phosphonic acid

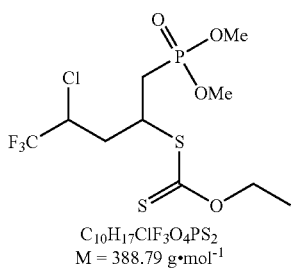

$C_{10}H_{17}ClF_3O_4PS_2$
$M = 388.79$ g·mol$^{-1}$

Reaction:
Carried out according to the general operating method with 450 mg (1.89 mmol) of xanthate of example 41 and 529 µL (5.67 mmol) of dimethylallyl phosphate in 1,2-dichloroethane (2 ml). The reaction is terminated after the addition of 10% of LP (75 mg) and 3 hours 15 minutes under reflux.

Purification:
Chromatography over silica gel (ethyl acetate-petroleum ether 1/9) then increase of polarity up to pure ethyl acetate.

Product:
Dark yellow oil.

Yield:
27% over the four steps (2 diastereoisomers at a ratio of 3/2).

$^1$HNMR (δ, ppm) (CDCl$_3$, 400 MHz)
1.21-1.27 (m, 1.8H, CH$_2$CH$_3$); 1.25-1.30 (m, 1.2H, CH$_2$CH$_3$); 2.20-2.27 (m, 1H, CHS); 3.31-3.39 (m, 1.2H, CF$_3$CHClCH$_2$); 3.49-3.54 (m, 0.8H, CF$_3$CHClCH$_2$); 3.54-3.59 (m, 2H, CH$_2$P); 3.65-3.69 (m, 3H, OCH$_3$); 3.69-3.74 (m, 3H, OCH$_3$); 4.51-4.57 (m, 1.2H, CH$_3$CH$_2$); 4.59-4.65 (m, 0.8H, CH$_3$CH$_2$); 5.81-5.88 (m, 1H, CF$_3$CH).

$^{13}$CNMR (δ, ppm) (CDCl$_3$, 100 MHz)
12.8 (0.4×CH$_3$CH$_2$); 13.0 (0.6×CH$_3$CH$_2$); 21.3 (0.4×OCH$_3$); 22.7 (0.6×OCH$_3$); 23.5 (0.4×OCH$_3$); 24.3 (0.6×OCH$_3$); 27.4 (d, J=134 Hz, 0.4×CH$_2$P); 28.1 (d, J=138 Hz, 0.6×CH$_2$P); 29.3 (q, J=30 Hz, 0.4×CF$_3$CH); 30.1 (q, J=30 Hz, 0.6×CF$_3$CH); 31.3 (0.4×CF$_3$CHClCH$_2$); 31.4 (0.6×CF$_3$CHClCH$_2$); 32.0 (0.4×CHS); 32.3 (0.6×CHS); 67.0 (0.4×CH$_2$CH$_3$); 70.3 (0.6×CH$_2$CH$_3$); 123.4 (q, J=278 Hz, 0.4×CF$_3$); 124.5 (q, J=278 Hz, 0.6×CF$_3$); 212.0 (0.4×C=S); 212.1 (0.6×C=S).

IR (ν, cm$^{-1}$) (CCl$_4$)
2957; 2928; 2855; 1732; 1710; 1263; 1235; 1135; 1043.

Mass (IC, NH3)
390 (MH$^+$); 268 (MH$^+$-HSCSOEt).

Example 47

O-ethyl and
S-3-chloro-1-cyanomethyl-4,4,4-trifluoro-butyl
disaster of dithiocarbonic acid

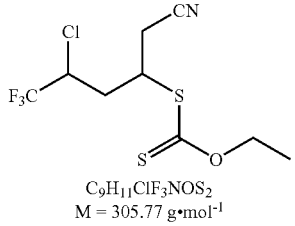

$C_9H_{11}ClF_3NOS_2$
M = 305.77 g·mol$^{-1}$

Reaction:

Carried out according to the general operating method with 450 mg (1.89 mmol) of xanthate of example 41 and 109 μL (5.67 mmol) of but-3-enenitrile in 1,2-dichloroethane (4 ml). The reaction is terminated after the addition of 10% of LP (75 mg) and 3 hours 15 minutes under reflux.

Purification:

Chromatography over silica gel (ethyl acetate-petroleum ether 2/8).

Product:

Dark yellow oil.

Yield:

52% over the 4 steps (admixture of 2 diastereoisomers at a ratio of 2/1)

$^1$HNMR (δ, ppm) (CDCl$_3$, 400 MHz)

1.41 (t, J=5.7 Hz, 2H, CH$_2$CH$_3$); 1.45 (t, J=5.7 Hz, 1H, CH$_2$CH$_3$); 2.12-2.63 (m, 2H, CF$_3$CHClCH$_2$); 3.00-3.06 (m, 2H, CH$_2$CN); 3.99-4.04 (m, 0.3H, CHS); 4.07-4.12 (m, 0.7H, CHS); 4.38-4.42 (m, 0.3H, CF$_3$CH); 4.46-4.53 (m, 0.7H, CF$_3$CH); 4.71 (q, J=5.7 Hz, 0.7H, CH$_3$CH$_2$); 4.74 (q, J=5.7 Hz, 1.3H, CH$_3$CH$_2$).

$^{13}$CNMR (δ, ppm) (CDCl$_3$, 100 MHz)

13.7 (CH$_3$CH$_2$); 23.1 (0.3×CH$_2$CF$_3$CHCl); 25.2 (0.7×CH$_2$CF$_3$CHCl); 25.4 (0.3×CH$_2$CN); 30.5 (0.7×CH$_2$CN); 41.0 (0.3×CHS); 42.0 (0.7×CHS); 52.4 (q, J=43 Hz, 0.3×CF$_3$CH); 53.7 (q, J=43 Hz, 0.7×CF$_3$CH); 70.9 (0.3×CH$_2$CH$_3$); 71.0 (0.7×CH$_2$CH$_3$); 115.5 (0.3×CN); 116.1 (0.7×CN); 122.3 (q, J=286 Hz, 0.3×CF$_3$); 124.4 (q, J=286 Hz, 0.7×CF$_3$); 209.4 (0.3×C=S); 210.3 (0.7×C=S).

IR (ν, cm$^{-1}$) (CCl$_4$)

2926; 1745; 1266; 1237; 1180; 1130; 1050.

Mass (IC, NH3)

306 (MH$^+$); 323 (MNH$_4^+$).

Example 48

O-ethyl and
S-3-chloro-1-diethoxymethyl-4,4,4-trifluoro-pentyl
diester of thiocarbonic acid

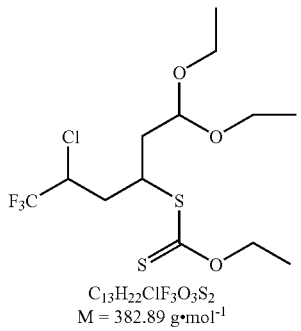

$C_{13}H_{22}ClF_3O_3S_2$
M = 382.89 g·mol$^{-1}$

Reaction:

Carried out according to the general operating method with 400 mg (1.69 mmol) of xanthate of example 41 and 730 mg (5.67 mmol) of 4,4-diethoxy-butene in 1,2-dichloroethane (4 ml). The reaction is terminated after the addition of 15% of LP (101 mg) and 4 hours 45 minutes under reflux.

Purification:

Chromatography over silica gel (ethyl acetate-petroleum ether 5/95).

Product:

Thick pale yellow oil.

Yield:

49% over the 4 steps (2 diastereoisomers at a ratio of 1/1)

First Diastereoisomer $^1$HNMR (δ, ppm) (CDCl$_3$, 400 MHz)

1.26 (t, J=8.2 Hz, 3H, CH$_2$CH$_3$); 1.37-1.42 (m, 2H, CH—CH$_2$—CH(OEt)$_2$); 1.53 (t, J=8.1 Hz, 6H, 2×CH$_2$CH$_3$); 1.66-1.71 (m, 2H, CF$_3$CHClCH$_2$); 3.17 (t, 1H, J=8.2 Hz, CH(OEt)$_2$); 3.47-3.53 (m, 1H, CHS); 4.62 (q, J=8.2 Hz, 2H, CH$_3$CH$_2$O); 4.74 (q, J=8.1 Hz, 4H, 2×CH$_3$CH$_2$O); 6.31 (q, J=7.8 Hz, 1H, CF$_3$CH).

$^{13}$CNMR (δ, ppm) (CDCl$_3$, 100 MHz)

13.8 (2×CH$_3$CH$_2$); 14.2 (CH$_3$CH$_2$); 22.6 (CH—CH$_2$—CH—(OEt)$_2$); 28.3 (CH$_2$CHS); 29.6 (q, J=30 Hz, CF$_3$CH); 31.8 (CHS); 35.8 (CH$_2$CH$_3$); 35.9 (CH$_2$CH$_3$); 69.7 (CH$_2$CH$_3$); 100.8 (CH(OEt)$_2$); 124.5 (q, J=281 Hz, CF$_3$); 215.2 (C=S).

IR (ν, cm$^{-1}$) (CCl$_4$)

2957; 2927; 2855; 1705; 1465; 1442; 1367; 1293; 1243; 1217; 1189; 1113; 1050.

Mass (IC, NH3)

384 (M-H$^+$); 338 (MH$^+$-EtOH).

|  |  | Element: | |
|---|---|---|---|
|  |  | Carbon | Hydrogen |
| Microanalysis | Calculated (%) | 40.78 | 5.79 |
|  | Actual (%) | 40.63 | 5.42 |

Second Diastereoisomer $^1$HNMR (δ, ppm) (CDCl$_3$, 400 MHz)

1.26 (t, J=8.2 Hz, 3H, CH$_2$CH$_3$); 1.41-1.47 (m, 2H, CH—CH$_2$—CH(OEt)$_2$); 1.56 (t, J=8.0 Hz, 6H, 2×CH$_2$CH$_3$); 1.61-1.68 (m, 2H, CF$_3$CHClCH$_2$); 3.67-3.72 (m, 1H, CH(OEt)$_2$); 3.85-3.92 (m, 1H, CHS); 4.71 (q, J=8.2 Hz, 2H, CH$_3$CH$_2$O); 4.78 (q, J=8.0 Hz, 4H, 2×CH$_3$CH$_2$O); 6.12 (q, J=7.8 Hz, 1H, CF$_3$CH).

$^{13}$CNMR (δ, ppm) (CDCl$_3$, 100 MHz)

13.7 (2×CH$_3$CH$_2$); 14.0 (CH$_3$CH$_2$); 22.5 (CH—CH$_2$—CH—(OEt)$_2$); 28.4 (CH$_2$CHS); 29.3 (q, J=30 Hz, CF$_3$CH); 31.6 (CHS); 34.7 (CH$_2$CH$_3$); 34.8 (CH$_2$CH$_3$); 69.5 (CH$_2$CH$_3$); 100.3 (CH(OEt)$_2$); 123.9 (q, J=281 Hz, CF$_3$); 216.0 (C=S).

IR (ν, cm$^{-1}$)(CCl$_4$)

2963; 2931; 2851; 1701; 1467; 1448; 1295; 1257; 1219; 1195; 1115; 1057.

Mass (IC, NH3)

384 (M-H$^+$); 338 (MH$^+$-EtOH).

|  |  | Element: | |
|---|---|---|---|
|  |  | Carbon | Hydrogen |
| Microanalysis | Calculated (%) | 40.78 | 5.79 |
|  | Actual (%) | 40.67 | 5.34 |

Example 49

O-ethyl and S-3-chloro-1-(4-chlorophenoxymethyl)-4,4,4-trifluoro-butyl diester of dithiocarbonic acid

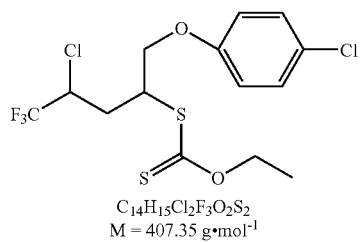

$C_{14}H_{15}Cl_2F_3O_2S_2$
M = 407.35 g·mol$^{-1}$

Reaction:
Carried out according to the general operating method with 400 mg (1.69 mmol) of xanthate of example 41 and 852 mg (5.67 mmol) of 1-allyloxy-4-chloro-benzene in 1,2-dichloroethane (4 ml). The reaction is terminated after the addition of 15% of LP (338 mg) and 4 hours 45 minutes under reflux.

Purification:
Chromatography over silica gel (ethyl acetate-petroleum ether 2/98).

Product:
Pale yellow oil.

Yield:
28% over the four steps (admixture of 2 diastereoisomers at a ratio of 2/1).

$^1$HNMR (δ, ppm) (CDCl$_3$, 400 MHz) 1.37 (t, J=8.3 Hz, 3H, CH$_2$CH$_3$); 1.47-1.51 (m, 0.7H, CF$_3$CHClCH$_2$); 1.51-1.58 (m, 1.3H, CF$_3$CHClCH$_2$); 3.01-3.09 (m, 2H, OCH$_2$CHS); 3.57 (q, J=8.3 Hz, 2H, CH$_3$CH$_2$); 4.01-4.13 (m, 0.3H, CHS); 4.13-4.21 (m, 0.7H, CHS); 4.73 (q, J=5.5 Hz, 0.3H, CF$_3$CH); 4.94 (q, J=5.5 Hz, 0.7H, CF$_3$CH); 6.75-6.85 (m, 2H, H$_{Ar}$. (CH=CCl)); 7.13-7.27 (m, 2H, H$_{Ar}$(CH=CO)).

$^{13}$CNMR (δ, ppm) (CDCl$_3$, 100 MHz)
13.5 (0.3×CH$_3$CH$_2$); 13.6 (0.7×CH$_3$CH$_2$); 23.0 (0.3× CH$_2$CHCF$_3$); 23.0 (0.7×CH$_2$CHCF$_3$); 28.7 (0.3×CHS); 28.9 (0.7×CHS); 29.2 (q, J=32 Hz, 0.3×CF$_3$CH); 29.2 (q, J=32 Hz, 0.7×CF$_3$CH); 32.1 (0.3×CH$_2$O); 32.2 (0.7×CH$_2$O); 63.4 (0.3×CH$_2$CH$_3$); 63.5 (0.7×CH$_2$CH$_3$); 116.2 (C$_{qAr}$Cl); 128.2 (q, J=284 Hz, 0.3×CF$_3$); 128.4 (q, J=284 Hz, 0.7×CF$_3$); 130.3 (C$_{Ar}$H, CH=CCl); 130.4 (C$_{Ar}$(CH=CCl)); 132.7 (2×C$_{Ar}$ (CH=CO)); 137.3 (0.3×C$_{qAr}$O); 137.4 (0.7×C$_{qAr}$O); 210.7 (0.3×C=S); 211.3 (0.7×C=S).

IR (ν, cm$^{-1}$)(CCl$_4$)
2926; 2358; 2350; 1552; 1492; 988; 962.

Mass (IC, NH3)
408 (MH$^+$); 425 (MNH$_4^+$).

|  |  | Element: | |
|---|---|---|---|
|  |  | Carbon | Hydrogen |
| Microanalysis | Calculated (%) | 41.29 | 3.71 |
|  | Actual (%) | 41.01 | 3.57 |

Example 50

O-ethyl and S-3-chloro-4,4,4-trifluoro-1-(2-oxo-pyrrolidin-1-yl)-butyl ester of dithiocarbonic acid di

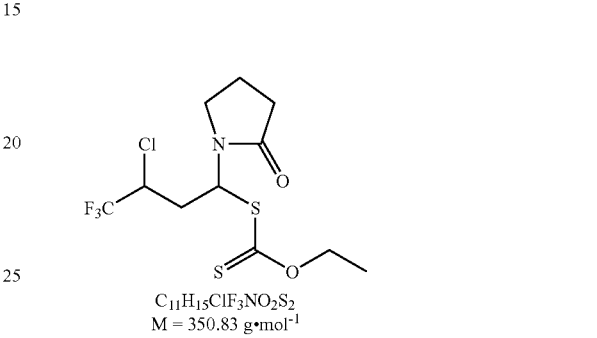

$C_{11}H_{15}ClF_3NO_2S_2$
M = 350.83 g·mol$^{-1}$

Reaction:
Carried out according to the general operating method with 400 mg (1.69 mmol) of xanthate of example 41 and 563 mg (5.07 mmol) of vinyl-pyrrolidin-2-one in 1,2-dichloroethane (4 ml). The reaction is terminated after the addition of 15% of LP (100 mg) and 4 hours 45 minutes under reflux.

Purification:
Chromatography over silica gel (ethyl acetate-petroleum ether 1/9).

Product:
Pale yellow oil.

Yield:
22% over the four steps (admixture of 2 diastereoisomers at a ratio of 1/1).

$^1$HNMR (δ, ppm) CDCl$_3$, 400 MHz)
1.94 (t, J=7.0 Hz, 1.5H, CH$_2$CH$_3$); 2.01 (t, J=7.0 Hz, 1.5H, CH$_2$CH$_3$); 2.43 (m, 2H, CH$_2$CH$_2$CH$_2$); 2.51 (m, 2H, CH$_2$C=O); 3.24-3.37 (m, 2H, NCH$_2$); 3.41-3.55 (m, 2H, CF$_3$CHClCH$_2$); 3.77 (q, J=7.0 Hz, 1H, CH$_3$CH$_2$); 3.83 (q, J=7.0 Hz, 1H, CH$_3$CH$_2$); 6.12-6.16 (m, 0.5H, CHS); 6.17-6.21 (m, 0.5H, CHS); 7.08-7.15 (m, 0.5H, CF$_3$CH); 7.19-7.24 (m, 0.5H, CF$_3$CH).

$^{13}$CNMR (δ, ppm) CDCl$_3$, 100 MHz)
17.3 (0.5×CH$_3$CH$_2$); 18.4 (0.5×CH$_3$CH$_2$); 28.0 (0.5× CH$_2$CH$_2$CH$_2$); 28.4 (0.5×CH$_2$CH$_2$CH$_2$); 29.1 (0.5× CH$_2$C=O); 29.2 (0.5×CH$_2$C=O); 30.4 (0.5× CF$_3$CHClCH$_2$); 30.6 (0.5×CF$_3$CHClCH$_2$); 43.1 (0.5× CH$_2$N); 43.5 (0.5×CH$_2$N); 44.3 (q, J=28 Hz, 0.5×CF$_3$CH); 46.3 (q, J=28 Hz, 0.5×CF$_3$CH); 57.5 (0.5×CHS); 58.4 (0.5× CHS); 70.5 (0.5×CH$_2$CH$_3$); 70.6 (0.5×CH$_2$CH$_3$); 127.4 (q, J=275 Hz, 0.5×CF$_3$); 128.4 (q, J=275 Hz, 0.5×CF$_3$); 177.8 (0.5×C=O); 178.3 (0.5×C=O); 218.1 (0.5×C=S); 220.1 (0.5×C=S).

IR (ν, cm$^{-1}$)(CCl$_4$)
2926; 2335; 1702 (C=O); 1260; 1114; 1049.

Mass (IC, NH3)
352 (MH$^+$); 369 (MNH$_4^+$).

| | | Element: | |
|---|---|---|---|
| | | Carbon | Hydrogen |
| Microanalysis | Calculated (%) | 37.66 | 4.60 |
| | Actual (%) | 37.63 | 4.49 |

Conversion of Adducts

Example 51

1-(3-chloro-4,4,4-trifluoro-but-1-enyl)-pyrrolidin-2-one

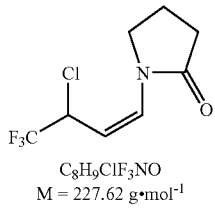

C$_8$H$_9$ClF$_3$NO
M = 227.62 g·mol$^{-1}$

Reaction:
A solution of xanthate of example 50 (200 mg, 0.57 mmol) in chlorobenzene (5 ml) is brought to reflux for 2 hours. The crude reaction product is brought to ambient temperature then concentrated at reduced pressure before being purified.
Purification:
Chromatography over silica gel (dichloromethane-methanol 98/2).
Product:
Pale yellow oil.
Yield:
Quantitative $^1$HNMR (δ, ppm) (CDCl$_3$, 400 MHz)
2.07-2.12 (m, 2H, CH$_2$CH$_2$CH$_2$); 2.45-2.53 (m, 2H, CH$_2$C=O); 2.87-2.93 (m, 2H, NCH$_2$); 4.69-4.77 (m, 1H, CF$_3$CH); 6.75 (dd, J$_1$=13.3 Hz, J$_2$=6.1 Hz, 1H, CH=CHN); 7.41 (d, J=13.3 Hz, 1H, NCH=CH).

$^{13}$CNMR (δ, ppm) (CDCl$_3$, 100 MHz)
22.3 (CH$_2$CH$_2$CH$_2$); 28.8 (CH$_2$CO); 33.4 (CH$_2$N); 45.1 (q, J=28 Hz, CF$_3$CH); 115.1 (CH=CHN); 119.1 (NCH=CH); 141.5 (q, J=275 Hz, CF$_3$); 174.3 (C=O).

IR (ν, cm$^{-1}$)(CCl$_4$)
2926; 2854; 2359; 1741 (C=O); 1699; 1594; 1460; 1407; 1362; 1193.
Mass (IC, NH3)
228 (MH$^+$); 244 (MNH$_4^+$).

| | | Element: | |
|---|---|---|---|
| | | Carbon | Hydrogen |
| Microanalysis | Calculated (%) | 42.22 | 3.99 |
| | Actual (%) | 42.09 | 3.87 |

Example 52

2-(4-chloro-5,5,5-trifluoro-pentyl)-isoindole-1,3-dione

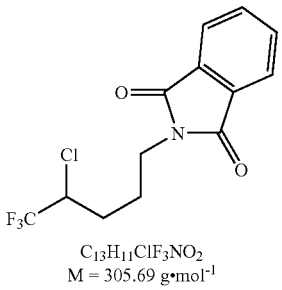

C$_{13}$H$_{11}$ClF$_3$NO$_2$
M = 305.69 g·mol$^{-1}$

Reaction:
LP is added, at a rate of 10 mol % (26 mg, 0.032 mmol) every hour, to a solution of the xanthate adduct of example 44 (134 mg, 0.32 mmol) in propan-2-ol (2 ml), which solution has been degassed beforehand at reflux under argon.
The reaction is stopped after 13 hours under reflux and the addition of 110% of LP (140 mg, 0.35 mmol). The reaction medium is then brought to ambient temperature and concentrated at reduced pressure before being purified.
Purification:
Chromatography over silica gel (ethyl acetate-petroleum ether 2/98).
Product:
Translucent crystals.
Yield:
78%

$^1$H NMR (δ, ppm) (CDCl$_3$, 400 MHz)
1.57-1.63 (m, 2H, CF$_3$CHClCH$_2$); 2.26-2.32 (m, 2H, CH$_2$CH$_2$N); 3.93-4.02 (t, J=6.5 Hz, 2H, CH$_2$N); 7.17-7.23 (m, 1H, CF$_3$CH); 7.62-7.71 (m, 2H, H$_{Ar.}$(C$_q$CH=CH)); 7.73-7.84 (m, 2H, H$_{Ar.}$(C$_q$CH=CH)).

$^{13}$CNMR (δ, ppm) (CDCl$_3$, 100 MHz)
25.1 (CH$_2$CH$_2$N); 28.5 (CF$_3$CHClCH$_2$); 39.8 (CH$_2$N); 49.5 (q, J=31 Hz, CF$_3$CH); 123.5 (2×CH$_{Ar.}$(C$_q$CH=CH)); 125.0 (q, J=281 Hz, CF$_3$); 133.5 (2×Cq$_{Ar.}$); 148.5 (2×CH$_{Ar.}$(C$_q$CH=CH)); 168.8 (2×C=O$_{Ar.}$).

IR (ν, cm$^{-1}$)(CCl$_4$)
2940; 1774; 1502; 1408; 1373; 1346; 1245; 1167; 1127.
Mass (IC, NH3)
307 (MH$^+$); 323 (MNH$_4^+$).

| | | Element: | |
|---|---|---|---|
| | | Carbon | Hydrogen |
| Microanalysis | Calculated (%) | 51.08 | 3.63 |
| | Actual (%) | 51.01 | 3.58 |

What is claimed is:

1. A method for introducing a radical having the formula

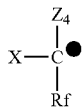

wherein X, $Z_4$ and Rf are as defined below, into an olefin the method comprising reacting said olefin with a compound having the formula (I):

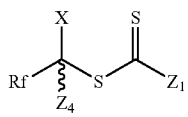

to produce a compound of formula (II)

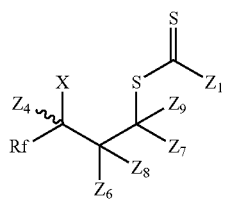

where:

X represents a member selected from the group consisting of a group —$NZ_2Z_3$, a group $OZ_5$, and a halogen atom, where the halogen atom is selected from the group consisting of chlorine, bromine and iodine, where $Z_2$ and $Z_3$ are, independently of each other, a member selected from the group consisting of a hydrogen atom, an alkyl group, a cycloalkyl group, an aryl group oxygen, sulfur, selenium, tellurium, nitrogen, phosphorus, and arsenic; and $Z_5$ represents a hydrogen atom, an alkyl group, a cycloalkyl group, aryl group, or a group which is electroattractive with respect to the oxygen atom to which it is bonded, $Z_1$ represents a group selected from:
(i) an alkyl, acyl, aryl, aralkyl, alkene, alkyne, cyclic hydrocarbon or heterocycle,
(ii) a —$OR^a$ or —$SR^a$ group in which $R^a$ is a group selected from the group consisting of:
(a) alkyl, halogenoalkyl, alkenyl, alkynyl, acyl, aryl, arylalkyl, arylalkenyl, arylalkynyl, a cyclic hydrocarbon, a heterocycle and a polymer chain;
(b) a —$CR^bR^cPO(OR^d)(OR^e)$ group in which:
$R^b$ and $R^c$ each represent, independently of each other, a hydrogen atom, a halogen atom, an alkyl, perfluoroalkyl, a cyclic hydrocarbon, a heterocycle, —$NO_2$, —NCO, CN, —$R^f$, —$SO_3R^f$, —$SR^f$, —$NR^fR^g$, —$COOR^f$, —$O_2CR^f$, —$CONR^fR^g$, or —$NCOR^fR^g$ group, in which $R^f$ and $R^g$ each independently represent an alkyl, alkenyl, alkynyl, cycloalkenyl, cycloalkynyl, or an aryl group which is optionally condensed to a heterocycle, alkaryl, arylalkyl, heteroaryl, or $R^b$ and $R^c$ form, together with the carbon atom to which they are attached, a C=O group, a C=S group, a cyclic hydrocarbon or a heterocycle; and $R^d$ and $R^e$ each represent, independently of each other, a radical which has the same definition as the group Rf;

or $R^d$ and $R^e$ together form a hydrocarbon chain which comprises from 2 to 4 carbon atoms, and which is optionally interrupted by a group selected from —O—, —S— and —$NR^h$—; in which $R^h$ has the same definition as the group $R^f$; and (iii) a group —$NR^iR^j$, in which:
$R^i$ and $R^j$ represent, independently of each other, an alkyl, halogenoalkyl, alkenyl, alkynyl, acyl, ester, aryl, arylalkyl, arylalkenyl, arylalkynyl, cyclic hydrocarbon or a heterocycle group; or
$R^i$ and $R^j$ together form a hydrocarbon chain which comprises from 2 to 4 carbon atoms and which is optionally interrupted by an O, S, or —$NR^H$, or $R^H$ group, where the $R^H$ group has the same definition as the $R^f$ group, $Z_4$ represents a hydrogen atom, an alkyl or cycloalkyl group, and Rf represents
(i) a halogen atom;
(ii) fluoroalkyl;
(iii) per-halogenated aryl radical, or
(iv) a radical selected from $R_A$—$CF_2$—, $R_A$—$CF_2$—$CF_2$—, $R_A$—$CF_2$—$CF(CF_3)$—, $CF_3$—$C(R_A)F$— and $(CF_3)R_A$—, where $R_A$ is an alkyl, acyl, aryl, aralkyl, alkene, alkyne, cyclic hydrocarbon or a heterocycle,
or a salt of compounds of formula (I).

2. The method according to claim 1, where X in the compound of formula (I) represents —$NZ_2Z_3$, —$OZ_5$ or a halogen atom (Hal), in which:

$Z_2$ and $Z_3$ represent, independently of each other, a hydrogen atom, an alkyl, cycloalkyl, aryl group or an electroattractive group, wherein said electroattractive group is a group having a value of 0.05 or greater on the Hammett constant scale, or $Z_2$ and $Z_3$ can be bonded in order to form a heterocycle with the nitrogen atom, and $Z_5$ represents a hydrogen atom, an alkyl, cycloalkyl, aryl or a group which is electroattractive with respect to the electron density of the oxygen atom to which it is bonded.

3. The method according to claim 2, wherein the compound of formula (I) has the formula (Ia):

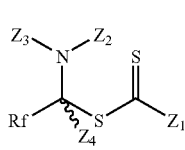
Formula (Ia)

in which $Z_1$, $Z_2$, $Z_3$, $Z_4$ and Rf are as defined in claims 1 or 2.

4. The method according to claim 3, in which $Z_2$ and $Z_3$ represent, independently of each other, a hydrogen atom, an alkyl, cycloalkyl, aryl, or an electroattractive group, wherein said electroattractive group is a group having a value of 0.05 or greater on the Hammett constant scale.

5. The method according to claim 2, wherein the compound of formula (I) has the formula (Ib):

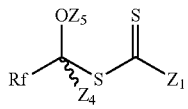

in which $Z_1$, $Z_4$, $Z_5$ and Rf are as defined in claims 1 or 2.

6. The method according to claim 2, wherein the compound of formula (I) has the formula (Ic):

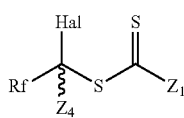

in which Rf, $Z_1$, $Z_4$ and Hal are as defined in claims 1 or 2.

7. The method according to claim 1, wherein $Z_4$ is a hydrogen atom.

8. The method according to claim 1, wherein Rf is a perfluoroalkyl group or a poly- or per-halogenated aryl radical comprising at least one fluorine atom.

9. The method according to claim 8, wherein the perfluoroalkyl group is a trifluoromethyl radical.

10. The method according to claim 2, wherein $Z_5$ or at least one of the groups $Z_2$ and $Z_3$ represents an electroattractive group selected from the group consisting of acyl, aroyl, carboxyl, alkyloxycarbonyl, aryloxycarbonyl, aralkyloxycarbonyl, carbamoyl, alkylcarbamoyl, arylcarbamoyl, cyano, sulphonyl, alkylsulphonyl, and arylsulphonyl groups.

11. The method according to claim 10, wherein $Z_5$ or at least one of the groups $Z_2$ and $Z_3$ represents an electroattractive acyl, alkoxycarbonyl or aralkyloxycarbonyl group.

12. The method according to claim 11, wherein the electroattractive group is an acetyl, t-butoxycarbonyl or benzyloxycarbonyl group.

13. The method according to claim 10, wherein the group $Z_2$ or $Z_3$ represents a hydrogen atom if it is not an electroattractive group selected from the group consisting of acyl, aroyl, carboxyl, alkyloxycarbonyl, aryloxycarbonyl, aralkyloxycarbonyl, carbamoyl, alkylcarbamoyl, arylcarbamoyl, cyano, sulphonyl, alkylsulphonyl, and arylsulphonyl groups.

14. The method according to claim 1, wherein $Z_1$ represents —$OR^a$, where $R^a$ is defined in claim 1.

15. The method according to claim 14, wherein $R^a$ represents an alkyl group.

16. The method according to claim 2, wherein the Hal atom is a chlorine atom.

17. The method according to claim 2, wherein $Z_5$ is a hydrogen atom.

18. The method according to claim 1, wherein the compound of formula (I) is selected from the group consisting of:
S-[1-(N-acetylamino)-2,2,2-trifluoroethyl]-O-ethyl dithiocarbonate;
O-ethyl and S-1-benzoylamino-2,2,2-trifluoro-ethyl diester of dithiocarbonic acid;
O-ethyl and S-(1-hydroxy-2,2,2-trifluoro-ethyl) ester of dithiocarbonic acid;
O-ethyl and S-(1-acetyl-2,2,2-trifluoro-ethyl) ester of dithiocarbonic acid;
1-ethoxythiocarbonylsulphanyl-2,2,2-trifluoro-ethyl ester of benzoic acid; and
O-ethyl and S-1-chloro-2,2,2-trifluoro-ethyl ester of dithiocarbonic acid.

19. The method according to claim 1, wherein a radical of the formula $(Z_2Z_3N)(Rf)(Z_4)C$— is introduced into an olefin,
where $Z_2$ and $Z_3$ represent, independently of each other, a hydrogen atom, an alkyl, cycloalkyl, aryl or an electroattractive group, wherein said electroattractive group is a group having a value of 0.05 or greater on the Hammett constant scale, or
$Z_2$ and $Z_3$ can be bonded in order to form a heterocycle with the nitrogen atom, and $Z_4$ is defined in claim 1.

20. The method according to claim 1, wherein the radical of formula

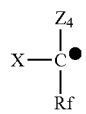

has the formula:

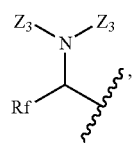

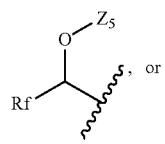

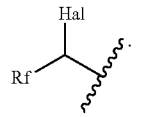

21. The method of claim 1, wherein Rf is fluorine.

22. The method of claim 2, wherein at least one of the radicals $Z_2$ and $Z_3$ has an electroattractive effect with respect to the electron density of the nitrogen atom to which they are bonded.

23. The method of claim 3, wherein at least one of the radicals $Z_2$ and $Z_3$ has an electroattractive effect with respect to the electron density of the nitrogen atom to which they are bonded.

24. The method of claim 1, wherein the olefin has the structure of formula (III)

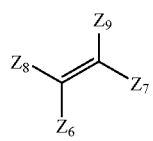

in which $Z_6$, $Z_7$, $Z_8$ and $Z_9$ independently represent a hydrogen atom, a halogen atom, an alkyl, halogenoalkyl, alkenyl, alkynyl, acyl, aryl, arylalkyl, arylalkenyl, arylalkynyl, a cyclic hydrocarbon, a heterocycle, a polymer chain, $-(CH_2)_m-OR^k$, $-(CH_2)_m-CH(OR^k)(OR^l)$, $CH(OR^k)(OR^l)-$, $-(CH_2)_m-SR^k$, $-(CH_2)_m-SO_3R^k$, $-(CH_2)_m-NO_2$, $-(CH_2)_m-CN$, $-(CH_2)_m-R^k$, $-[(CH_2)_m-P(O)(OR^k)(OR^l)]$, $-(CH_2)_m-SiRkRlR^m$, $-(CH_2)_m-COOR^k$, $-(CH_2)_m-NCOR^k$, or $-(CH_2)_m-NR^kR^l$, in which:

$R^k$, $R^l$ and $R^m$ each independently are an alkyl, acyl, aryl, alkenyl, alkynyl, aralkyl, alkaryl, alkylsulphonyl, arylsulphonyl, a cyclic hydrocarbon or a heterocycle, or $R^k$ and $R^l$ together form, with the atom to which they are attached, a cyclic hydrocarbon or a heterocycle;

m is a whole number which is greater than or equal to 1, or $Z_6$, $Z_7$, $Z_8$ and $Z_9$ form, two by two, one or more cyclic hydrocarbon(s) or heterocycle(s), the groups $Z_6$, $Z_7$, $Z_8$ and $Z_9$ which do not form a cycle being selected from the radicals mentioned above.

25. The method according to claim 1, wherein the olefin is selected from the group consisting of vinyl acetate, hex-5-en-2-one, allyl acetate, vinyltrimethylsilane, but-3-enenitrile, 3,3-diethoxypropene and diethyl allylphosphonate.

* * * * *